United States Patent
Schroeder et al.

(10) Patent No.: US 9,198,757 B2
(45) Date of Patent: Dec. 1, 2015

(54) METHODS AND DEVICES FOR IMPROVING MITRAL VALVE FUNCTION

(75) Inventors: Richard Schroeder, Fridley, MN (US);
Robert Vidlund, Maplewood, MN (US);
Jason Kalgreen, Edina, MN (US); Cyril Schweich, Jr., Maple Grove, MN (US);
Todd Mortier, Minneapolis, MN (US);
Marc Simmon, Becker, MN (US); Peter Keith, St. Paul, MN (US)

(73) Assignee: Edwards Lifesciences, LLC, Irvine, CA (US)

(*) Notice: Subject to any disclaimer, the term of this patent is extended or adjusted under 35 U.S.C. 154(b) by 807 days.

(21) Appl. No.: 12/498,956

(22) Filed: Jul. 7, 2009

(65) Prior Publication Data

US 2009/0270980 A1    Oct. 29, 2009

Related U.S. Application Data

(63) Continuation of application No. 10/840,511, filed on May 7, 2004, now abandoned, which is a continuation of application No. 10/762,513, filed on Jan. 23, 2004, now abandoned, which is a continuation of application No. 09/680,435, filed on Oct. 6, 2000, now Pat. No. 6,723,038.

(51) Int. Cl.
*A61B 1/00* (2006.01)
*A61F 2/24* (2006.01)
(Continued)

(52) U.S. Cl.
CPC ......... *A61F 2/2487* (2013.01); *A61B 17/00234* (2013.01); *A61B 17/1227* (2013.01);
(Continued)

(58) Field of Classification Search
CPC .................................................. A61M 1/101
USPC ............. 600/16–18, 437, 443, 445, 449, 450
See application file for complete search history.

(56) References Cited

U.S. PATENT DOCUMENTS 963,899 A    7/1910  Kistler
3,019,790 A    2/1962  Militana
(Continued)

FOREIGN PATENT DOCUMENTS

DE    32 27 984 A1    2/1984
DE    36 14 292 C1    11/1987
(Continued)

OTHER PUBLICATIONS

Edie, M.D. et al., "Surgical repair of single ventricle," *The Journal of Thoracic and Cardiovascular Surgery*, vol. 66, No. 3, Sep. 1973, pp. 350-360.
(Continued)

*Primary Examiner* — Christopher D Koharski
*Assistant Examiner* — Nadia A Mahmood
(74) *Attorney, Agent, or Firm* — Richard B. Cates

(57) ABSTRACT

The various aspects of the invention pertain to devices and related methods for treating heart conditions, including, for example, dilatation, valve incompetencies, including mitral valve leakage, and other similar heart failure conditions. The devices and related methods of the present invention operate to assist in the apposition of heart valve leaflets to improve valve function. According to one aspect of the invention, a method improves the function of a valve of a heart by placing an elongate member transverse a heart chamber so that each end of the elongate member extends through a wall of the heart, and placing first and second anchoring members external the chamber. The first and second anchoring members are attached to first and second ends of the elongate member to fix the elongate member in a position across the chamber so as to reposition papillary muscles within the chamber. Also described herein is a method for placing a splint assembly transverse a heart chamber by advancing an elongate member through vasculature structure and into the heart chamber.

23 Claims, 34 Drawing Sheets

(51) Int. Cl.
    *A61B 17/00*      (2006.01)
    *A61B 17/122*     (2006.01)
    *A61B 17/04*      (2006.01)

(52) U.S. Cl.
    CPC ............. *A61B2017/00243* (2013.01); *A61B 2017/0404* (2013.01); *A61B 2017/048* (2013.01); *A61B 2017/0496* (2013.01); *A61F 2/2481* (2013.01)

(56) References Cited

U.S. PATENT DOCUMENTS

| | | |
|---|---|---|
| 3,656,185 A | 4/1972 | Carpentier |
| 3,980,086 A | 9/1976 | Kletschka et al. |
| 4,035,849 A | 7/1977 | Angell et al. |
| 4,055,861 A | 11/1977 | Carpentier et al. |
| 4,192,293 A | 3/1980 | Asrican |
| 4,217,665 A | 8/1980 | Bex et al. |
| 4,261,342 A | 4/1981 | Aranguren Duo |
| 4,300,564 A | 11/1981 | Furihata |
| 4,306,319 A | 12/1981 | Kaster |
| 4,343,048 A | 8/1982 | Ross et al. |
| 4,372,293 A | 2/1983 | Vijil-Rosales |
| 4,409,974 A | 10/1983 | Freedland |
| 4,536,893 A | 8/1985 | Parravicini |
| 4,579,120 A | 4/1986 | MacGregor |
| 4,592,342 A | 6/1986 | Salmasian |
| 4,629,459 A | 12/1986 | Ionescu et al. |
| 4,632,101 A | 12/1986 | Freedland |
| 4,690,134 A | 9/1987 | Snyders |
| 4,705,040 A | 11/1987 | Mueller et al. |
| 4,936,857 A | 6/1990 | Kulik |
| 4,944,753 A | 7/1990 | Burgess et al. |
| 4,960,424 A | 10/1990 | Grooters |
| 4,991,578 A | 2/1991 | Cohen |
| 4,997,431 A | 3/1991 | Isner et al. |
| 5,061,277 A | 10/1991 | Carpentier et al. |
| 5,104,407 A | 4/1992 | Lam et al. |
| 5,106,386 A | 4/1992 | Isner et al. |
| 5,131,905 A | 7/1992 | Grooters |
| RE34,021 E | 8/1992 | Mueller et al. |
| 5,152,765 A | 10/1992 | Ross et al. |
| 5,156,621 A | 10/1992 | Navia et al. |
| 5,169,381 A | 12/1992 | Snyders |
| 5,192,314 A | 3/1993 | Daskalakis |
| 5,250,049 A | 10/1993 | Michael |
| 5,256,132 A | 10/1993 | Snyders |
| 5,258,015 A | 11/1993 | Li et al. |
| 5,284,488 A | 2/1994 | Sideris |
| 5,300,087 A | 4/1994 | Knoepfler |
| 5,312,642 A | 5/1994 | Chesterfield et al. |
| 5,360,444 A | 11/1994 | Kusuhara |
| 5,376,112 A | 12/1994 | Duran |
| 5,383,840 A | 1/1995 | Heilman et al. |
| 5,385,528 A | 1/1995 | Wilk |
| 5,389,096 A | 2/1995 | Aita et al. |
| 5,397,331 A | 3/1995 | Himpens et al. |
| 5,417,709 A | 5/1995 | Slater |
| 5,433,727 A | 7/1995 | Sideris |
| 5,445,600 A | 8/1995 | Abdulla |
| 5,450,860 A | 9/1995 | O'Connor |
| 5,452,733 A | 9/1995 | Sterman et al. |
| 5,458,574 A | 10/1995 | Machold et al. |
| 5,496,305 A | 3/1996 | Kittrell et al. |
| 5,509,428 A | 4/1996 | Dunlop |
| 5,522,884 A | 6/1996 | Wright |
| 5,533,958 A | 7/1996 | Wilk |
| 5,571,215 A | 11/1996 | Sterman et al. |
| 5,584,803 A | 12/1996 | Stevens et al. |
| 5,593,424 A | 1/1997 | Northrup, III |
| 5,607,471 A | 3/1997 | Seguin et al. |
| 5,608,849 A * | 3/1997 | King, Jr. .................. 345/419 |
| 5,655,548 A | 8/1997 | Nelson et al. |
| 5,665,092 A | 9/1997 | Mangiardi et al. |
| 5,674,279 A | 10/1997 | Wright et al. |
| 5,682,906 A | 11/1997 | Sterman et al. |
| 5,702,343 A | 12/1997 | Alferness |
| 5,713,954 A | 2/1998 | Rosenberg et al. |
| 5,718,725 A | 2/1998 | Sterman et al. |
| 5,738,649 A | 4/1998 | Macoviak |
| 5,755,783 A | 5/1998 | Stobie et al. |
| 5,758,663 A | 6/1998 | Wilk et al. |
| 5,766,234 A | 6/1998 | Chen et al. |
| 5,776,189 A | 7/1998 | Khalid et al. |
| 5,800,334 A | 9/1998 | Wilk |
| 5,800,528 A | 9/1998 | Lederman et al. |
| 5,800,531 A | 9/1998 | Cosgrove et al. |
| 5,807,384 A | 9/1998 | Mueller |
| 5,814,097 A | 9/1998 | Sterman et al. |
| 5,824,066 A | 10/1998 | Gross |
| 5,824,069 A | 10/1998 | Lemole |
| 5,840,059 A | 11/1998 | March et al. |
| 5,849,005 A | 12/1998 | Garrison et al. |
| 5,855,601 A | 1/1999 | Bessler et al. |
| 5,855,614 A | 1/1999 | Stevens et al. |
| 5,865,791 A | 2/1999 | Whayne et al. |
| 5,876,436 A | 3/1999 | Vanney et al. |
| 5,888,240 A | 3/1999 | Carpentier et al. |
| 5,902,229 A | 5/1999 | Tsitlik et al. |
| 5,928,281 A | 7/1999 | Huynh et al. |
| 5,944,738 A | 8/1999 | Amplatz et al. |
| 5,957,977 A | 9/1999 | Melvin |
| 5,961,440 A * | 10/1999 | Schweich et al. ............... 600/16 |
| 5,961,539 A | 10/1999 | Northrup, III et al. |
| 5,961,549 A | 10/1999 | Nguyen et al. |
| 5,967,990 A | 10/1999 | Thierman et al. |
| 5,971,910 A | 10/1999 | Tsitlik et al. |
| 5,971,911 A | 10/1999 | Wilk |
| 5,972,022 A | 10/1999 | Huxel |
| 5,972,030 A | 10/1999 | Garrison et al. |
| 5,984,857 A | 11/1999 | Buck et al. |
| 5,984,917 A | 11/1999 | Fleischman et al. |
| 5,999,678 A | 12/1999 | Murphy-Chutorian et al. |
| 6,001,126 A | 12/1999 | Nguyen-Thien-Nhon |
| 6,019,722 A | 2/2000 | Spence et al. |
| 6,024,096 A | 2/2000 | Buckberg |
| 6,024,756 A | 2/2000 | Huebsch et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,086,532 A | 7/2000 | Panescu et al. |
| 6,095,968 A | 8/2000 | Snyders |
| 6,102,944 A | 8/2000 | Huynh et al. |
| 6,110,100 A | 8/2000 | Talpade |
| 6,113,536 A | 9/2000 | Aboul-Hosn et al. |
| 6,113,636 A | 9/2000 | Ogle |
| 6,117,159 A | 9/2000 | Huebsch et al. |
| 6,120,520 A | 9/2000 | Saadat et al. |
| 6,123,662 A | 9/2000 | Alferness et al. |
| 6,125,852 A | 10/2000 | Stevens et al. |
| 6,126,590 A | 10/2000 | Alferness |
| 6,129,758 A | 10/2000 | Love |
| 6,132,438 A | 10/2000 | Fleischman et al. |
| 6,143,025 A | 11/2000 | Stobie et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,165,183 A | 12/2000 | Kuehn et al. |
| 6,169,922 B1 | 1/2001 | Alferness et al. |
| 6,174,279 B1 | 1/2001 | Girard |
| 6,174,332 B1 | 1/2001 | Loch et al. |
| 6,179,791 B1 | 1/2001 | Krueger |
| 6,182,664 B1 | 2/2001 | Cosgrove |
| 6,183,411 B1 | 2/2001 | Mortier et al. |
| 6,183,512 B1 | 2/2001 | Howanec, Jr. et al. |

(56) References Cited

U.S. PATENT DOCUMENTS

| | | |
|---|---|---|
| 6,190,408 B1 | 2/2001 | Melvin |
| 6,193,648 B1 | 2/2001 | Krueger |
| 6,197,053 B1 | 3/2001 | Cosgrove et al. |
| 6,206,004 B1 | 3/2001 | Schmidt et al. |
| 6,206,820 B1 | 3/2001 | Kazi et al. |
| 6,210,432 B1 | 4/2001 | Solem et al. |
| 6,217,610 B1 | 4/2001 | Carpentier et al. |
| 6,221,013 B1 | 4/2001 | Panescu et al. |
| 6,221,103 B1 | 4/2001 | Melvin |
| 6,221,104 B1 | 4/2001 | Buckberg et al. |
| 6,224,540 B1 | 5/2001 | Lederman et al. |
| 6,230,714 B1 | 5/2001 | Alferness et al. |
| 6,231,518 B1 | 5/2001 | Grabek et al. |
| 6,231,561 B1 | 5/2001 | Frazier et al. |
| 6,231,602 B1 | 5/2001 | Carpentier et al. |
| 6,238,334 B1 | 5/2001 | Easterbrook, III et al. |
| 6,241,654 B1 | 6/2001 | Alferness |
| 6,245,102 B1 | 6/2001 | Jayaraman |
| 6,245,105 B1 | 6/2001 | Nguyen et al. |
| 6,250,308 B1 | 6/2001 | Cox |
| 6,251,061 B1 | 6/2001 | Hastings et al. |
| 6,258,021 B1 | 7/2001 | Wilk |
| 6,258,023 B1 | 7/2001 | Rogers et al. |
| 6,260,552 B1 | 7/2001 | Mortier et al. |
| 6,260,820 B1 | 7/2001 | Chowdhury |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,283,993 B1 | 9/2001 | Cosgrove et al. |
| 6,290,674 B1 | 9/2001 | Roue et al. |
| 6,293,906 B1 | 9/2001 | Vanden Hoek et al. |
| 6,309,370 B1 | 10/2001 | Haim et al. |
| 6,312,447 B1 | 11/2001 | Grimes |
| 6,314,322 B1 | 11/2001 | Rosenberg |
| 6,328,727 B1 | 12/2001 | Frazier et al. |
| 6,331,157 B2 | 12/2001 | Hancock |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,338,712 B2 | 1/2002 | Spence et al. |
| 6,343,605 B1 | 2/2002 | Lafontaine |
| 6,360,749 B1 | 3/2002 | Jayaraman |
| 6,361,545 B1 | 3/2002 | Macoviak et al. |
| 6,370,429 B1 | 4/2002 | Alferness et al. |
| 6,375,608 B1 | 4/2002 | Alferness |
| 6,379,366 B1 | 4/2002 | Fleischman et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,406,422 B1 | 6/2002 | Landesberg |
| 6,409,759 B1 | 6/2002 | Peredo |
| 6,409,760 B1 | 6/2002 | Melvin |
| 6,416,459 B1 | 7/2002 | Haindl |
| 6,419,669 B1 | 7/2002 | Frazier et al. |
| 6,423,051 B1 | 7/2002 | Kaplan et al. |
| 6,425,856 B1 | 7/2002 | Shapland et al. |
| 6,432,039 B1 | 8/2002 | Wardle |
| 6,432,059 B2 | 8/2002 | Hickey |
| 6,436,088 B2 | 8/2002 | Frazier et al. |
| 6,439,237 B1 | 8/2002 | Buckberg et al. |
| 6,443,949 B2 | 9/2002 | Altman |
| 6,450,171 B1 | 9/2002 | Buckberg et al. |
| 6,458,100 B2 | 10/2002 | Roue et al. |
| 6,461,366 B1 | 10/2002 | Seguin |
| 6,478,729 B1 | 11/2002 | Rogers et al. |
| 6,482,146 B1 | 11/2002 | Alferness et al. |
| 6,488,706 B1 | 12/2002 | Solymar |
| 6,494,825 B1 | 12/2002 | Talpade |
| 6,508,756 B1 | 1/2003 | Kung et al. |
| 6,511,426 B1 | 1/2003 | Hossack et al. |
| 6,514,194 B2 | 2/2003 | Schweich, Jr. et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,537,314 B2 | 3/2003 | Langberg et al. |
| 6,544,167 B2 | 4/2003 | Buckberg et al. |
| 6,544,180 B1 | 4/2003 | Doten et al. |
| 6,547,821 B1 | 4/2003 | Taylor et al. |
| 6,569,198 B1 | 5/2003 | Wilson et al. |
| 6,572,529 B2 | 6/2003 | Wilk |
| 6,582,355 B2 | 6/2003 | Alferness et al. |
| 6,587,734 B2 | 7/2003 | Okuzumi |
| 6,589,160 B2 | 7/2003 | Schweich, Jr. et al. |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,278 B2 | 9/2003 | Kampichler |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,619,291 B2 | 9/2003 | Hlavka |
| 6,622,730 B2 | 9/2003 | Ekvall et al. |
| 6,626,821 B1 | 9/2003 | Kung et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,645,139 B2 | 11/2003 | Haindl |
| 6,651,671 B1 | 11/2003 | Donlon et al. |
| 6,656,221 B2 | 12/2003 | Taylor et al. |
| 6,663,558 B2 | 12/2003 | Lau et al. |
| 6,669,708 B1 | 12/2003 | Nissenbaum et al. |
| 6,673,009 B1 | 1/2004 | Vanden Hoek et al. |
| 6,676,702 B2 | 1/2004 | Mathis |
| 6,681,773 B2 | 1/2004 | Murphy et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,685,646 B2 | 2/2004 | Cespedes et al. |
| 6,689,048 B2 | 2/2004 | Vanden Hoek et al. |
| 6,695,768 B1 | 2/2004 | Levine et al. |
| 6,695,866 B1 | 2/2004 | Kuehn et al. |
| 6,701,929 B2 | 3/2004 | Hussein |
| 6,702,732 B1 | 3/2004 | Lau et al. |
| 6,702,763 B2 | 3/2004 | Murphy et al. |
| 6,702,826 B2 | 3/2004 | Liddicoat et al. |
| 6,706,065 B2 | 3/2004 | Langberg et al. |
| 6,709,382 B1 | 3/2004 | Horner |
| 6,709,456 B2 | 3/2004 | Langberg et al. |
| 6,712,804 B2 | 3/2004 | Roue et al. |
| 6,716,158 B2 | 4/2004 | Raman et al. |
| 6,719,767 B1 | 4/2004 | Kimblad |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,016 B1 | 5/2004 | Cox et al. |
| 6,733,525 B2 | 5/2004 | Yang et al. |
| 6,740,107 B2 | 5/2004 | Loeb et al. |
| 6,752,813 B2 | 6/2004 | Goldfarb et al. |
| 6,755,777 B2 | 6/2004 | Schweich, Jr. et al. |
| 6,755,779 B2 | 6/2004 | Vanden Hoek et al. |
| 6,767,362 B2 | 7/2004 | Schreck |
| 6,769,434 B2 | 8/2004 | Liddicoat et al. |
| 6,776,754 B1 | 8/2004 | Wilk |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,805,710 B2 | 10/2004 | Bolling et al. |
| 6,810,882 B2 | 11/2004 | Langberg et al. |
| 6,814,700 B1 | 11/2004 | Mueller et al. |
| 6,824,562 B2 | 11/2004 | Mathis et al. |
| 6,830,585 B1 | 12/2004 | Artof et al. |
| 6,837,247 B2 | 1/2005 | Buckberg et al. |
| 6,846,296 B1 | 1/2005 | Milbocker et al. |
| 6,858,039 B2 | 2/2005 | McCarthy |
| 6,875,224 B2 | 4/2005 | Grimes |
| 6,876,887 B2 | 4/2005 | Okuzumi |
| 6,881,185 B2 | 4/2005 | Vanden Hock et al. |
| 6,887,192 B1 | 5/2005 | Whayne et al. |

(56) References Cited

U.S. PATENT DOCUMENTS

| | | | |
|---|---|---|---|
| 6,890,353 B2 | 5/2005 | Cohn et al. | |
| 6,893,392 B2 | 5/2005 | Alferness | |
| 6,896,652 B2 | 5/2005 | Alferness et al. | |
| 6,902,522 B1 | 6/2005 | Walsh et al. | |
| 6,908,426 B2 | 6/2005 | Shapland et al. | |
| 6,908,478 B2 | 6/2005 | Alferness et al. | |
| 6,913,608 B2 | 7/2005 | Liddicoat et al. | |
| 6,918,917 B1 | 7/2005 | Nguyen et al. | |
| 6,921,407 B2 | 7/2005 | Nguyen et al. | |
| 6,949,122 B2 | 9/2005 | Adams et al. | |
| 6,951,534 B2 | 10/2005 | Girard et al. | |
| 6,955,689 B2 | 10/2005 | Ryan et al. | |
| 6,959,711 B2 | 11/2005 | Murphy et al. | |
| 6,960,229 B2 | 11/2005 | Mathis et al. | |
| 6,962,605 B2 | 11/2005 | Cosgrove et al. | |
| 6,966,926 B2 | 11/2005 | Mathis | |
| 6,976,995 B2 | 12/2005 | Mathis et al. | |
| 6,989,028 B2 | 1/2006 | Lashinski et al. | |
| 6,997,865 B2 | 2/2006 | Alferness et al. | |
| 6,997,951 B2 | 2/2006 | Solem et al. | |
| 7,011,682 B2 | 3/2006 | Lashinski et al. | |
| 7,022,064 B2 | 4/2006 | Alferness et al. | |
| 7,025,719 B2 | 4/2006 | Alferness et al. | |
| 7,029,466 B2 * | 4/2006 | Altman | 604/508 |
| 7,044,967 B1 | 5/2006 | Solem et al. | |
| 7,056,280 B2 | 6/2006 | Buckberg et al. | |
| 7,060,021 B1 | 6/2006 | Wilk | |
| 7,070,618 B2 | 7/2006 | Streeter | |
| 7,090,695 B2 | 8/2006 | Solem et al. | |
| 7,112,207 B2 | 9/2006 | Allen et al. | |
| 7,115,110 B2 | 10/2006 | Frazier et al. | |
| 7,153,258 B2 | 12/2006 | Alferness et al. | |
| 7,163,507 B2 | 1/2007 | Alferness | |
| 7,166,071 B2 | 1/2007 | Alferness | |
| 7,166,126 B2 | 1/2007 | Spence et al. | |
| 7,189,199 B2 | 3/2007 | McCarthy et al. | |
| 7,192,442 B2 | 3/2007 | Solem et al. | |
| 7,214,181 B2 | 5/2007 | Shapland et al. | |
| 7,226,467 B2 | 6/2007 | Lucatero et al. | |
| 7,229,469 B1 | 6/2007 | Witzel et al. | |
| 7,252,632 B2 | 8/2007 | Shapland et al. | |
| 7,255,674 B2 | 8/2007 | Alferness | |
| 7,261,684 B2 | 8/2007 | Alferness | |
| 7,264,587 B2 | 9/2007 | Chin | |
| 7,275,546 B2 | 10/2007 | Buckberg et al. | |
| 7,276,078 B2 | 10/2007 | Spenser et al. | |
| 7,278,964 B2 | 10/2007 | Alferness | |
| 7,296,577 B2 | 11/2007 | Lashinski et al. | |
| 7,311,728 B2 | 12/2007 | Solem et al. | |
| 7,326,174 B2 | 2/2008 | Cox et al. | |
| 7,351,200 B2 | 4/2008 | Alferness | |
| 7,351,259 B2 | 4/2008 | Swinford et al. | |
| 7,351,260 B2 | 4/2008 | Nieminen et al. | |
| 7,361,137 B2 | 4/2008 | Taylor et al. | |
| 7,371,259 B2 | 5/2008 | Ryan et al. | |
| 7,373,207 B2 | 5/2008 | Lattouf | |
| 7,377,940 B2 | 5/2008 | Ryan et al. | |
| 7,381,182 B2 | 6/2008 | Raman et al. | |
| 7,381,210 B2 | 6/2008 | Zarbatany et al. | |
| 7,381,220 B2 | 6/2008 | Macoviak et al. | |
| 7,390,293 B2 | 6/2008 | Jayaraman | |
| 7,410,461 B2 | 8/2008 | Lau et al. | |
| 7,419,466 B2 | 9/2008 | Vanden Hoek et al. | |
| 2001/0003986 A1 | 6/2001 | Cosgrove | |
| 2001/0005787 A1 | 6/2001 | Oz et al. | |
| 2001/0009976 A1 | 7/2001 | Panescu et al. | |
| 2001/0014800 A1 | 8/2001 | Frazier et al. | |
| 2001/0014811 A1 | 8/2001 | Hussein | |
| 2001/0018611 A1 | 8/2001 | Solem et al. | |
| 2001/0021874 A1 | 9/2001 | Carpentier et al. | |
| 2001/0029314 A1 | 10/2001 | Alferness et al. | |
| 2001/0034551 A1 | 10/2001 | Cox | |
| 2001/0037123 A1 | 11/2001 | Hancock | |
| 2001/0039434 A1 | 11/2001 | Frazier et al. | |
| 2001/0039435 A1 | 11/2001 | Roue et al. | |
| 2001/0039436 A1 | 11/2001 | Frazier et al. | |
| 2001/0041821 A1 | 11/2001 | Wilk | |
| 2001/0041914 A1 | 11/2001 | Frazier et al. | |
| 2001/0041915 A1 | 11/2001 | Roue et al. | |
| 2001/0044568 A1 | 11/2001 | Langberg et al. | |
| 2001/0047122 A1 | 11/2001 | Vanden Hoek et al. | |
| 2001/0049492 A1 | 12/2001 | Frazier et al. | |
| 2002/0007216 A1 | 1/2002 | Melvin | |
| 2002/0013571 A1 | 1/2002 | Goldfarb et al. | |
| 2002/0016628 A1 | 2/2002 | Langberg et al. | |
| 2002/0019580 A1 | 2/2002 | Lau et al. | |
| 2002/0022880 A1 | 2/2002 | Melvin | |
| 2002/0026092 A1 | 2/2002 | Buckberg et al. | |
| 2002/0028981 A1 | 3/2002 | Lau et al. | |
| 2002/0029783 A1 | 3/2002 | Stevens et al. | |
| 2002/0032364 A1 | 3/2002 | Lau et al. | |
| 2002/0042554 A1 | 4/2002 | Alferness et al. | |
| 2002/0045798 A1 | 4/2002 | Lau et al. | |
| 2002/0045799 A1 | 4/2002 | Lau et al. | |
| 2002/0045800 A1 | 4/2002 | Lau et al. | |
| 2002/0052538 A1 | 5/2002 | Lau et al. | |
| 2002/0056461 A1 | 5/2002 | Jayaraman | |
| 2002/0058855 A1 | 5/2002 | Schweich, Jr. et al. | |
| 2002/0065449 A1 | 5/2002 | Wardle | |
| 2002/0065465 A1 | 5/2002 | Panescu et al. | |
| 2002/0065554 A1 | 5/2002 | Streeter | |
| 2002/0068850 A1 | 6/2002 | Vanden Hoek et al. | |
| 2002/0077532 A1 | 6/2002 | Gannoe et al. | |
| 2002/0082647 A1 | 6/2002 | Alferness et al. | |
| 2002/0087173 A1 | 7/2002 | Alferness et al. | |
| 2002/0091296 A1 | 7/2002 | Alferness | |
| 2002/0103511 A1 | 8/2002 | Alferness et al. | |
| 2002/0103532 A1 | 8/2002 | Langberg et al. | |
| 2002/0103533 A1 | 8/2002 | Langberg et al. | |
| 2002/0111533 A1 | 8/2002 | Melvin | |
| 2002/0111567 A1 | 8/2002 | Vanden Hoek et al. | |
| 2002/0111636 A1 | 8/2002 | Fleischman et al. | |
| 2002/0133055 A1 | 9/2002 | Haindl | |
| 2002/0143250 A1 | 10/2002 | Panescu et al. | |
| 2002/0151766 A1 | 10/2002 | Shapland et al. | |
| 2002/0151961 A1 | 10/2002 | Lashinski et al. | |
| 2002/0161275 A1 | 10/2002 | Schweich, Jr. et al. | |
| 2002/0169358 A1 | 11/2002 | Mortier et al. | |
| 2002/0169359 A1 | 11/2002 | McCarthy et al. | |
| 2002/0169360 A1 | 11/2002 | Taylor et al. | |
| 2002/0169502 A1 | 11/2002 | Mathis | |
| 2002/0169504 A1 | 11/2002 | Alferness et al. | |
| 2002/0173694 A1 | 11/2002 | Mortier et al. | |
| 2002/0183835 A1 | 12/2002 | Taylor et al. | |
| 2002/0183836 A1 | 12/2002 | Liddicoat et al. | |
| 2002/0183837 A1 | 12/2002 | Streeter et al. | |
| 2002/0183838 A1 | 12/2002 | Liddicoat et al. | |
| 2002/0183841 A1 | 12/2002 | Cohn et al. | |
| 2002/0188170 A1 | 12/2002 | Santamore et al. | |
| 2002/0188350 A1 | 12/2002 | Arru et al. | |
| 2003/0004396 A1 | 1/2003 | Vanden Hock et al. | |
| 2003/0009081 A1 | 1/2003 | Rogers et al. | |
| 2003/0023132 A1 | 1/2003 | Melvin et al. | |
| 2003/0028077 A1 | 2/2003 | Alferness et al. | |
| 2003/0032979 A1 | 2/2003 | Mortier et al. | |
| 2003/0045771 A1 | 3/2003 | Schweich, Jr. et al. | |
| 2003/0045776 A1 | 3/2003 | Alferness et al. | |
| 2003/0045896 A1 | 3/2003 | Murphy et al. | |
| 2003/0050529 A1 | 3/2003 | Vidlund et al. | |
| 2003/0050659 A1 | 3/2003 | Murphy et al. | |
| 2003/0055336 A1 * | 3/2003 | Buck et al. | 600/453 |
| 2003/0060674 A1 | 3/2003 | Gifford, III et al. | |
| 2003/0065248 A1 | 4/2003 | Lau et al. | |
| 2003/0069467 A1 | 4/2003 | Lau et al. | |
| 2003/0078465 A1 | 4/2003 | Pai et al. | |
| 2003/0078653 A1 | 4/2003 | Vesely et al. | |
| 2003/0078671 A1 | 4/2003 | Lesniak et al. | |
| 2003/0093104 A1 | 5/2003 | Bonner et al. | |
| 2003/0105519 A1 | 6/2003 | Fasol et al. | |
| 2003/0120340 A1 | 6/2003 | Liska et al. | |
| 2003/0130730 A1 | 7/2003 | Cohn et al. | |
| 2003/0130731 A1 | 7/2003 | Vidlund et al. | |
| 2003/0144697 A1 | 7/2003 | Mathis et al. | |
| 2003/0149333 A1 | 8/2003 | Alferness | |

(56) References Cited

U.S. PATENT DOCUMENTS

| | | |
|---|---|---|
| 2003/0153946 A1 | 8/2003 | Kimblad |
| 2003/0158570 A1 | 8/2003 | Ferrazzi |
| 2003/0166992 A1 | 9/2003 | Schweich, Jr. et al. |
| 2003/0171641 A1 | 9/2003 | Schweich, Jr. et al. |
| 2003/0171776 A1 | 9/2003 | Adams et al. |
| 2003/0171806 A1 | 9/2003 | Mathis et al. |
| 2003/0181928 A1 | 9/2003 | Vidlund et al. |
| 2003/0191538 A1 | 10/2003 | Buckberg et al. |
| 2003/0199733 A1 | 10/2003 | Shapland et al. |
| 2003/0212453 A1 | 11/2003 | Mathis et al. |
| 2003/0225454 A1 | 12/2003 | Mathis et al. |
| 2003/0229260 A1 | 12/2003 | Girard et al. |
| 2003/0229261 A1 | 12/2003 | Girard et al. |
| 2003/0229265 A1 | 12/2003 | Girard et al. |
| 2003/0229266 A1 | 12/2003 | Cox et al. |
| 2003/0233022 A1 | 12/2003 | Vidlund et al. |
| 2003/0233142 A1 | 12/2003 | Morales et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015039 A1 | 1/2004 | Melvin |
| 2004/0015040 A1 | 1/2004 | Melvin |
| 2004/0015041 A1 | 1/2004 | Melvin |
| 2004/0019377 A1 | 1/2004 | Taylor et al. |
| 2004/0019378 A1 | 1/2004 | Hlavka et al. |
| 2004/0024286 A1 | 2/2004 | Melvin |
| 2004/0030382 A1 | 2/2004 | St. Goar et al. |
| 2004/0034271 A1 | 2/2004 | Melvin et al. |
| 2004/0039442 A1 | 2/2004 | St. Goar et al. |
| 2004/0039443 A1 | 2/2004 | Solem et al. |
| 2004/0044365 A1 | 3/2004 | Bachman |
| 2004/0049115 A1 | 3/2004 | Murphy et al. |
| 2004/0049116 A1 | 3/2004 | Murphy et al. |
| 2004/0059180 A1 | 3/2004 | Melvin |
| 2004/0059181 A1 | 3/2004 | Alferness |
| 2004/0059182 A1 | 3/2004 | Alferness |
| 2004/0059187 A1 | 3/2004 | Alferness |
| 2004/0059188 A1 | 3/2004 | Alferness |
| 2004/0059189 A1 | 3/2004 | Alferness |
| 2004/0059351 A1 | 3/2004 | Eigler et al. |
| 2004/0064014 A1 | 4/2004 | Melvin et al. |
| 2004/0073302 A1 | 4/2004 | Rourke et al. |
| 2004/0092962 A1 | 5/2004 | Thornton et al. |
| 2004/0093023 A1 | 5/2004 | Allen et al. |
| 2004/0098116 A1 | 5/2004 | Callas et al. |
| 2004/0102678 A1 | 5/2004 | Haindl |
| 2004/0102679 A1 | 5/2004 | Alferness et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0111101 A1 | 6/2004 | Chin |
| 2004/0122448 A1 | 6/2004 | Levine |
| 2004/0122512 A1 | 6/2004 | Navia et al. |
| 2004/0122513 A1 | 6/2004 | Navia et al. |
| 2004/0127980 A1 | 7/2004 | Kowalsky et al. |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133069 A1 | 7/2004 | Shapland et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138526 A1 | 7/2004 | Guenst |
| 2004/0138744 A1 | 7/2004 | Lashinski et al. |
| 2004/0143323 A1 | 7/2004 | Chawla |
| 2004/0148019 A1 | 7/2004 | Vidlund et al. |
| 2004/0148020 A1 | 7/2004 | Vidlund et al. |
| 2004/0152947 A1 | 8/2004 | Schroeder et al. |
| 2004/0158123 A1 | 8/2004 | Jayaraman |
| 2004/0158321 A1 | 8/2004 | Reuter et al. |
| 2004/0162610 A1 | 8/2004 | Liska et al. |
| 2004/0167374 A1 | 8/2004 | Schweich et al. |
| 2004/0167539 A1 | 8/2004 | Kuehn et al. |
| 2004/0171907 A1 | 9/2004 | Alferness et al. |
| 2004/0171908 A1 | 9/2004 | Alferness et al. |
| 2004/0171909 A1 | 9/2004 | Alferness |
| 2004/0172046 A1 | 9/2004 | Hlavka et al. |
| 2004/0176678 A1 | 9/2004 | Murphy et al. |
| 2004/0176679 A1 | 9/2004 | Murphy et al. |
| 2004/0176840 A1 | 9/2004 | Langberg et al. |
| 2004/0181121 A1 | 9/2004 | Alferness et al. |
| 2004/0181122 A1 | 9/2004 | Alferness et al. |
| 2004/0181123 A1 | 9/2004 | Alferness et al. |
| 2004/0181124 A1 | 9/2004 | Alferness |
| 2004/0181125 A1 | 9/2004 | Alferness et al. |
| 2004/0181126 A1 | 9/2004 | Buckberg et al. |
| 2004/0181238 A1 | 9/2004 | Zarbatany et al. |
| 2004/0186342 A1 | 9/2004 | Vanden Hock et al. |
| 2004/0186566 A1 | 9/2004 | Hindrichs et al. |
| 2004/0193191 A1 | 9/2004 | Starksen et al. |
| 2004/0193260 A1 | 9/2004 | Alferness et al. |
| 2004/0199183 A1 | 10/2004 | Oz et al. |
| 2004/0206363 A1 | 10/2004 | McCarthy et al. |
| 2004/0210240 A1 | 10/2004 | Saint |
| 2004/0210303 A1 | 10/2004 | Sedransk |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0220593 A1 | 11/2004 | Greenhalgh |
| 2004/0225300 A1 | 11/2004 | Goldfarb et al. |
| 2004/0243227 A1 | 12/2004 | Starksen et al. |
| 2004/0243228 A1 | 12/2004 | Kowalsky et al. |
| 2004/0243229 A1 | 12/2004 | Vidlund et al. |
| 2004/0249452 A1 | 12/2004 | Adams et al. |
| 2004/0254600 A1 | 12/2004 | Zarbatany et al. |
| 2004/0260317 A1 | 12/2004 | Bloom et al. |
| 2004/0260393 A1 | 12/2004 | Rahdert et al. |
| 2004/0267083 A1 | 12/2004 | McCarthy et al. |
| 2004/0267329 A1 | 12/2004 | Raman et al. |
| 2004/0267358 A1 | 12/2004 | Reitan |
| 2005/0004428 A1 | 1/2005 | Cox et al. |
| 2005/0004665 A1 | 1/2005 | Aklog |
| 2005/0004666 A1 | 1/2005 | Alfieri et al. |
| 2005/0004667 A1 | 1/2005 | Swinford et al. |
| 2005/0004668 A1 | 1/2005 | Aklog et al. |
| 2005/0010240 A1 | 1/2005 | Mathis et al. |
| 2005/0010283 A1 | 1/2005 | Vijay |
| 2005/0010286 A1 | 1/2005 | Vijay |
| 2005/0021056 A1 | 1/2005 | St. Goar et al. |
| 2005/0021057 A1 | 1/2005 | St. Goar et al. |
| 2005/0021121 A1 | 1/2005 | Reuter et al. |
| 2005/0021135 A1 | 1/2005 | Ryan et al. |
| 2005/0027351 A1 | 2/2005 | Reuter et al. |
| 2005/0027353 A1 | 2/2005 | Alferness et al. |
| 2005/0027369 A1 | 2/2005 | Eldridge et al. |
| 2005/0033419 A1 | 2/2005 | Alferness et al. |
| 2005/0033446 A1 | 2/2005 | Deem et al. |
| 2005/0038506 A1 | 2/2005 | Webler et al. |
| 2005/0038507 A1 | 2/2005 | Alferness et al. |
| 2005/0038509 A1 | 2/2005 | Ashe |
| 2005/0043792 A1 | 2/2005 | Solem et al. |
| 2005/0049679 A1 | 3/2005 | Taylor et al. |
| 2005/0049698 A1 | 3/2005 | Bolling et al. |
| 2005/0055087 A1 | 3/2005 | Starksen |
| 2005/0055089 A1 | 3/2005 | Macoviak et al. |
| 2005/0059854 A1 | 3/2005 | Vanden Hoek et al. |
| 2005/0060030 A1 | 3/2005 | Lashinski et al. |
| 2005/0065550 A1 | 3/2005 | Starksen et al. |
| 2005/0065598 A1 | 3/2005 | Mathis et al. |
| 2005/0065601 A1 | 3/2005 | Lee et al. |
| 2005/0070998 A1 | 3/2005 | Rourke et al. |
| 2005/0071000 A1 | 3/2005 | Liddicoat et al. |
| 2005/0075723 A1 | 4/2005 | Schroeder et al. |
| 2005/0075727 A1 | 4/2005 | Wheatley |
| 2005/0080402 A1 | 4/2005 | Santamore et al. |
| 2005/0080483 A1 | 4/2005 | Solem et al. |
| 2005/0085688 A1 | 4/2005 | Girard et al. |
| 2005/0095268 A1 | 5/2005 | Walsh et al. |
| 2005/0096666 A1 | 5/2005 | Gordon et al. |
| 2005/0096740 A1 | 5/2005 | Langberg et al. |
| 2005/0107810 A1 | 5/2005 | Morales et al. |

(56) References Cited

U.S. PATENT DOCUMENTS

| | | |
|---|---|---|
| 2005/0107811 A1 | 5/2005 | Starksen et al. |
| 2005/0107812 A1 | 5/2005 | Starksen et al. |
| 2005/0113635 A1 | 5/2005 | Whayne et al. |
| 2005/0113811 A1 | 5/2005 | Houser et al. |
| 2005/0119519 A9 | 6/2005 | Girard et al. |
| 2005/0131533 A1 | 6/2005 | Alfier et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0137700 A1 | 6/2005 | Spence et al. |
| 2005/0143811 A1 | 6/2005 | Realyvasquez |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0159810 A1 | 7/2005 | Filsoufi |
| 2005/0177228 A1 | 8/2005 | Solem et al. |
| 2005/0184122 A1 | 8/2005 | Hlavka et al. |
| 2005/0187619 A1 | 8/2005 | Mathis et al. |
| 2005/0192474 A1 | 9/2005 | Vanden Hoek et al. |
| 2005/0192666 A1 | 9/2005 | McCarthy |
| 2005/0197527 A1 | 9/2005 | Bolling |
| 2005/0197528 A1 | 9/2005 | Vanden Hoek et al. |
| 2005/0197692 A1 | 9/2005 | Pai et al. |
| 2005/0197693 A1 | 9/2005 | Pai et al. |
| 2005/0209690 A1 | 9/2005 | Mathis et al. |
| 2005/0216039 A1 | 9/2005 | Lederman |
| 2005/0216077 A1 | 9/2005 | Mathis et al. |
| 2005/0216078 A1 | 9/2005 | Starksen et al. |
| 2005/0222488 A1 | 10/2005 | Chang et al. |
| 2005/0222489 A1 | 10/2005 | Rahdert et al. |
| 2005/0222678 A1 | 10/2005 | Lashinski et al. |
| 2005/0228217 A1 | 10/2005 | Alferness et al. |
| 2005/0228422 A1 | 10/2005 | Machold et al. |
| 2005/0240200 A1 | 10/2005 | Bergheim |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0261704 A1 | 11/2005 | Mathis et al. |
| 2005/0267574 A1 | 12/2005 | Cohn et al. |
| 2005/0272969 A1 | 12/2005 | Alferness et al. |
| 2005/0278022 A1 | 12/2005 | Lim |
| 2006/0004443 A1 | 1/2006 | Liddicoat et al. |
| 2006/0009842 A1 | 1/2006 | Huynh et al. |
| 2006/0030885 A1 | 2/2006 | Hyde |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0069430 A9 | 3/2006 | Rahdert et al. |
| 2006/0100699 A1 | 5/2006 | Vidlund et al. |
| 2006/0106456 A9 | 5/2006 | Machold et al. |
| 2006/0111607 A1 | 5/2006 | Alferness et al. |
| 2006/0116756 A1 | 6/2006 | Solem et al. |
| 2006/0116757 A1 | 6/2006 | Lashinski et al. |
| 2006/0149122 A1 | 7/2006 | Shapland et al. |
| 2006/0149123 A1 | 7/2006 | Vidlund et al. |
| 2006/0149368 A1 | 7/2006 | Spence |
| 2006/0155165 A1 | 7/2006 | Vanden Hoek et al. |
| 2006/0161040 A1 | 7/2006 | McCarthy et al. |
| 2006/0195012 A1 | 8/2006 | Mortier et al. |
| 2006/0212114 A1 | 9/2006 | Menicanti et al. |
| 2006/0235265 A1 | 10/2006 | Alferness et al. |
| 2006/0241340 A1 | 10/2006 | Schroeder et al. |
| 2006/0247492 A1 | 11/2006 | Streeter |
| 2006/0252984 A1 | 11/2006 | Rahdert et al. |
| 2006/0258900 A1 | 11/2006 | Buckberg et al. |
| 2007/0004962 A1 | 1/2007 | Alferness et al. |
| 2007/0038293 A1 | 2/2007 | St.Goar et al. |
| 2007/0050020 A1 | 3/2007 | Spence |
| 2007/0055303 A1 | 3/2007 | Vidlund et al. |
| 2007/0100442 A1 | 5/2007 | Solem et al. |
| 2007/0112244 A1 | 5/2007 | McCarthy et al. |
| 2007/0118155 A1 | 5/2007 | Goldfarb et al. |
| 2007/0129737 A1 | 6/2007 | Goldfarb et al. |
| 2007/0161846 A1 | 7/2007 | Nikolic et al. |
| 2007/0208211 A1 | 9/2007 | Shapland et al. |
| 2007/0225547 A1 | 9/2007 | Alferness |
| 2007/0288090 A1 | 12/2007 | Solem et al. |
| 2008/0033235 A1 | 2/2008 | Shapland et al. |
| 2008/0051807 A1 | 2/2008 | St. Goar et al. |
| 2008/0091191 A1 | 4/2008 | Witzel et al. |
| 2008/0125622 A1 | 5/2008 | Walsh et al. |
| 2008/0161638 A1 | 7/2008 | Taylor et al. |
| 2008/0167714 A1 | 7/2008 | St. Goar et al. |
| 2008/0183194 A1 | 7/2008 | Goldfarb et al. |

FOREIGN PATENT DOCUMENTS

| | | |
|---|---|---|
| DE | 42 34 127 A1 | 5/1994 |
| DE | 295 00 381 U1 | 7/1995 |
| DE | 296 19 294 U1 | 8/1997 |
| DE | 198 26 675 A1 | 3/1999 |
| DE | 199 47 885 A1 | 4/2000 |
| DE | 298 24 017 U1 | 5/2000 |
| EP | 0 583 012 A1 | 2/1994 |
| EP | 0 792 621 A1 | 9/1997 |
| EP | 0 820 729 A1 | 1/1998 |
| EP | 1 129 736 A1 | 9/2001 |
| GB | 2214428 | 9/1989 |
| NL | 9 200 878 | 12/1993 |
| WO | WO 91/19465 A1 | 12/1991 |
| WO | WO 95/06447 A1 | 3/1995 |
| WO | WO 95/16407 A1 | 6/1995 |
| WO | WO 95/16476 A1 | 6/1995 |
| WO | WO 96/02197 A1 | 2/1996 |
| WO | WO 96/04852 A1 | 2/1996 |
| WO | WO 96/40356 A1 | 12/1996 |
| WO | WO 97/14286 A2 | 4/1997 |
| WO | WO 97/24082 A1 | 7/1997 |
| WO | WO 97/24083 A1 | 7/1997 |
| WO | WO 97/24101 A1 | 7/1997 |
| WO | WO 97/41779 A1 | 11/1997 |
| WO | WO 98/03213 A1 | 1/1998 |
| WO | WO 98/14136 A1 | 4/1998 |
| WO | WO 98/17347 A1 | 4/1998 |
| WO | WO 98/18393 A1 | 5/1998 |
| WO | WO 98/26738 A1 | 6/1998 |
| WO | WO 98/29041 A1 | 7/1998 |
| WO | WO 98/32382 A1 | 7/1998 |
| WO | WO 98/44969 A1 | 10/1998 |
| WO | WO 98/58598 A1 | 12/1998 |
| WO | WO 99/00059 A1 | 1/1999 |
| WO | WO 99/11201 A2 | 3/1999 |
| WO | WO 99/13777 A1 | 3/1999 |
| WO | WO 99/13936 A1 | 3/1999 |
| WO | WO 99/16350 A1 | 4/1999 |
| WO | WO 99/22784 A1 | 5/1999 |
| WO | WO 99/30647 A1 | 6/1999 |
| WO | WO 99/44534 A1 | 9/1999 |
| WO | WO 99/44680 A1 | 9/1999 |
| WO | WO 99/52470 A1 | 10/1999 |
| WO | WO 99/53977 A1 | 10/1999 |
| WO | WO 99/56655 A1 | 11/1999 |
| WO | WO 99/66969 A1 | 12/1999 |
| WO | WO 00/02500 A1 | 1/2000 |
| WO | WO 00/03759 A2 | 1/2000 |
| WO | WO 00/06026 A2 | 2/2000 |
| WO | WO 00/06028 A1 | 2/2000 |
| WO | WO 00/13722 A1 | 3/2000 |
| WO | WO 00/18320 A1 | 4/2000 |
| WO | WO 00/25842 A1 | 5/2000 |
| WO | WO 00/25853 A2 | 5/2000 |
| WO | WO 00/27304 A1 | 5/2000 |
| WO | WO 00/28912 A1 | 5/2000 |
| WO | WO 00/28918 A1 | 5/2000 |
| WO | WO 00/36995 A2 | 6/2000 |
| WO | WO 00/42919 A1 | 7/2000 |
| WO | WO 00/42950 A2 | 7/2000 |
| WO | WO 00/42951 A1 | 7/2000 |
| WO | WO 00/45735 A1 | 8/2000 |

(56) References Cited

FOREIGN PATENT DOCUMENTS

| WO | WO 00/60995 A2 | 10/2000 |
|---|---|---|
| WO | WO 00/61033 A1 | 10/2000 |
| WO | WO 00/62715 A1 | 10/2000 |
| WO | WO 00/62727 A1 | 10/2000 |
| WO | WO 01/00111 A1 | 1/2001 |
| WO | WO 01/03608 A1 | 1/2001 |
| WO | WO 01/19291 A1 | 3/2001 |
| WO | WO 01/19292 A1 | 3/2001 |
| WO | WO 01/21070 A1 | 3/2001 |
| WO | WO 01/21098 A1 | 3/2001 |
| WO | WO 01/21099 A1 | 3/2001 |
| WO | WO 01/21247 A1 | 3/2001 |
| WO | WO 01/26557 A1 | 4/2001 |
| WO | WO 01/28432 A1 | 4/2001 |
| WO | WO 01/49217 A2 | 7/2001 |
| WO | WO 01/50981 A1 | 7/2001 |
| WO | WO 01/54562 A2 | 8/2001 |
| WO | WO 01/54618 A1 | 8/2001 |
| WO | WO 01/54745 A2 | 8/2001 |
| WO | WO 01/67985 A1 | 9/2001 |
| WO | WO 01/70116 A1 | 9/2001 |
| WO | WO 01/78625 A1 | 10/2001 |
| WO | WO 01/85061 A2 | 11/2001 |
| WO | WO 01/91667 A2 | 12/2001 |
| WO | WO 01/95830 A2 | 12/2001 |
| WO | WO 01/95831 A2 | 12/2001 |
| WO | WO 01/95832 A1 | 12/2001 |
| WO | WO 02/11625 A2 | 2/2002 |
| WO | WO 02/13726 A2 | 2/2002 |
| WO | WO 02/19917 A1 | 3/2002 |
| WO | WO 02/28450 A2 | 4/2002 |
| WO | WO 02/30292 A1 | 4/2002 |
| WO | WO 02/30335 A2 | 4/2002 |
| WO | WO 02/34167 A2 | 5/2002 |
| WO | WO 02/38081 A2 | 5/2002 |
| WO | WO 02/43617 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/064035 A1 | 8/2002 |
| WO | WO 02/076284 A2 | 10/2002 |
| WO | WO 02/078576 A2 | 10/2002 |
| WO | WO 02/085251 A1 | 10/2002 |
| WO | WO 02/096275 A2 | 12/2002 |
| WO | WO 03/001893 A2 | 1/2003 |
| WO | WO 03/007778 A2 | 1/2003 |
| WO | WO 03/015611 A2 | 2/2003 |
| WO | WO 03/022131 A2 | 3/2003 |
| WO | WO 03/059209 A2 | 7/2003 |
| WO | WO 03/066147 A1 | 8/2003 |

OTHER PUBLICATIONS

McGoon, M.D. et al., "Correction of the univentricular heart having two atrioventricular valves," *The Journal of Thoracic and Cardiovascular Surgery*, vol. 74, No. 2, Aug. 1977, pp. 218-226.

Lev, M.D., et al., "Single (Primitive) Ventricle," *Circulation*, vol. 39, May 1969, pp. 577-591.

Westaby with Bosher, "Landmarks in Cardiac Surgery," 1997, pp. 198-199.

Shumacker, "Cardiac Aneurysms," *The Evolution of Cardiac Surgery*, 1992, pp. 159-165.

Feldt, M.D., "Current status of the septation procedure for univentricular heart," *The Journal of Thoracic and Cardiovascular Surgery*, vol. 82, No. 1, Jul. 1981, pp. 93-97.

Doty, M.D., "Septation of the univentricular heart," *The Journal of Thoracic and Cardiovascular Surgery*, vol. 78, No. 3, Sep. 1979, pp. 423-430.

Carpentier et al., "Myocardial Substitution with a Stimulated Skeletal Muscle: First Successful Clinical Case," Letter to the Editor, p. 1267, Sep. 25, 1996.

Ianuzzo et al., "Preservation of the Latissimus Dorsi Muscle During Cardiomyoplasty Surgery," *J. Card. Surg.*, 1996:11:99-108.

Ianuzzo et al., "On Preconditioning of Skeletal Muscle: Application to Dynamic Cardiomyoplasty," Invited Commentary, *J. Card. Surg.*, 1996:11:109-110.

Chachques et al., "Latissimus Dorsi Dynamic Cardiomyoplasty," *Ann. Thorac. Surg.*, 1989:47:600-604.

Moreira et al., "Latissimus Dorsi Cardiomyoplasty in the Treatment of Patients with Dilated Cardiomyopathy," Supplement IV Circulation, Sep. 25, 1996, 7 pgs.

Lucas et al., "Long-Term Follow-Up (12 to 35 Weeks) After Dynamic Cardiomyoplasty," *JACC*, vol. 22, No. 3, Sep. 1993:758-67.

Batista et al., "Partial Left Ventriculectomy to Improve Left Ventricular Function in End-Stage Heart Disease," *J. Card. Surg.*, 1996:11:96-98.

"Congestive Heart Failure in the United States: A New Epidemic" Data Fact Sheet, National Heart, Lung, and Blood Institute, National Institutes of Health, Dec. 9, 1996, pp. 1-6.

Kormos et al., "Experience with Univentricular Support in Mortally III Cardiac Transplant Candidates," *Ann. Thorac. Surg.*, 1990:49:261-71.

Wampler et al., "Treatment of Cardiogenic Shock with the Hemopump Left Ventricular Assist Device," *Ann. Thorac. Surg.*, 1991:52:506-13.

McCarthy et al., "Clinical Experience with the Novacor Ventricular Assist System," *J. Thorac. Cardiovasc. Surg.*, 1991:102-578-87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.

Bearnson et al., "Development of a Prototype Magnetically Suspended Rotor Ventricular Assist Device," *ASAIO Journal*, 1996, pp. 275-280.

Sakakibara et al., "A Muscle Powered Cardiac Assist Device for Right Ventricular Support: Total Assist or Partial Assist?," *Trans. Am. Soc. Artif. Intern. Organs*, vol. XXXVI, 1990, pp. 372-375.

Medtronic, Inc. 1996 Annual Shareholders Report, 79 pages.

ABOIMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, ABIOMED's Temporary Artificial Heart System Reaches 200 U.S. Medical Center Milestone, 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED Wins NIH Grant to Develop Calcification-Resistant Plastic Heart Valve," 1 page.

Press Release dated Aug. 25, 1995, "ABIOMED Wins Research Grant from NIH to Develop Suturing Instrument for Abdominal surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

(56) References Cited

OTHER PUBLICATIONS

Press Release dated Apr. 27, 1995, "ABIOMED's Temporary Artificial Heart System Reaches 1,000 Patient Milestone; BVS-5000 in More Than 100 U.S. Medical Centers," 1 page.
"Reversible Cardiomyopathy," *Thoratec's Heartbeat*, vol. 10.2, Aug. 1996, 4 pages.
Tsai et al., "Surface Modifying Additives for Improved Device-Blood Compatibility," *ASAIO Journal*, 1994, pp. 619-624.
Farrar et al., "A New Skeletal Muscle Linear-Pull Energy Convertor as a Power Source for Prosthetic Support Devices," *The Journal of Heart & Lung Transplantation*, vol. 11, No. 5, Sep. 1992, pp. 341-349.
Brochure entitled "Thoratec Ventricular Assist Device System—Because Heart Patients Come in All Sizes," date even with or prior to Jan. 2, 1997, 5 pages.
Press Release dated Oct. 3, 1994, "Heartmate System Becomes First Implantable Cardiac-Assist Device to be Approved for Commercial Sale in the U.S.," 2 pages.
Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.
Bach et al., "Early Improvement in Congestive Heart Failure after Correction of Secondary Mitral Regurgitation in End-Stage Cardiomyopathy," *American Heart Journal*, Jun. 1995, pp. 1165-1170.
Schuler et al., "Temporal Response of Left Ventricular Performance to Mitral Valve Surgery," vol. 59, No. 6, Jun. 1979, pp. 1218-1231.
Huikuri, "Effect of Mitral Valve Replacement on Left Ventricular Function in Mitral Regurgitation," *Br. Heart J.*, vol. 49, 1983, pp. 328-333.
Pitarys II et al., "Long-Term Effects of Excision of the Mitral Apparatus on Global and Regional Ventricular Function in Humans," *JACC*, vol. 15, No. 3, Mar. 1, 1990, pp. 557-563.
Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683.
Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146.
Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.
McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.
Alonso-Lej, M.D., "Adjustable Annuloplasty for Tricuspid Insufficiency," *The Annals of Thoracic Surgery*, vol. 46, No. 3, Sep. 1988, 2 pages.
Kurlansky et al., "Adjustable Annuloplasty for Tricuspid Insufficiency," *Ann. Thorac. Surg.*, 44:404-406, Oct. 1987.
Savage, M.D., "Repair of left ventricular aneurysm," *The Journal of Thoracic and Cardiovascular Surgery*, vol. 104, No. 3, Sep. 1992, pp. 752-762.
Melvin, "Ventricular Radius Reduction Without Resection: A Computational Analysis," *ASAIO Journal*, 45:160-165, 1999.
Cox, "Left Ventricular Aneurysms: Pathophysiologic Observations and Standard Resection," *Seminars in Thoracic and Cardiovascular Surgery*, vol. 9, No. 2, Apr. 1997, pp. 113-122.
Boyd et al., "Tricuspid Annuloplasty," *The Journal of Thoracic Cardiovascular Surgery*, vol. 68, No. 3, Sep. 1974, 8 pages.
Melvin, "Reduction of Ventricular Wall Tensile Stress by Geometric Remodeling Device", 1 page, undated.
Kay et al., "Surgical Treatment of Mitral Insufficiency", *The Journal of Thoracic Surgery*, 1955, 29:618-620.
Harken et al., "The Surgical Correction of Mitral Insufficiency", *The Journal of Thoracic Surgery*, 1954, 28:604-627.
Bailey et al., "Closed Intracardiac Tactile Surgery", *Diseases of the Chest*, 1952, XXII:1-24.
Sakakibara, "A Surgical Approach to the Correction of Mitral Insufficiency", *Annals of Surgery*, 1955, 142:196-203.
Glenn et al., "The Surgical Treatment of Mitral Insufficiency: The Fate of a Vascularized Transchamber Intracardiac Graft", *Annals of Surgery*, 1955, 141:4:510-518.
Kay et al., "Surgical Treatment of Mitral Insufficiency", *Surgery*, 1955, 37:5:697-706.
Bailey et al., "The Surgical Correction of Mitral Insufficiency by the Use of Pericardial Grafts", *The Journal of Thoracic Surgery*, 1954, 28:6:551-603.
Harken et al., "The Surgical Correction of Mitral Insufficency", *Surgical Forum*, 1953, 4:4-7.
Shumacker, Jr., "Attempts to Control Mitral Regurgitation", *The Evolution of Cardiac Surgery*, 1992, 203-210.
Acorn cardiovascular, inc., "Acorn Cardiovascular Summary", undated.
Acorn cardiovascular, inc., "Acorn Cardiovascular Company Overview", undated.
Batista, MD et al., "Partial Left Ventriculectomy to Treat End-Stage Heart Disease" *Ann. Thorac. Surg.*, 64:634-8, 1997.
Melvin DB et al., Reduction of Ventricular Wall Tensile Stress by Geometric Remodeling Device, *Poster text, ASAIO* 1999.
Hayden et al., "Scintiphotographic Studies of Acquired Cardiovascular Disease," *Seminars in Nuclear Medicine*, vol. III, No. 2, Apr. 1973, pp. 177-190.
McCarthy, Transcription of Mar. 13, 2000 presentation given at ACC.
Acorn cardiovascular, inc., "Acorn Cardiovascular Abstracts", Nov. 13, 2000.
Nation's First "Heart Jacket" Surgery to Treat Heart Failure Performed at HUP: Novel "Cardiac Support Device Comes to America After Promising Results in Europe", Jun. 26, 2000.
Acorn cardiovascular, inc., Acorn Cardiovascular Company Overview, undated, 1 page.
Acorn cardiovascular, inc., Acorn Cardiovascular Company Overview, Jun. 2000.
Acorn cardiovascular, inc., Acorn Cardiovascular Business Plan, May 2000.
Acorn cardiovascular, inc., "Acorn Cardiovascular Highlights Abstracts", Mar. 10, 1999.
Acorn cardiovascular, inc., "Acorn Cardiovascular Highlights Abstracts", Apr. 19, 1999.
Acorn cardiovascular, inc., "Acorn Cardiovascular Highlights Abstracts", Oct. 1, 1999.
Acorn cardiovascular, inc., "Acorn Cardiovascular Highlights Abstracts", Nov. 9, 1999.
Melvin DB, "Ventricular Radius-Reduction Without Resection a Computational Assessment", undated.
Timek, Thomasz A., MD, et al, The Journal of Thoracic Surgery, vol. 123, No. 5 Surgery for Acquired Cardiovascular Disease, *Septal-lateral annular cinching abolishes acute ischemic mitral regurgitation*.
Timek, Thomasz A. et al, Department of Cardiothoracic Surgery and Division of Cardiovascular Medicine, Stanford University School of Medicine, Stanford, CA, *Septal-Lateral Annular Cinching ('SLAC') reduces Mitral Annular Size without Perturbing Normal Annular Dynamics*, 2002.
Hung, Judy MD et al., *Reverse Ventricular Remodeling Reduces Ischemic Mitral Regurgitation: Echo-Guided Device Application in the Beating Hear*, Circulation, www.circulationaha.org, Nov. 12, 2002.
Baim, Donald S., MD, Brigham and Women's Hospital, Harvard Medical School, *Percutaneous Treatment of Mitral Regurgitation*, 2005.
Dullum, Mercedes K.C., *Update on Restraint Devices for Congestive Heart Failure*, Abstract and presentation slides given at Tech-Con 2005 for Society of Thoracic Surgeons, Jan. 23, 2005, 11 pages.
"Heart 'jacket' could help stop heart failure progress," *Clinica*, Jul. 10, 2000.
McCarthy et al., "Device Based Left Ventricular Shape Change Immediately Reduces Left Ventricular vol. And Increases Ejection Fraction in a Pacing Induced Cardiomyopathy Model in Dogs: A Pilot Study," JACC, Feb. 2000.
Alonso-Lej, *The Journal of Thoracic and Cardiovascular Surgery*, vol. 68, No. 3, Sep. 1974, p. 349.

\* cited by examiner

METHODS AND DEVICES FOR IMPROVING MITRAL VALVE FUNCTION

This application is a continuation of application Ser. No. 10/840,511, filed May 7, 2004, now abandoned, of Richard SCHROEDER et al. for METHODS AND DEVICES FOR IMPROVING MITRAL VALVE FUNCTION, which is a continuation of application Ser. No. 10/762,513, filed Jan. 23, 2004, now abandoned, of Richard SCHROEDER et al. for METHODS AND DEVICES FOR IMPROVING MITRAL VALVE FUNCTION, which is a continuation of application Ser. No. 09/680,435, filed Oct. 6, 2000, now U.S. Pat. No. 6,723,038 of Richard SCHROEDER et al. for METHODS AND DEVICES FOR IMPROVING MITRAL VALVE FUNCTION, the complete disclosures of which are incorporated herein by reference.

BACKGROUND OF THE INVENTION

1. Field of the Invention

The present invention relates to devices and related methods for improving the function of heart valves, and more particularly to devices and related methods that passively assist in the apposition of heart valve leaflets to improve valve function of poorly functioning valves.

2. Description of the Related Art

Heart failure is a condition whereby the left ventricle becomes enlarged and dilated as a result of numerous etiologies. Initial causes of heart failure include chronic hypertension, myocardial infarction, mitral valve incompetency, and other dilated cardiomyopathies. With each of these conditions, the heart is forced to overexert itself in order to provide the cardiac output demanded from the body during its various demand states. The result is an enlarged left ventricle.

A dilated heart, and particularly a dilated left ventricle, can significantly increase the tension and/or stress in the heart wall both during diastolic filling and systolic contraction, which contributes to ongoing dilatation of the chamber. Prior treatments for heart failure include pharmacological treatments, assist devices such as pumps, and surgical treatments such as heart transplant, dynamic cardiomyoplasty, and the Batista partial left ventriculectomy. These prior treatments are described briefly in U.S. Pat. No. 5,961,440 to Schweich, Jr. et al., issued Oct. 5, 1999 and entitled "Heart Wall Tension Reduction Apparatus and Method," the complete disclosure of which is incorporated by reference herein.

A more recent concept for treating heart failure applies one or more splints onto the heart, and particularly the left ventricle, to reduce the myocardial muscular stresses encountered during pumping. Many examples of such approaches are disclosed in the incorporated U.S. Pat. No. 5,961,440. One example includes one or more transventricular splints placed across the left ventricle. Each splint may include a tension member extending across the ventricle and anchors disposed on opposite ends of the tension member and placed on the external surface of the heart.

Mitral valve incompetency or mitral valve regurgitation is a common comorbidity of congestive heart failure. As the dilation of the ventricle proceeds, valve function may worsen. The resultant volume overload condition, in turn, increases ventricular wall stress thereby advancing the dilation process, which may further worsen valve dysfunction.

In heart failure, the size of the valve annulus (particularly the mitral valve annulus) increases while the area of the leaflets of the valve remains constant. This may lead to an area of less coaptation of the valve leaflets, and, as a result, eventually to valve leakage. Moreover, in normal hearts, the annular size contracts during systole, aiding in valve coaptation. In heart failure, there is poor ventricular function and elevated wall stress. These effects tend to reduce annular contraction and distort annular size, often exacerbating mitral valve regurgitation. In addition, as the chamber dilates, the papillary muscles (to which the leaflets are connected via the chordae tendonae) may move radially outward and downward relative to the valve, and relative to their normal positions. During this movement of the papillary muscles, however, the various chordae lengths remain substantially constant, which limits the full closure ability of the leaflets by exerting tension prematurely on the leaflets. This condition is commonly referred to as "chordal tethering." The combination of annular changes and papillary changes results in a poorly functioning valve.

It has been observed that for at least certain placements, or orientations, of the one or more transventricular splints in humans, a pre-existing mitral valve incompetency can be exacerbated by the presence and impact of the tightened splints. The splints and the local deformation they impart may further alter the positions of the papillary muscles in such a way that the chordae do not allow as complete of a closure of the mitral valve, or that rotation of portions of the ventricular wall (to which additional chordae may be attached) may "tighten" one valve leaflet and "loosen" the other. In this manner, the leaflets may not close at the same level relative to the annulus, causing increased retrograde leakage through the valve.

Even in instances where the placement of splints does not contribute to further mitral valve leakage, it may be desirable to provide a therapy which could also correct the valve incompetency. A heart with even a small amount of regurgitation may benefit from not only the stress reducing functions of the ventricular splints as described above, but also from the elimination of the regurgitation, which will further off-load the pumping requirements of the myocardium.

While currently available methods of mitral valve repair or replacement are possible to employ in conjunction with ventricular splinting, they typically require opening the heart to gain direct access to the valve and its annulus. This type of access necessitates the use of cardiopulmonary bypass, which can introduce additional complications to the surgical procedure. Since the implantation of the splints themselves do not require the patient to be on cardiopulmonary bypass, it would be advantageous to devise a technique which could improve the mitral valve without the need for cardiopulmonary bypass. The ability to improve the mitral valve function without the need for cardiopulmonary bypass would be an advantage, both in conjunction with ventricular splinting, and also as a stand-alone therapy.

SUMMARY OF THE INVENTION

Objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. To achieve the objects and in accordance with the purpose of the invention, as embodied and broadly described herein, one aspect of the invention comprises a method for improving the function of a valve of a heart. The method includes the steps of placing an elongate member transverse a heart chamber so that each end of the elongate member extends through a wall of the heart, and placing first and second anchoring members external to the chamber. The first and second anchoring members are attached to first and second ends of the elongate member to fix the elongate member in a position across the chamber so as to reposition papillary muscles within the chamber.

According to another aspect, the invention comprises a method for improving the function of a valve of a heart. The method includes the steps of placing an elongate member transverse a heart chamber so that a first end of the elongate member extends through a wall of the heart between two papillary muscles, and a second end of the elongate member extends through a septum of the heart; placing a first anchoring member external the heart; and placing a second anchoring member inside the heart adjacent the septum. The first and second anchoring members are attached to the first and second ends of the elongate member respectively to fix the elongate member in a position across the heart chamber.

According to a further aspect, the invention comprises a method for improving the function of a valve of a heart. The method includes the steps of placing an elongate member transverse a heart chamber so that each end of the elongate member extends through a wall of the heart; and placing first and second anchoring members external the chamber. The first and second anchoring members are attached to the ends of the elongate member to fix the elongate member in a position across the chamber. The position is superior to the papillary muscles and proximate and substantially across the valve.

According to an even further aspect, the invention comprises a splint for improving the function of a valve of a heart. The splint includes an elongate member configured to be positioned transverse a heart chamber so that each end of the elongate member extends through a wall of the heart, and first and second anchoring members configured to be positioned external the chamber and attached to the ends of the elongate member to fix the elongate member in a position across the chamber. The first anchoring member includes a first portion configured to contact a first region of the heart proximate the valve to change a shape of the valve. Preferably, the first portion will contact a first region of the heart proximate the valve annulus to change the shape of the valve annulus.

According to another aspect, the invention comprises a splint for improving the function of a valve of a heart. The splint includes an elongate member configured to be positioned transverse a heart chamber so that each end of the elongate member extends through a wall of the heart, first and second anchoring members configured to be positioned external the chamber and attached to the ends of the elongate member to fix the elongate member in a position across the chamber, a third anchoring member connected to at least one of the first and second anchoring members by a connection member. The third anchoring member is configured to contact a region of the heart proximate the valve to change a shape of the valve.

According to a further aspect, the invention comprises a device for improving the function of a valve of a heart. The device includes a first splint having a first elongate member configured to be positioned transverse a heart chamber so that each end of the elongate member extends through a wall of the heart, and a first anchoring member configured to be positioned external the chamber and attached to a first end of the first elongate member. The device further includes a second splint having a second elongate member configured to be positioned transverse a heart chamber so that each end of the second elongate member extends through a wall of the heart, and a second anchoring member configured to be positioned external the chamber and attached to a first end of the second elongate member. The device also includes a connecting mechanism configured to be connected to the second ends of each of the first and second elongate members external the chamber and press the wall of the heart chamber to change a shape of the valve.

Yet a further aspect of the invention includes a method for improving cardiac function, comprising placing a first member relative to a heart chamber to alter the cross-sectional shape of the chamber and placing a second member relative to a valve of the heart chamber to assist in apposition of leaflets of the valve.

According to an even further aspect, the invention includes a method of improving the function of a valve of a heart comprising applying a force to an exterior surface of a wall surrounding a chamber of the heart substantially at a location of the valve to alter a shape of the valve.

Yet a further aspect of the invention includes a method for improving the function of a valve of a heart comprising placing a device relative to the heart to alter a shape of the valve and adjusting the device relative to the heart based on data obtained during the adjusting from real-time monitoring of valve function.

Another aspect of the present invention pertains to splint devices, and related splinting methods, for endovascular implantation on the heart. The splints of the present invention may be implanted endovascularly through remote vascular access sites. The inventive techniques and devices thus are minimally invasive and less risky to patients.

According to an aspect of the invention, a method for placing a splint assembly transverse a heart chamber comprises providing an elongate member having a first end and a second end and a deployable heart-engaging assembly connected to at least the first end. The method further includes advancing the elongate member through vasculature structure and into the heart chamber such that the first end of the elongate member extends through a first location of a wall surrounding the heart chamber and the second end extends through a second location of the heart chamber wall substantially opposite the first location. A deployable heart-engaging assembly is deployed such that it engages with a first exterior surface portion of the heart chamber wall adjacent the first location. The elongate member is secured with respect to the heart with a second heart-engaging assembly connected to the second end. The second heart-engaging assembly engages with a second exterior surface portion of the heart chamber wall adjacent the second location.

Another aspect of the invention includes a splint assembly for treating a heart, comprising an elongate member configured to extend transverse a chamber of the heart and at least one heart-engaging assembly formed at least partially from portions forming the elongate member. The heart-engaging assembly has a collapsed configuration adapted to travel through a heart wall and an expanded configuration adapted to engage the heart wall.

Yet another aspect of the invention includes a delivery tool for delivering a transventricular splint assembly to a chamber of the heart, comprising a tubular member having a distal end and a proximal end, the distal end having a curved configuration and the tube defining a lumen configured to carry at least a portion of the splint assembly. The delivery tool further includes at least one support mechanism disposed proximate the distal end of the tubular member, the support mechanism being configured to stabilize the tubular member with respect to a heart wall surrounding the chamber. The tubular member is configured to be advanced through vasculature structure and into the heart chamber.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 3b is an external view of a human heart showing the orientation of the mitral valve splint and series of transventricular splints of FIG. 3a;

DESCRIPTION OF THE PREFERRED EMBODIMENTS

Figure 1:
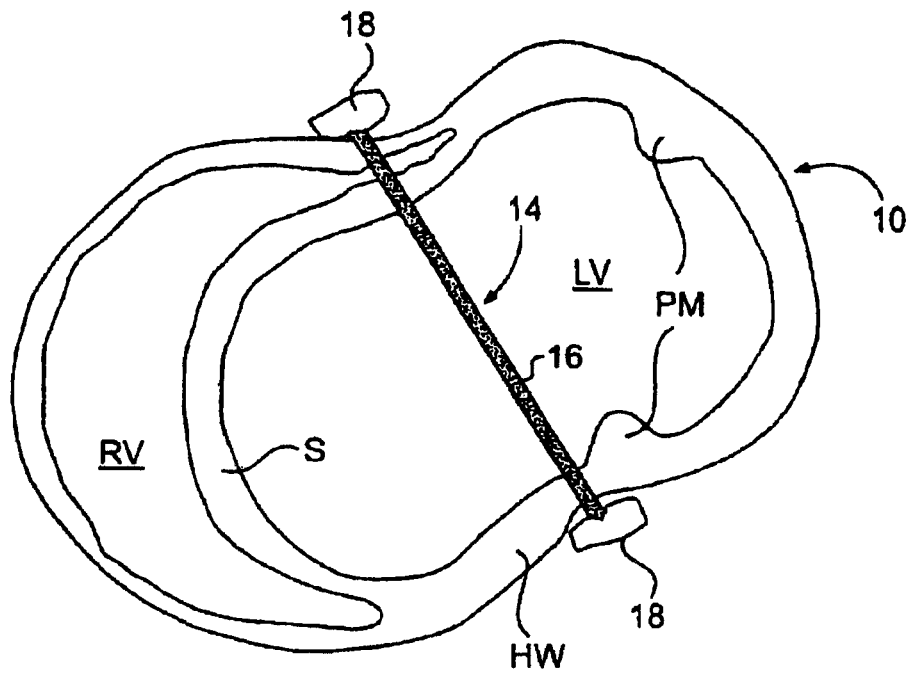
FIG. 1 is a transverse cross section of the left and right ventricles of a human heart showing the placement of splints according to an orientation for lessening myocardial muscular stresses.

The various aspects of the invention to be discussed herein generally pertain to devices and methods for treating heart conditions, including, for example, dilatation, valve incompetencies, including mitral valve leakage, and other similar heart failure conditions. Each device of the present invention preferably operates passively in that, once placed in the heart, it does not require an active stimulus, either mechanical, electrical, or otherwise, to function. Implanting one or more of the devices of the present invention operates to assist in the apposition of heart valve leaflets to improve valve function. In addition, these devices may either be placed in conjunction with other devices that, or may themselves function to, alter the shape or geometry of the heart, locally and/or globally, and thereby further increase the heart's efficiency. That is, the heart experiences an increased pumping efficiency through an alteration in its shape or geometry and concomitant reduction in stress on the heart walls, and through an improvement in valve function.

The inventive devices and related methods offer numerous advantages over the existing treatments for various heart conditions, including valve incompetencies. The devices are relatively easy to manufacture and use, and the surgical techniques and tools for implanting the devices of the present invention do not require the invasive procedures of current surgical techniques. For instance, the surgical technique does not require removing portions of the heart tissue, nor does it necessarily require opening the heart chamber or stopping the heart during operation. For these reasons, the surgical techniques for implanting the devices of the present invention also are less risky to the patient than other techniques. The less invasive nature of the surgical techniques and tools of the present invention may also allow for earlier intervention in patients with heart failure and/or valve incompetencies.

The disclosed inventive devices and related methods involve geometric reshaping of the heart and treating valve incompetencies. In certain aspects of the inventive devices and related methods, substantially the entire chamber geometry is altered to return the heart to a more normal state of stress. Models of this geometric reshaping, which includes a reduction in radius of curvature of the chamber walls, can be found in U.S. Pat. No. 5,961,440 incorporated above. Prior to reshaping the chamber geometry, the heart walls experience high stress due to a combination of both the relatively large increased diameter of the chamber and the thinning of the chamber wall. Filling pressures and systolic pressures are typically high as well, further increasing wall stress. Geometric reshaping according to the present invention reduces the stress in the walls of the heart chamber to increase the heart's pumping efficiency, as well as to stop further dilatation of the heart.

Although many of the methods and devices are discussed below in connection with their use in the left ventricle and for the mitral valve of the heart, these methods and devices may be used in other chambers and for other valves of the heart for similar purposes. One of ordinary skill in the art would understand that the use of the devices and methods described herein also could be employed in other chambers and for other valves of the heart. The left ventricle and the mitral valve have been selected for illustrative purposes because a large number of the disorders that the present invention treats occur in the left ventricle and in connection with the mitral valve. It also is contemplated that the inventive endovascular splinting devices and methods will be used to support an infarcted heart wall to prevent further dilatation, or to treat aneurysms in the heart. U.S. application Ser. No. 09/422,328, filed on Oct. 21, 1999, entitled "Methods and Devices for Improving Cardiac Function in Hearts" now issued as U.S. Pat. No. 6,406,420, which is assigned to the same assignee as the present application and is incorporated by reference herein, discusses this form of heart failure in more detail. Furthermore, the devices disclosed herein for improving valve function can be "stand-alone" devices, that is, they do not necessarily have to be used in conjunction with devices for changing the shape of a heart chamber or otherwise reducing heart wall stress. It also is contemplated that a device for improving valve function may be placed relative to the heart without altering the shape of the chamber, and only altering the shape of the valve itself.

Reference will now be made in detail to the present preferred embodiments of the invention, examples of which are illustrated in the accompanying drawings. Wherever possible, the same reference numbers will be used throughout the drawings to refer to the same or like parts.

A currently preferred orientation of transventricular splints for lessening myocardial muscular stresses is shown in FIG. 1, which shows the short-axis left ventricular cross-section from an anterior perspective. Examples of particular transventricular splints that are especially suitable for this application include those shown and described in copending U.S. patent application Ser. No. 09/532,049 to Vidlund et al., filed Mar. 21, 2000, entitled "A Splint Assembly for Improving Cardiac Function in Hearts, and Method for Implanting the Splint Assembly," now issued as U.S. Pat. No. 6,537,198 and commonly-assigned to the assignee of the present invention. The complete disclosure of that application is incorporated by reference herein. That application will be referred to as "the '049 application" in the remainder of this disclosure.

In the preferred orientation shown in FIG. 1, three splints are placed in a coplanar fashion, along the long axis of the ventricle, bisecting the left ventricle LV of the heart 10. FIG. 1 is a cross-section (short axis) view looking from the superior side of the heart. The superior-most splint 14 is placed at approximately the level of the heads of the papillary muscles PM and below the level of leaflet coaptation, and the additional two splints (not shown in FIG. 1) are placed inferiorly toward the apex. The preferred orientation shown in FIG. 1 both bisects the left ventricle LV and avoids key structures such as coronary vessels and the like. The splints according to this orientation also extend through the septum S near its edge and enter a small portion of the right ventricle RV.

Each splint includes a tension member 16 and an anchor assembly 18 at each end of the tension member 16. Presently preferred embodiments of tension members 16, anchor assemblies 18, and their connection to one another are disclosed in the '049 application incorporated by reference above. As shown in FIG. 1, tension member 16 extends through the heart wall HW, across the left ventricle LV, and through the septum S and a portion of the right ventricle RV. Anchor assemblies 18 are placed adjacent the external surface of the heart wall HW.

Figure 2A:
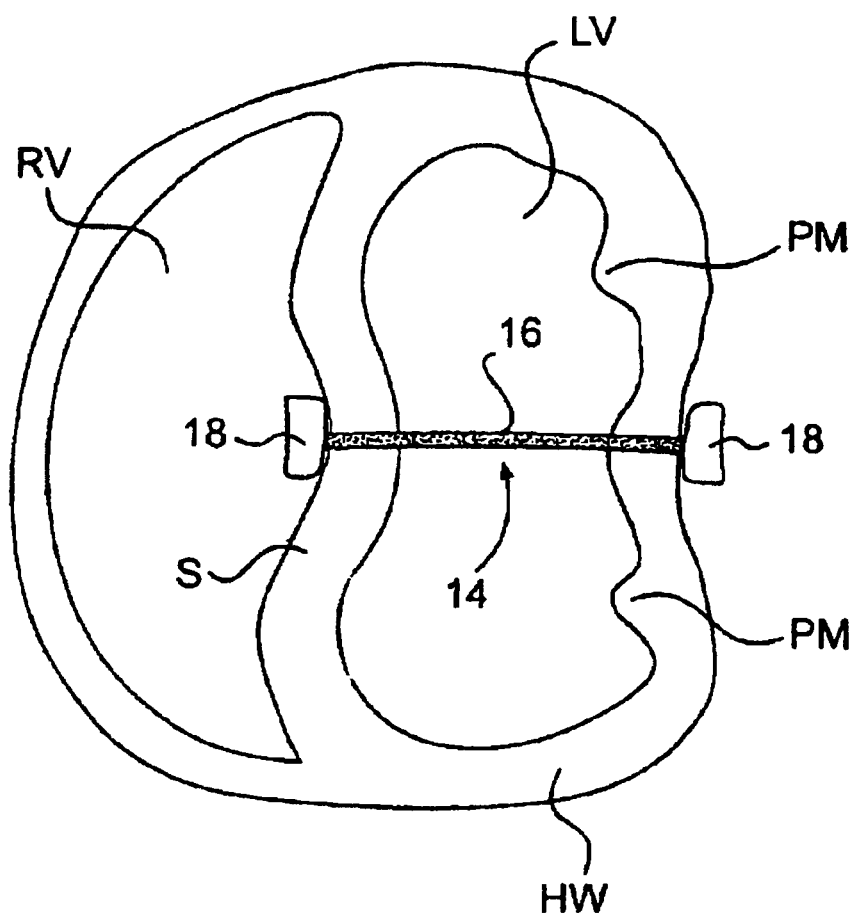
FIG. 2a is a transverse cross section of the left and right ventricles of a human heart showing the orientation of splints according to an embodiment of the present invention for lessening myocardial muscular stresses and assisting in apposition of valve leaflets.

As mentioned above, human implantations of splints, including in an orientation shown in FIG. 1, may exacerbate any pre-existing mitral valve incompetency, including mitral valve regurgitation (MVR), or at the least, may not improve any pre-existing MVR. FIG. 2a shows an orientation of splints 14 according to an embodiment of the present invention which may assist in both offloading myocardial wall stress and in aiding the apposition of valve leaflets. According to this orientation, each tension member 16 of splint 14 extends through the heart wall HW at a position approximately midway between the antero lateral papillary muscle PM and the posterio medial papillary muscle PM, extends transverse the left ventricle LV, and extends through the septum S at approximately its midpoint. A first anchor assembly 18 is placed external the heart 10 adjacent the heart wall HW and a second anchor assembly is placed inside the right ventricle RV adjacent septum S. FIG. 2a shows the superior-most splint 14 of preferably three splints, with the other two splints placed inferiorly towards the apex. More or less than three splints may be used. The splints in this orientation are generally parallel to one another and substantially perpendicular to the long axis of the left ventricle.

The orientation of splints 14 shown in FIG. 2a helps to "pull" both of the papillary muscles PM toward the center of the left ventricle LV and reposition those muscles closer to their normal physiological position relative to the mitral valve annulus during the complete cardiac cycle. During the course of heart failure dilation, the papillary muscles PM are moved laterally away from their normal position, which causes the chordae connected to both valve leaflets to become excessively taut. This in turn inhibits the leaflets from fully closing against each other. By bringing the papillary muscles PM closer to the center of the ventricle LV, the chordae are slackened enough to allow the leaflets to appose, thereby improving on mitral valve function. Additionally, although the splints 14 in this approach are preferably positioned at and below the level of the tops of the papillary muscles PM, the shape change deformation at the superior-most splint 14 would extend in a region further superior, and potentially include the annulus itself. To the extent that the annulus in the region of the posterior leaflet is deformed, this would further benefit the valve function by reducing the cross-sectional area of the annulus and positioning the posterior leaflet and its attachment zone closer to the anterior annulus. This, in turn, will cause the leaflets to more fully appose, minimizing MVR.

Various methods may be employed to implant the splints 14 in the orientation shown in FIG. 2a. One particularly advantageous method is an endovascular delivery technique shown and described in co-pending U.S. patent application Ser. No. 09/679,550 (now U.S. Pat. No. 6,616,684) to Robert M. Vidlund et al., entitled "Endovascular Splinting Devices and Methods," filed on Oct. 6, 2000 and commonly assigned to the assignee of this application, the entire disclosure of which is incorporated by reference herein, and discussed elsewhere herein. Splints 14 also may be positioned in the orientation shown in FIG. 2a by other surgical techniques, such as those described in the '049 application incorporated by reference above. For example, to gain access to the ventricular septum S, a small incision can be placed within the right ventricular wall to allow for positioning tension member 16 and the anchor assembly 18 within the right ventricle RV. The methods of implantation shown and described in the applications referred to above may be used in connection with any of the embodiments shown and described herein.

Figure 2B:
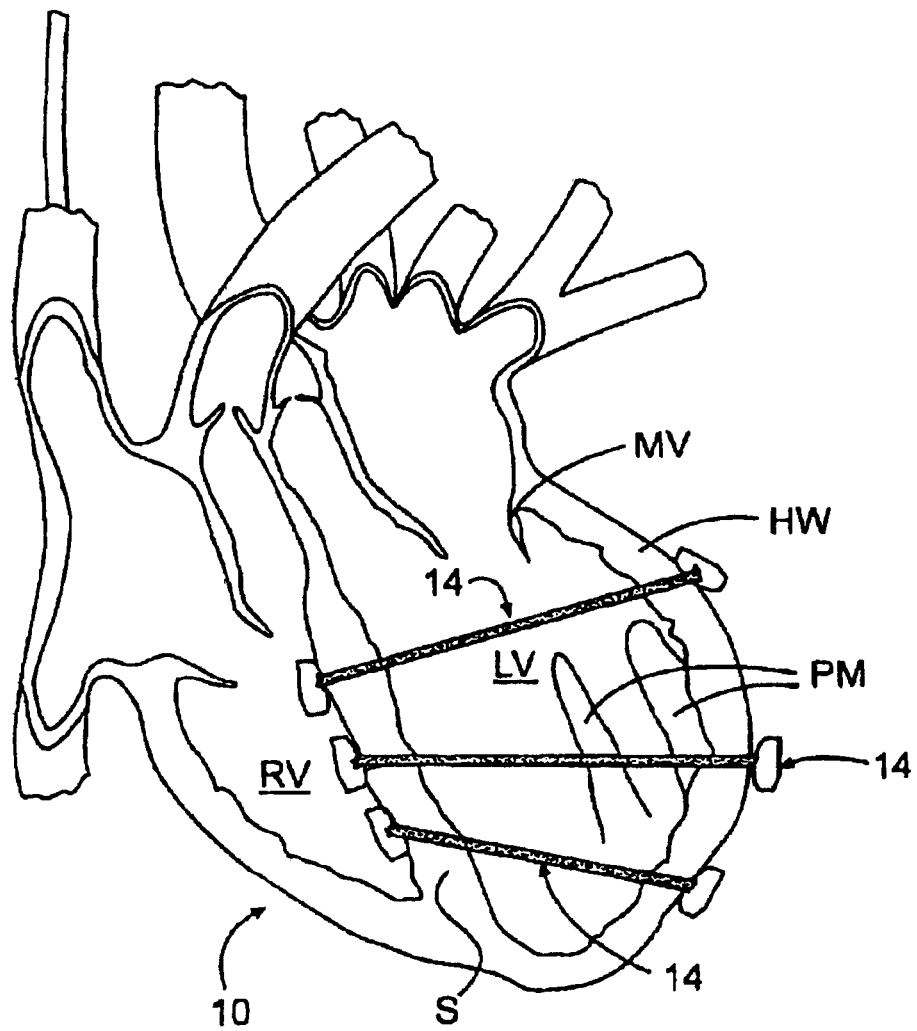
FIG. 2b is a vertical cross section of the left and right ventricles of a human heart showing another orientation of ventricular shape change splints according to an embodiment of the present invention for lessening myocardial muscular stresses and assisting in apposition of valve leaflets.

FIG. 2b shows another orientation of splints 14 according to an embodiment of the present invention which may assist in the offloading of myocardial wall stress and in the apposition of valve leaflets. According to this orientation, at least one splint 14 is angled with respect to the long axis of the left ventricle LV, in contrast to orienting the at least one splint 14 perpendicular to the axis of the left ventricle LV. In the embodiment shown in FIG. 2b, the lower two splints 14 are angled relative to the ventricular axis and relative to the superior-most splint 14, which is approximately perpendicular to the ventricular axis. In this example, all three splints 14 are coplanar, as is preferred for optimizing the ventricular shape change. While FIG. 2b illustrates the ventricular splints having an anchor pad disposed on the septum, it is contemplated that the benefits of angling one or more splints relative to the long axis of the ventricle could be achieved at other cross-sectional orientations including, for example, the orientation shown in FIG. 1, in which an anchor pad is located on an exterior wall of the heart as opposed to the septum wall.

Because the lower two splints 14 are positioned at an angle, they tend to "lift" one or both papillary muscles PM as they impart shape change to the left ventricle LV. By lifting the papillary muscle(s) PM, some slack may be provided to the chordae connected to the valve leaflets to permit improved apposition of the leaflets of mitral valve MV. It is contemplated that more or less splints than the lower two splints may be angled (other than perpendicularly) relative to the ventricular axis to achieve the benefits to MVR, and that each splint may have a different angle relative to that axis. For example, all three splints could be angled, or only one splint could be angled. The number of splints to be angled, and the degree of such angles, would be chosen to optimize the improvement in MVR and would depend on factors such as the particular anatomy of a heart. The splint positioning can be iteratively changed and the impact on MVR, and mitral valve function in general, can be monitored using appropriate "real-time" imaging techniques and equipment, such as, for example, ultrasound and other suitable mechanisms. The ventricular splints 14 shown in FIG. 2b may be oriented in any suitable cross sectional position including the positions shown in FIG. 1 or 2a. The benefits to MVR of angularly positioning one or more of the ventricular splints 14 relative to the ventricular axis, as shown in FIG. 2b, may be achieved independent of the particular cross sectional position of the splints 14.

According to an embodiment of the present invention, a method of improving mitral valve function, while maintaining the positions and orientations of the ventricular splints shown in FIG. 1, includes the use of an additional splint. This additional splint, referred to herein as a mitral valve splint or MV splint, preferably has the same construction as the other splints and may be implanted using the similar delivery techniques. The primary function of the MV splint is to impart a shape change to the mitral valve annulus, adjacent the left ventricular wall, as well as reposition the papillary muscles PM.

Figure 3A:
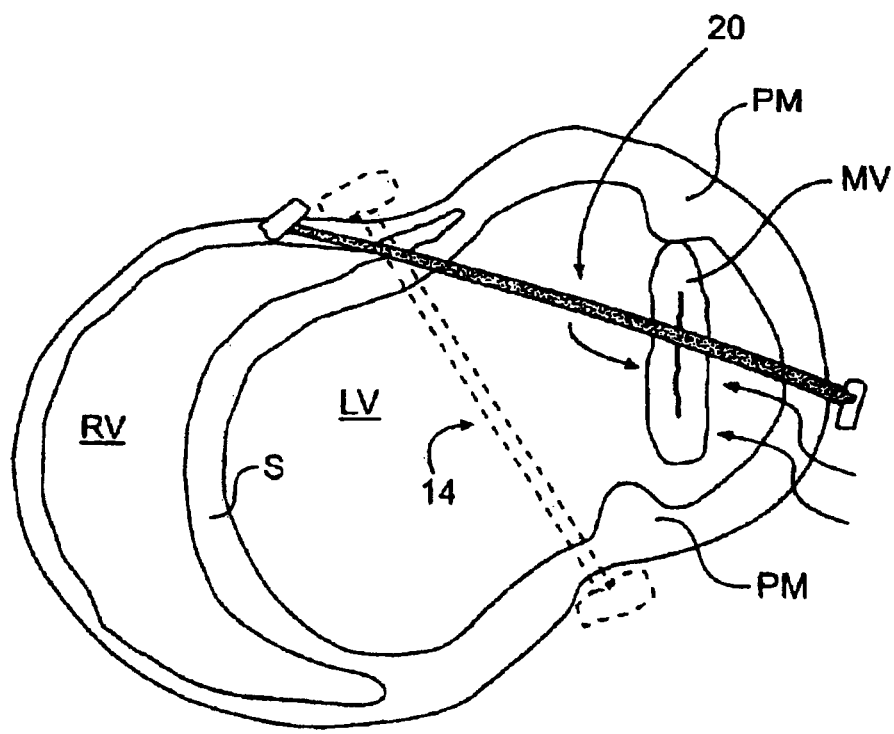
FIG. 3a is a transverse cross section of the left and right ventricles of a human heart showing an orientation of a mitral valve splint used in combination with a series of transventricular splints according to an embodiment of the present invention for lessening myocardial muscular stresses and assisting in apposition of valve leaflets.
Figure 3B:
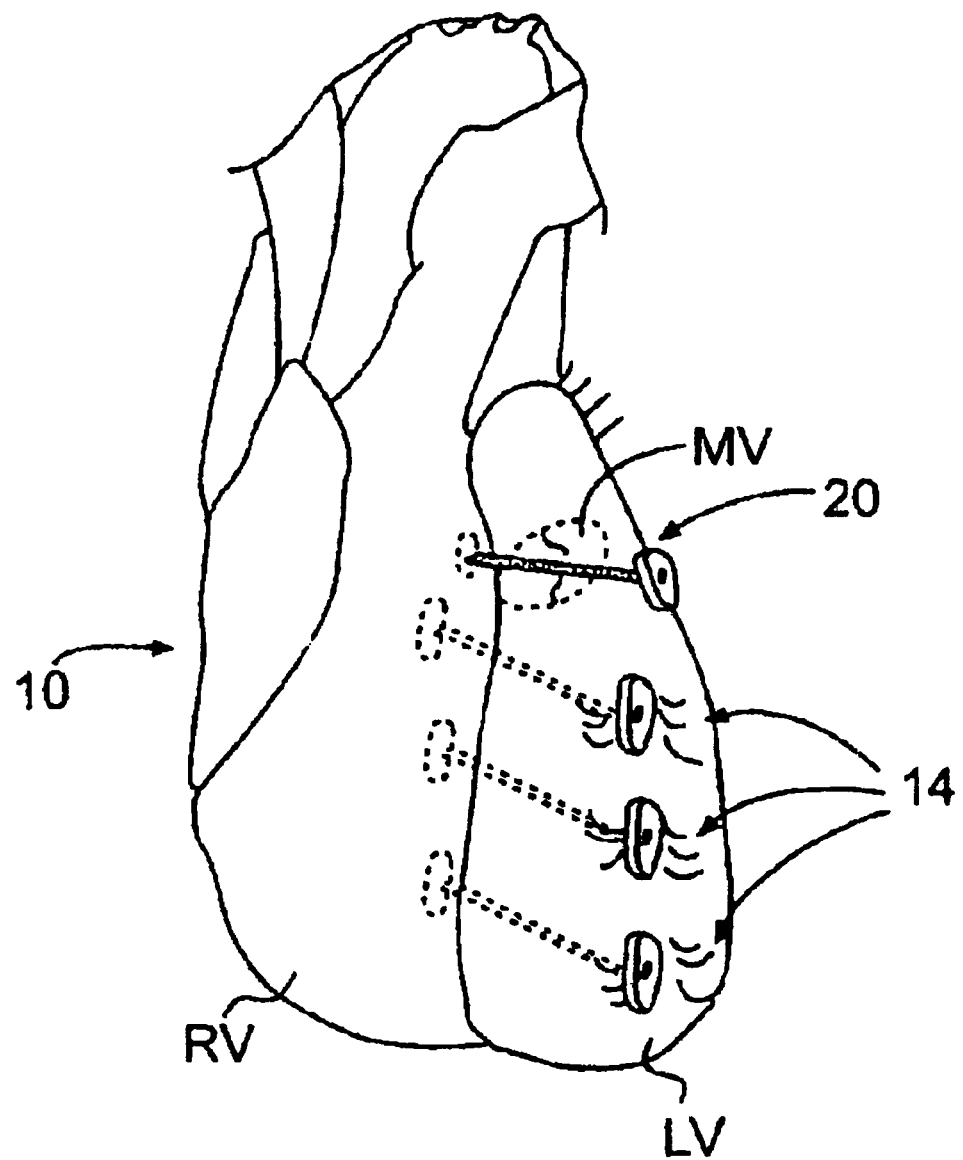

FIGS. 3a and 3b show an MV splint according to an embodiment of the present invention. FIGS. 3a and 3b show the three ventricular splints 14 in the positions and orientations shown and described in connection with FIG. 1 (the dashed lines in FIGS. 3a, 3b) and show an exemplary orientation of an MV splint 20. It should be noted that in FIGS. 3a and 3b the shape change to the left ventricle caused by the transventricular splints 14 is not illustrated. MV splint 20 is positioned superior to the papillary muscles PM and oriented primarily across the mitral valve MV and on or below the mitral valve annulus while avoiding key vascular structures. In this orientation, MV splint 20 is "out of plane" with the other ventricular splints 14, as the overall function of MV splint 20 is to improve and optimize the mitral valve function. In the example shown in FIGS. 3a and 3b, the MV splint extends through the heart wall between the papillary muscles of the left ventricle LV, and extends transverse the left ventricle LV, through the septum S, through the right ventricle RV, and once again through the heart wall.

The MV splint 20 improves mitral valve function through a combination of effects. First, the shape of the annulus is directly altered, preferably during the entire cardiac cycle, thereby reducing the annular cross sectional area and bringing the posterior leaflet in closer apposition to the anterior leaflet. Second, the position and rotational configuration of the papillary muscles PM and surrounding areas of the left ventricle LV are further altered by the tightening of the MV splint 20. This places the chordae in a more favorable state of tension, allowing the leaflets to more fully appose each other. Third, since the annulus of the valve is muscular and actively contracts during systole, changing the shape of the annulus will also reduce the radius of curvature of at least portions of the annulus, just as the shape change induced by the ventricular splints reduces the radius of at least significant portions of the ventricle. This shape change and radius reduction of the annulus causes off-loading of some of the wall stress on the annulus. This, in turn, assists the annulus's ability to contract to a smaller size, thereby facilitating full closure of the mitral valve MV during systole.

The position of the MV splint 20 shown in FIGS. 3a and 3b is exemplary. The ventricular splints 14 preferably are positioned prior to positioning MV splint 20, through the use of, for example, both angiographic and ultrasonic visualization tools. This positioning technique, described in the '049 application incorporated above, achieves optimal positioning of splints 14 to bisect the left ventricle LV and avoid key anatomic structures. After positioning the ventricular splints 14, a device such as the probe/marking device shown and described in the '049 application may be used to repeatedly probe and deform possible areas near the mitral valve to find the optimal position for the MV splint 20. By utilizing, for example, standard "real-time" ultrasonic imaging techniques, the direct impact of the probing on MVR can be assessed, and pre-existing MVR or MVR exacerbated by placement of the ventricular splints 14 can be corrected. Once the optimal position for an MV splint 20 is determined and marked, the MV splint 20 is implanted and positioned by any of the delivery techniques referred to above, including the endovascular delivery technique or the more direct surgical approaches. The use of the MV splint 20 allows for the optimal placement of the ventricular splints 14, which reduce heart wall stress, independent from the optimal subsequent positioning of the MV splint 20, which improves mitral valve function. During implantation, the splint can be adjusted (either in position or in tightness or both) to optimize improvement to valve function, as determined by observation of the valve using real-time imaging techniques.

Figure 3C:
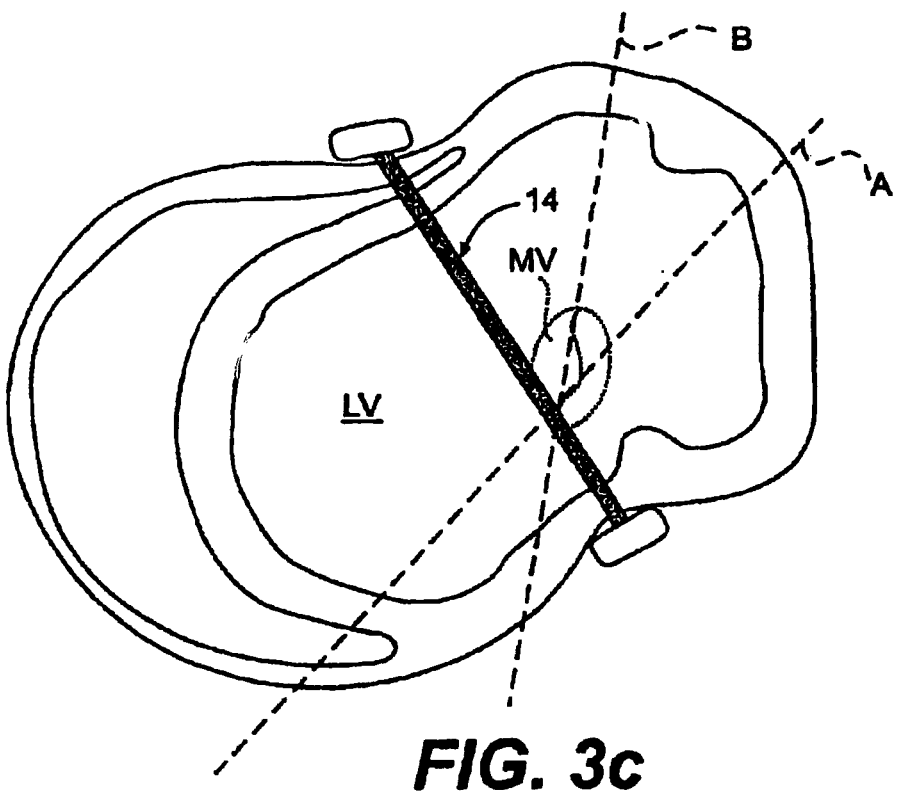
FIG. 3c is a transverse cross section of the left and right ventricle of a human heart showing a various orientations for a mitral valve splint used in combination with a series of transventricular splints according to an embodiment of the present invention.

It is anticipated that the optimal position of the MV splint 20 could be at virtually any orientation relative to the valve leaflets, depending on the heart failure and mitral valve regurgitation associated with the particular heart at issue. For example, in some hearts, the position shown and described in connection with FIGS. 3a and 3b may yield the most improvement of MVR, whereas in other hearts, alternative positions such as shown in FIG. 3c may yield the most improved results. Note that in FIG. 3c, the transventricular splint is shown positioned between the papillary muscles, which may be another preferred orientation for certain hearts. Alternative "A" places MV splint to cause shape change between the papillary muscles Alternative "B" for MV splint positioning would be in a line more parallel to the valve leaflet edges, as shown in FIG. 3d. Other placements of the MV splint, as well as the position of the transventricular splints, relative to the heart also are contemplated and could be selected based on the condition of the heart and the mitral valve.

According to another embodiment of the present invention, an alternative anchor assembly for the ventricular splints 14 may be provided to aid in mitral valve function. In the embodiment shown in FIG. 4a, the superior-most splint 14 includes an anchor assembly 28 configured for connection to the "free wall" end of that splint 14, i.e., at the exterior wall of the left ventricle. Anchor assembly 28 includes a lower portion in the form of, for example, a lower pad portion 30 which contacts the external surface of the left ventricle wall somewhat below the level of the tension member 16. In a preferred embodiment, the lower pad portion 30 resembles the shape, size, and construction of the anchor pads described in the '049 application incorporated above. Anchor assembly 28 further includes an upper portion in the form of, for example, an upper pad portion 34 which contacts a superior region of the left ventricle wall near the mitral valve annulus. Tension member 16 connects to a spanning structure 32 that, in one embodiment, is preferably integrally fabricated with the lower and upper pad portions 30 and 34, and connects portions 30 and 34. Suitable materials for anchor assembly may include, but are not limited to, those described in the '049 application. At least the lower and upper pad portions 30 and 34 preferably include a covering or a coating of a material, such as, for example, a woven polyester fabric, to encourage tissue in-growth. The spanning structure 32 also may be made of, or include a covering or coating made of, a material to encourage tissue in-growth.

Figure 4A:
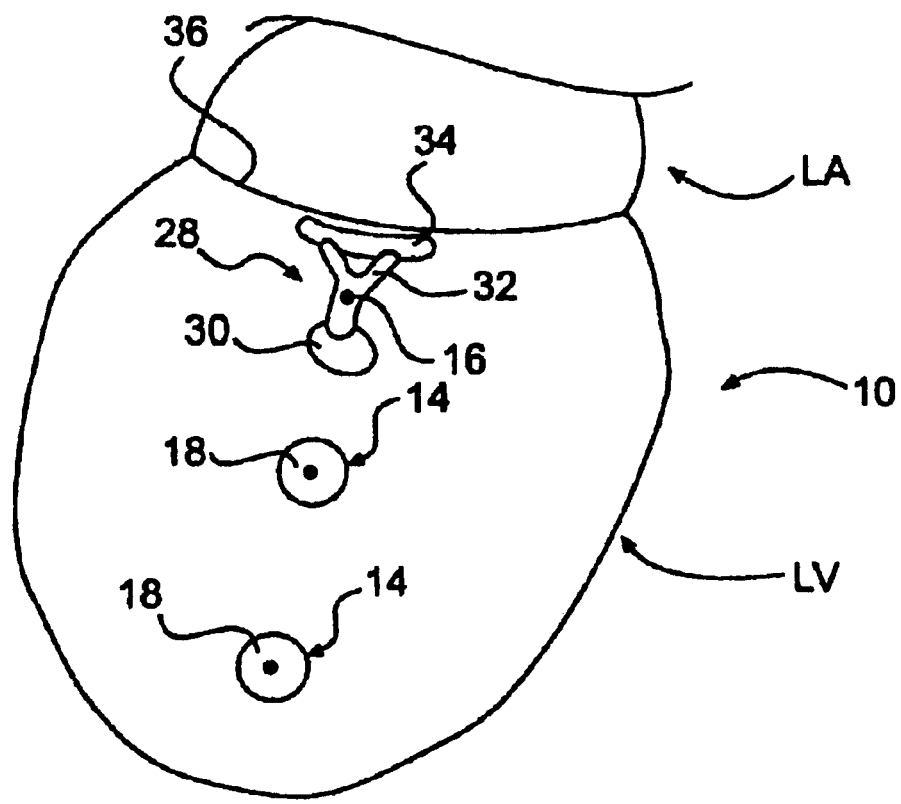
FIG. 4a is an external view of a human heart showing a series of transventricular splints, with the superior-most splint having an anchor structure according to an embodiment of the present invention that assists in apposition of valve leaflets.

In the exemplary, preferred embodiment shown in FIG. 4a, the lower pad portion 30 has a circular shape and the upper pad portion 34 has an oblong shape. The oblong shape of the upper pad portion 34 has the advantage of inducing relatively extensive shape change along the periphery of the valve annulus, preferably during the entire cardiac cycle. Therefore, in an embodiment, the length, and shape of the upper pad portion may extend a significant distance around the valve annulus. For example, the upper pad portion 34 may extend from about 1 cm in length to about 10 cm in length, depending on the desired shape change of the valve annulus. The width of the upper pad portion 34, however, is preferably relatively narrow, so as to concentrate its shape change impact to the region near the valve annulus.

The upper pad portion 34 may be positioned near, but below, the valve annulus. In other embodiments of the present invention, the upper pad portion may be positioned directly on the exterior surface of the annulus or somewhat above the annulus to contact the left atrium wall. The position of the upper pad portion preferably avoids direct compressive contact with important vascular structure near or on the exterior surface of the heart. Significant coronary vasculature often lies on or near the atrio-ventricular groove 36, which corresponds with the posterior annular region of the mitral valve. For this reason, it may be desirable to position the upper pad portion onto the left atrial surface.

Anchor assembly 28 permits selection of a position that causes valve annulus shape change relatively independent from the positioning of the ventricular splints that cause ventricular shape change. The incorporation of an anchor assembly 28 is most suitable for instances where the desired shape change for the mitral valve is relatively co-planar with the main ventricular shape change splints. In addition, anchor assembly 28 provides for annulus shape change without the need for an additional MV splint, such as that shown in FIGS. 3a and 3b.

Figure 4B:
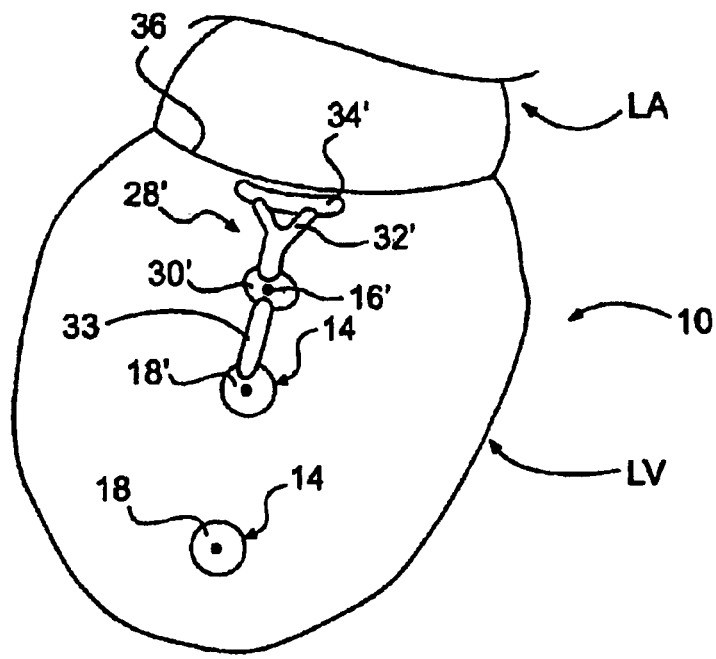
FIG. 4b is an external view of a human heart showing a series of transventricular splints, with the superior most splint having an anchor structure and a connection mechanism between the superior most and middle anchors according to yet another embodiment of the present invention that assists in apposition of valve leaflets.

An alternative embodiment of a splint with a mitral valve anchor assembly according to the invention is illustrated in FIG. 4b. In the embodiment of anchor assembly 28, shown in FIG. 4a, the tension member 16 was connected to the spanning structure 32 approximately in the middle of the spanning structure 3, yielding a relatively stable structure that remains substantially parallel to the exterior surface of the heart. However, the embodiment of the anchor assembly 28' shown in FIG. 4b places the ventricular shape change caused by the lower pad portion 30' below the end of the tension member 16'. The anchor assembly 28' illustrated in FIG. 4b is similar to the anchor assembly 28 of FIG. 4a, except that the tension member 16' is anchored within the lower pad portion 30'. In order to provide mechanical balance to the anchor assembly, and to give leverage to the upper pad portion 34' such that it can properly alter the region of the valve annulus, a second spanning structure 33 is provided to mechanically connect the anchor assembly 28' to an anchor pad 14 of the splint disposed below the superior-most splint. This second spanning structure 33 also may be integrally formed with the anchor assembly 28' and, in turn, with the anchor pad 14. Alternatively, the second spanning structure 33 can be a separate component connecting anchor assembly 28' and anchor pad 14' once they are positioned with respect to the heart. This could be done, for example, by mechanical fastening, such as with screws or the like.

Figure 4C:
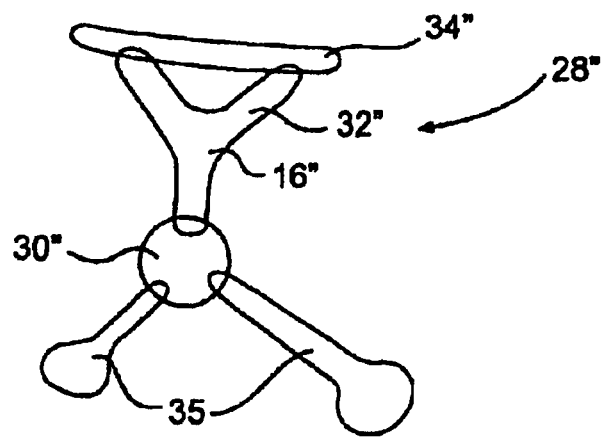
FIG. 4c is a perspective view of an anchor assembly for a transventricular splint according to yet another embodiment of the present invention that assists in apposition of valve leaflets and repositioning of papillary muscles.

A further alternative anchor assembly 28" is shown in FIG. 4c. This anchor assembly 28" is similar to the anchor assembly 28 shown in FIG. 4a, except that anchor assembly 28" also includes one or more additional papillary pad portions 35 connected to lower pad portion 30" at a location substantially opposite to spanning structure 32" The papillary pad portion or portions 35 serve to provide one or more additional sites of deformation of the ventricular wall, preferably to further reposition one or both papillary muscles to aid in apposition of the valve leaflets. The papillary pad portions 35 may be formed integrally with the anchor assembly 28" or may be separate and connected thereto via suitable connection mechanisms.

In certain cases, the optimal orientation of shape change for improving the mitral valve function may be significantly offset from the position and orientation of transventricular splints 14. It is therefore desirable to have an approach to cause mitral valve shape change at positions away from the transventricular splints 14, and even more desirably, without the addition of another splint structure traversing the ventricle.

Figure 5A:
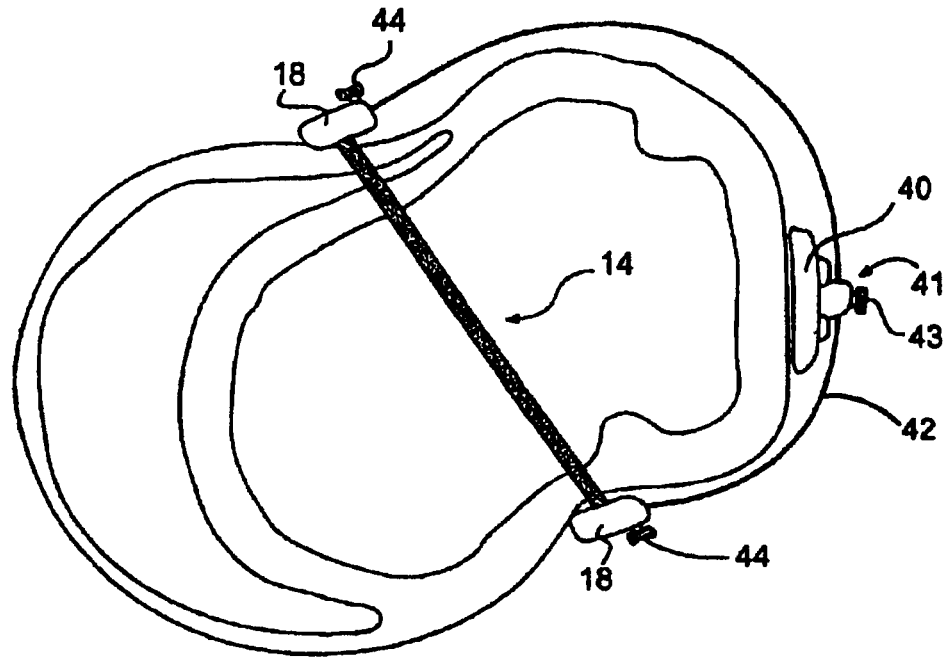
FIG. 5a is a transverse cross section of the left and right ventricles of a human heart showing the placement of splints according to an orientation for lessening myocardial muscular stresses with an accessory anchor assembly according to an embodiment of the present invention to assist in apposition of valve leaflets.

FIG. 5a shows such an approach according to an embodiment of the present invention. FIG. 5a shows an accessory anchor pad structure 40 attached to a connection member, shown as a runner 42. Runner 42 connects at its ends to both anchor pads 18 of preferably the superior-most splint assembly 14. As an alternative, runner 42 may connect to one anchor pad 18 and extend between that anchor pad 18 and structure 40. The accessory pad structure 40 is positioned at the location on the heart wall that yields the greatest improvement in MVR, as determined with repeated probing and deforming at the exterior of the heart proximate the mitral valve annulus, as described above in connection with positioning the MV splint 20 in FIGS. 3a and 3b.

Since runner 42 preferably connects to the two anchor pads 18 of the upper-most splint assembly 14, runner 42 generally runs at approximately the same level on the heart wall as those anchor pads 18. In one embodiment, accessory anchor pad structure 40 may be of the same shape and material as the anchor pads 18. While this embodiment may result in significantly improved MVR in some instances, in another embodiment, accessory pad 40 may take a form, including shape and material, similar to the anchor assemblies 28, 28', 28" shown in FIGS. 4a-4c. This latter configuration permits positioning accessory pad 40 at a position higher than the level of the anchor pads 18 of the superior-most transventricular splint, resulting in even greater shape change to the mitral valve annulus. Also according to this latter configuration, the preferred construction of accessory pad 40 would include, in addition to characteristics of anchor assembly 28, 28', 28", shown in FIGS. 4a-4c, a connecting mechanism 41 which would allow for adjustable positioning and securing of the accessory pad 41 to runner 42. For example, a locking screw 43 may be used to secure runner 42 to pad 41. Other mechanisms suitable for securing the pad 41 to the runner 42 and permitting adjustment of the pad position along the runner are within the scope of the present invention. Runner 42 preferably includes a wire-like, or braid-like, structure which secures to each of the splint anchor pads 18 also through any suitable means, such as, for example, a locking screw mechanism 44, a pinning connection for a braid-like runner, or the like.

Figure 5B:
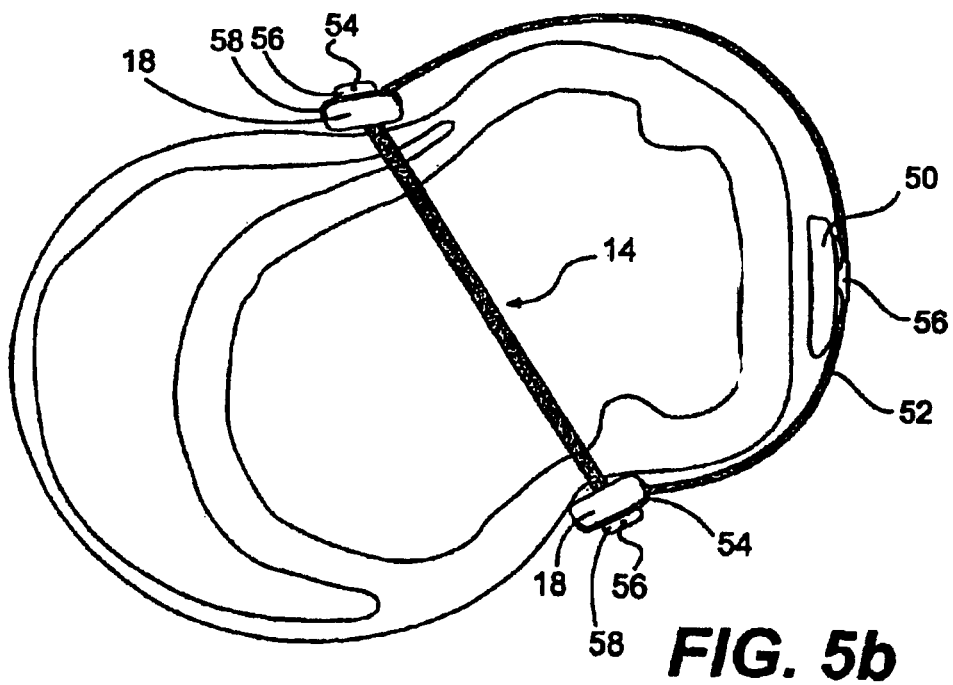
FIG. 5b is a transverse cross section of the left and right ventricles of a human heart showing the placement of splints according to an orientation for lessening myocardial muscular stresses with an accessory anchor assembly according to another embodiment of the present invention to assist in apposition of valve leaflets.

FIG. 5b shows an alternative embodiment for connecting an accessory anchor pad assembly 50 to a runner 52 and for connecting runner 52 to anchor pads 18. Each end of runner 52 connects to a connection mechanism in the form of a cap 54. Each cap 54 locks in place over a pad 18. At least one of the caps 54 includes an adjustable locking mechanism for adjusting the length of the runner 52 between the caps 54, and also thereby adjusting the position of the accessory pad 50 on the heart wall, and locking the runner 52 to cap 54.

In one embodiment, runner 52 is a braid formed of a high strength polymer, such as that used in the tension members described in the '049 application incorporated above. A suitable connection mechanism includes the use of one or more pins 56 placed through the braided runner 52 and connected to cap 54 through a flange 58, for example, situated on the cap 54. This pinning connection mechanism may be similar to the connection used for the braided tension members and anchor pads shown and described in the '049 application. The same connection mechanism may be used to connect accessory pad 50 to braided runner 52. In an alternative embodiment according to the present invention, the braided runner 52 may more directly connect to anchor pads 18, without the use of caps 54, by, for example, a pinning securement mechanism incorporated into the superior splint pads themselves. In another contemplated embodiment, the external anchor pad assembly 50, including the runner 52 and anchor pads 18, can be used without the transventricular splint to improve valve function by causing a shape change to the valve annulus without an overall shape change to the left ventricle.

As mentioned above, a mechanism that may exacerbate MVR is the relative rotation of the papillary muscles PM and the adjacent left ventricular wall as the transventricular splints 14 are tightened into position. This relative rotation results in slack in some chordae and tightening in other chordae, which may "pull" one valve leaflet (or portion of the leaflet) while "loosening" the other valve leaflet (or portion of the leaflet).

Figure 6:
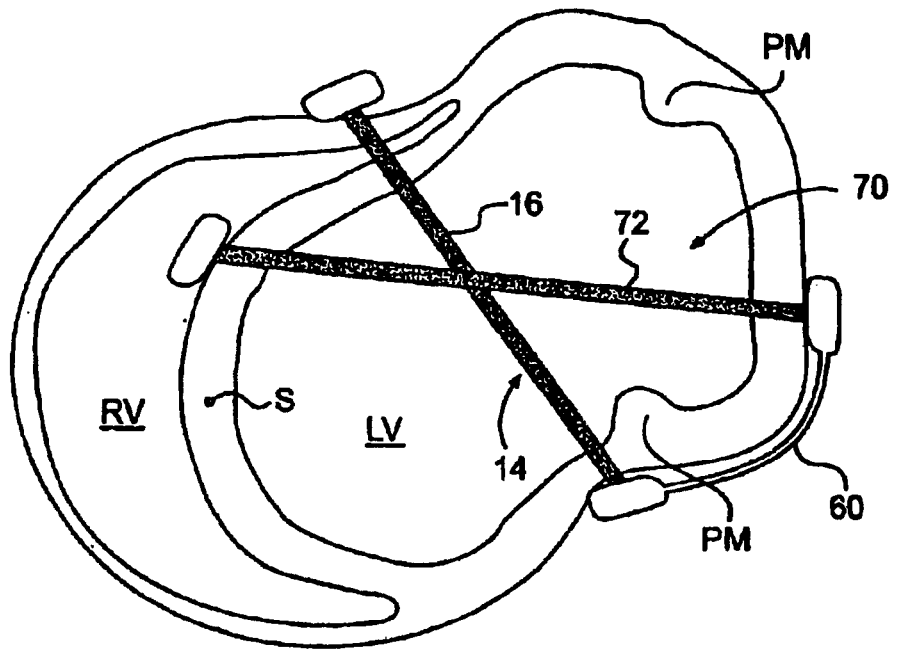
FIG. 6 is a transverse cross section of the left and right ventricles of a human heart showing an orientation of a mitral valve splint used in combination with a series of transventricular splints, with an interconnecting mechanism according to an embodiment of the present invention for lessening myocardial muscular stresses and assisting in apposition of valve leaflets.

FIG. 6 shows an embodiment of a device according to the present invention that would alleviate this rotation phenomenon. FIG. 6 shows an accessory splint 70 connected to the superior-most ventricular splint 14 by a connecting bar 60. Accessory splint 70 and connecting bar 60 preferably are placed at approximately the same level along the ventricular wall as splint 14. Splint 14 preferably is positioned near to, and in this case medial to, the anterior papillary muscle PM. Accessory splint 70 then is positioned through the septum S, across the left ventricle LV, and through the ventricular free wall between the papillary muscles PM, similar to MV splint 20 described in connection with FIGS. 3a and 3b but at about the same level as the superior splint 14.

Connecting bar 60 attaches to the ends of tension members 16 and 72 at their left ventricular "free wall" ends. Both tension members 16 and 72 are tensioned, pressing connecting bar 60 into the left ventricle and effecting shape change to the ventricle and the mitral valve annulus. Connecting bar 60 prevents rotation of the left ventricle LV in the region of the anterior papillary muscle PM and causes uniform tensioning of the chordae associated with that papillary muscle PM and any associated ventricular wall. This is believed to lessen any degradation in MVR, and potentially improve the MVR, because the papillary muscles PM are brought to a more desired position, with less rotation, particularly as to the anterior papillary muscle.

The embodiments of the present invention described in connection with FIGS. 2a to 6 have been described in connection with the use of transventricular splints used to geometrically reshape a chamber of the heart and thereby lessen heart wall stresses and reduce dilatation. While the devices and related methods described herein would further benefit the ventricular splinting procedure and its effects, the devices and related methods of the present invention may be used independent of the ventricular splinting to improve dilatation and instead be used for repairing heart valves, and particularly mitral valves, without the use of adjunctive ventricular splints. For example, a mitral valve splint such as that shown in FIGS. 3a, 3b, and 3c could be utilized without additional ventricular shape change splints.

Figure 7:
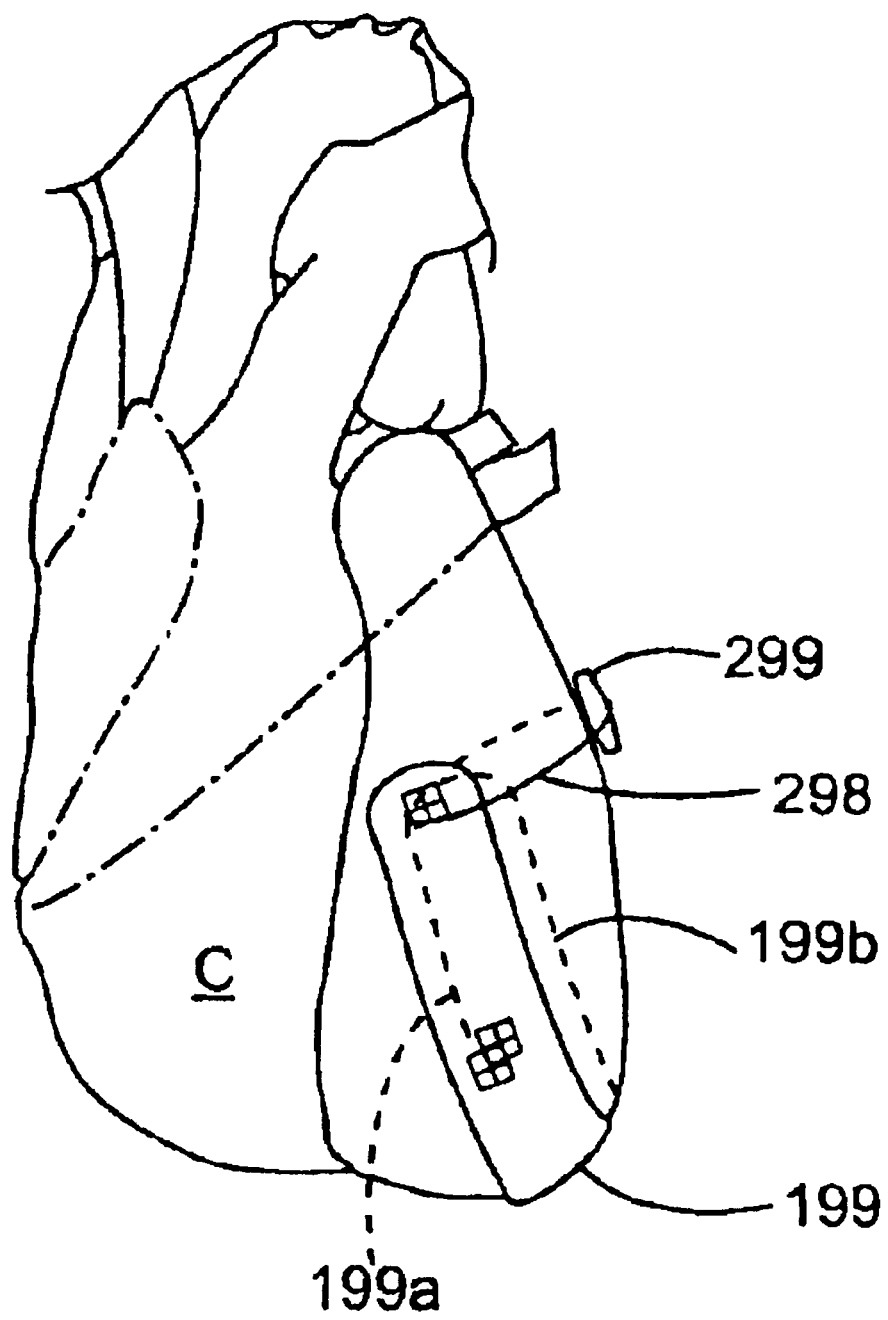
FIG. 7 is a perspective view of a heart with an external splint device and mitral valve anchor assembly and connecting mechanism disposed relative to the left ventricle to alter the shape of the left ventricle and to assist in apposition of valve leaflets according to an embodiment of the present invention.

Moreover, while many of the embodiments of the present invention have been described in connection with modifications to transventricular splinting structures, the same or similar modifications may be made to external-type devices for causing ventricular shape change. Examples of such external devices are shown co-pending U.S. patent application Ser. No. 09/157,486 ("the '486 application") filed Sep. 21, 1998 and entitled "External Stress Reduction Device and Method," now issued as U.S. Pat. No. 6,183,411, the complete disclosure of which is incorporated by reference herein. Modifying those external devices in a similar manner as with the transventricular splints will achieve beneficial impacts to the mitral valve function. For example, the accessory anchor pad shown in FIGS. 5a and 5b could be utilized in conjunction with an external stress reduction device, as shown, for example, in FIG. 7. In FIG. 7, an external splint 199 having a generally U-shaped configuration and including an anterior arm 199a and a posterior arm 199b, is positioned with respect to the left ventricle to create a substantially bi-lobed shape. In a preferred embodiment, the U-shaped external splint is made from a material that permits the splint to elastically deform under operational loads and also from a material that is biocompatible. Examples of preferred materials include e-PTFE, or a polyester such as Dacron, for example. Such a splint, as well as other suitable external splints, is described in more detail in the '486 application incorporated above. As shown in FIG. 7, a runner 298, similar to the runner described with reference to FIGS. 5a and 5b, attaches at its ends to the arms 199a, 199b. An accessory anchor pad 299, also similar to the accessory anchor assembly discussed with reference to FIGS. 5a and 5b, attaches to the connecting runner 298. The runner 298 and accessory anchor pad 299 are positioned with respect to the heart so as to alter the shape of the mitral valve annuls to assist in coaptation of the valve leaflets. Alternatively, the runner and accessory anchor pad could be positioned so as to provide a repositioning of the papillary muscles, also to assist in coaptation of the valve leaflets.

It will be apparent to those skilled in the art that various modifications and variations can be made in the devices and related methods for improving mitral valve function of the present invention and in construction of such devices without departing from the scope or spirit of the invention. As an example, a combination of devices depicted above may be used for achieving improved mitral valve function. In one such combination, an accessory splint such as MV splint 20 shown in FIGS. 3a and 3b may include an anchor assembly 28 as shown in FIG. 4 and/or an accessory anchor pad structure 40 or 50 shown in FIGS. 5a and 5b.

The endovascular techniques which will be described hereinafter do not require performing a sternotomy or removing portions of the heart tissue, nor do they require opening the heart chamber or stopping the heart during operation. Such percutaneous insertion permits the splinting procedures to be performed in a wide variety of laboratories in the hospital. For these reasons, the techniques for implanting the devices of the present invention also are less risky to the patient, both during and after the implantation, and may be performed more quickly than other techniques. For instance, the procedures of the invention cause less pain to patients and permit quicker healing. In addition, certain endovascular splinting techniques to be described may limit bleeding at access sites, allowing relatively large catheters, cannula, and other similar implantation tools to be inserted in a percutaneous manner.

An embodiment of an endovascular splinting technique according to the present invention is shown in FIGS. 8-17. In this splinting technique, access to the left ventricle LV and delivery of the splint occurs from within the right ventricle RV. An approach from within the right ventricle is preferred for a number of reasons. First, the right ventricle is highly accessible through venous structure that leads into the superior vena cava VC, for example from the right or left jugular veins. Since these veins typically are at a relatively low pressure, bleeding at the access sites is limited, and rather large catheters, cannula and the other like surgical tools can be inserted into the veins in a percutaneous manner. Furthermore, this technique permits access to vascular structure without a sternotomy or other open chest surgical access, thereby minimizing trauma to the patient. Additionally, patients are less likely to experience embolic events. Recovery times for the operation also are reduced, due to the minimally invasive nature of such procedures.

Second, delivery through the right ventricle allows for straightforward positioning of the splints on the ventricular septal wall SW. Such positioning on the septal wall is preferable because it results in good left ventricle bisection, in a manner believed to have minimal negative impact on mitral valve function, and in some instances, a positive impact on mitral valve function and performance. Moreover, delivery through the right ventricle does not involve the free wall of the right ventricle and also does not restrict outflow of the blood from the heart.

Figure 8:
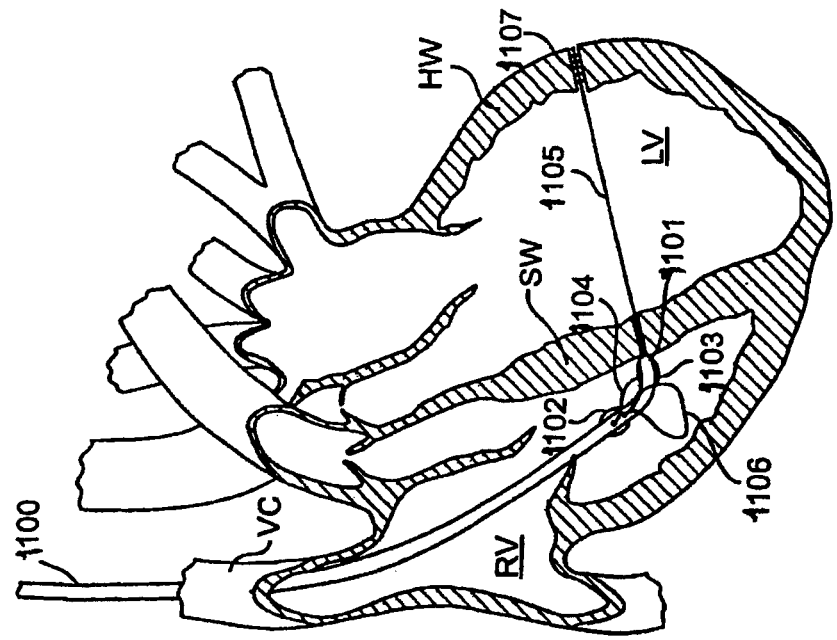
FIG. 8 is a vertical cross-sectional view of the heart showing a delivery catheter inserted endovascularly into the right ventricle according to an aspect of the present invention.
Figure 9:
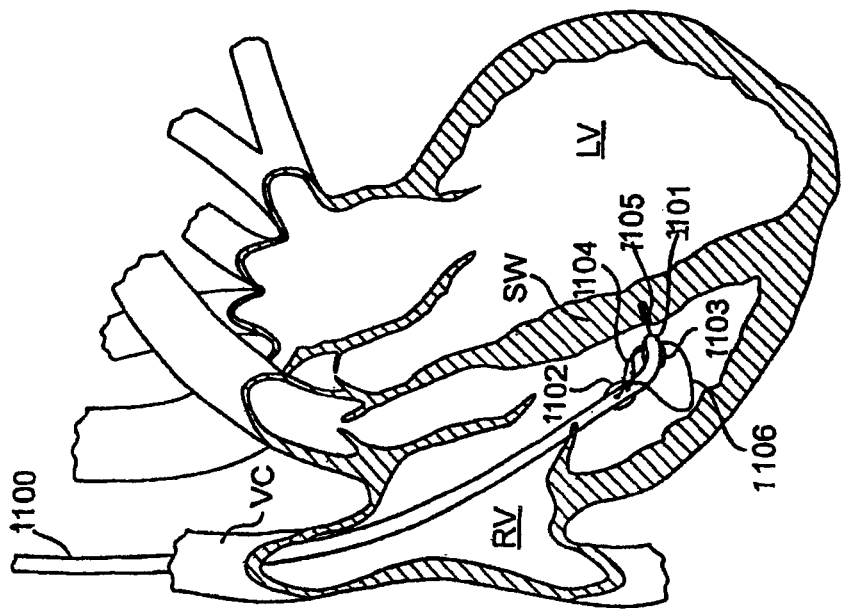
FIG. 9 is a vertical cross-sectional view of the heart showing a guide wire extending from the catheter of FIG. 8 through the septal wall, across the left ventricular chamber and into the free wall according to an aspect of the present invention.
Figure 30:
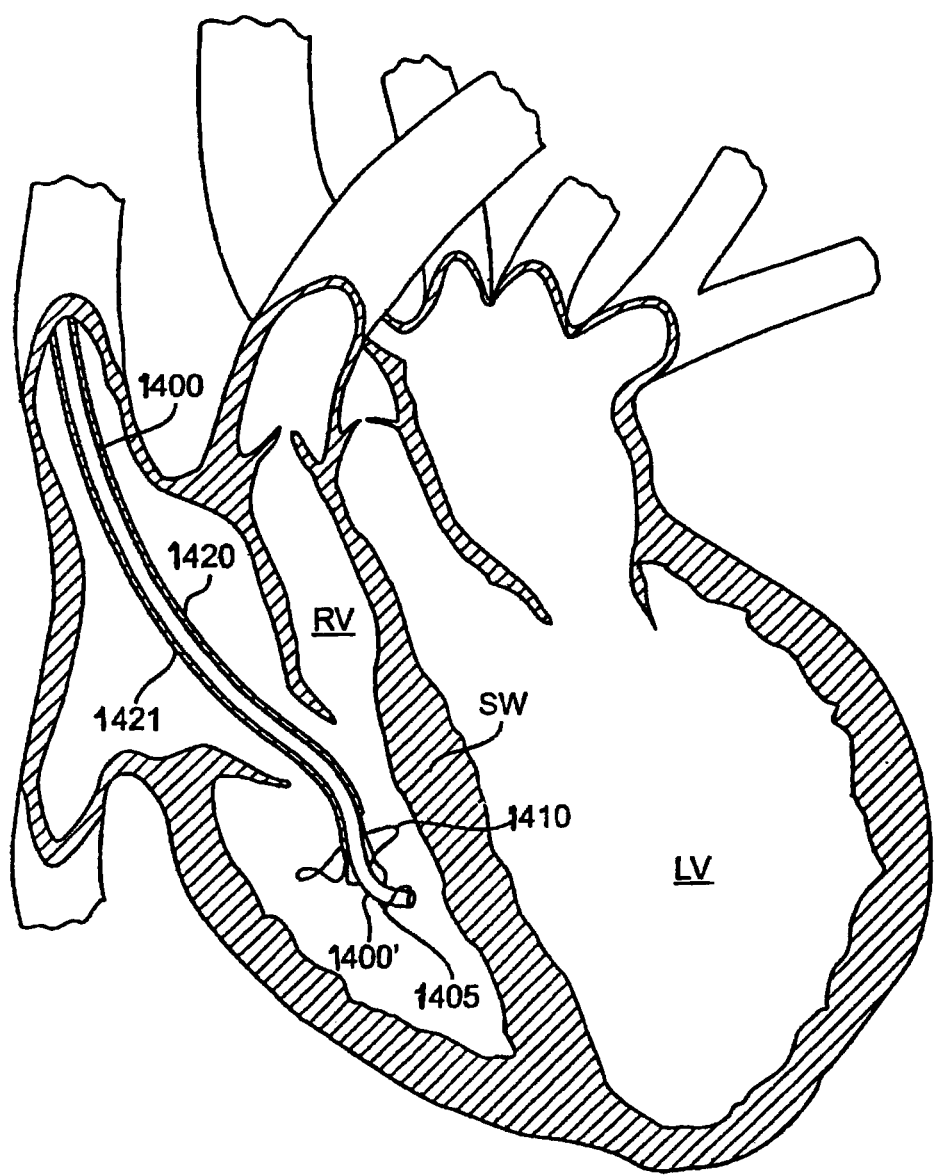
FIG. 30 is a vertical cross-sectional view of the heart showing a delivery catheter with a curved distal tip inserted into the right ventricle proximate the septal wall for delivering a splint assembly according to an aspect of the present invention.

According to the right ventricle delivery technique shown in FIGS. 8-17, a shaped guide device in the form of a delivery catheter 1100 is advanced into right ventricle RV from an access site preferably in the left or right jugular vein. Other access sites, such as, for example, the left or right subclavian vein also are contemplated. As shown in FIG. 8, the catheter 1100 has a tip portion 1101 configured to be adjustably and variably curved through the use of an adjusting pull-wire 1104. The pull-wire 1104 attaches to the distal most end of the catheter, has a portion that extends exterior the catheter at the distal end of the catheter, and then extends through the catheter to a proximal end of the catheter where it is controlled. As shown in FIGS. 8 and 9, pull wire 1104 may be an essentially straight wire that, when pulled (or tensioned), causes tip portion 1101 to curve. In another, embodiment, a pull wire may take the form of a tether, such as described below with reference to the curved catheter having pull wire 1405 in FIG. 30. Also in that embodiment, the proximal end of the pull-wire 1405 can be pulled and released to thereby cause the distal tip of the catheter to curve and to straighten as desired. Thus, the position of the catheter tip can be curved by adjusting the pull-wire and also advanced or rotated, or both, by advancing or rotating the catheter with respect to the right ventricle and septal wall.

Figure 23:
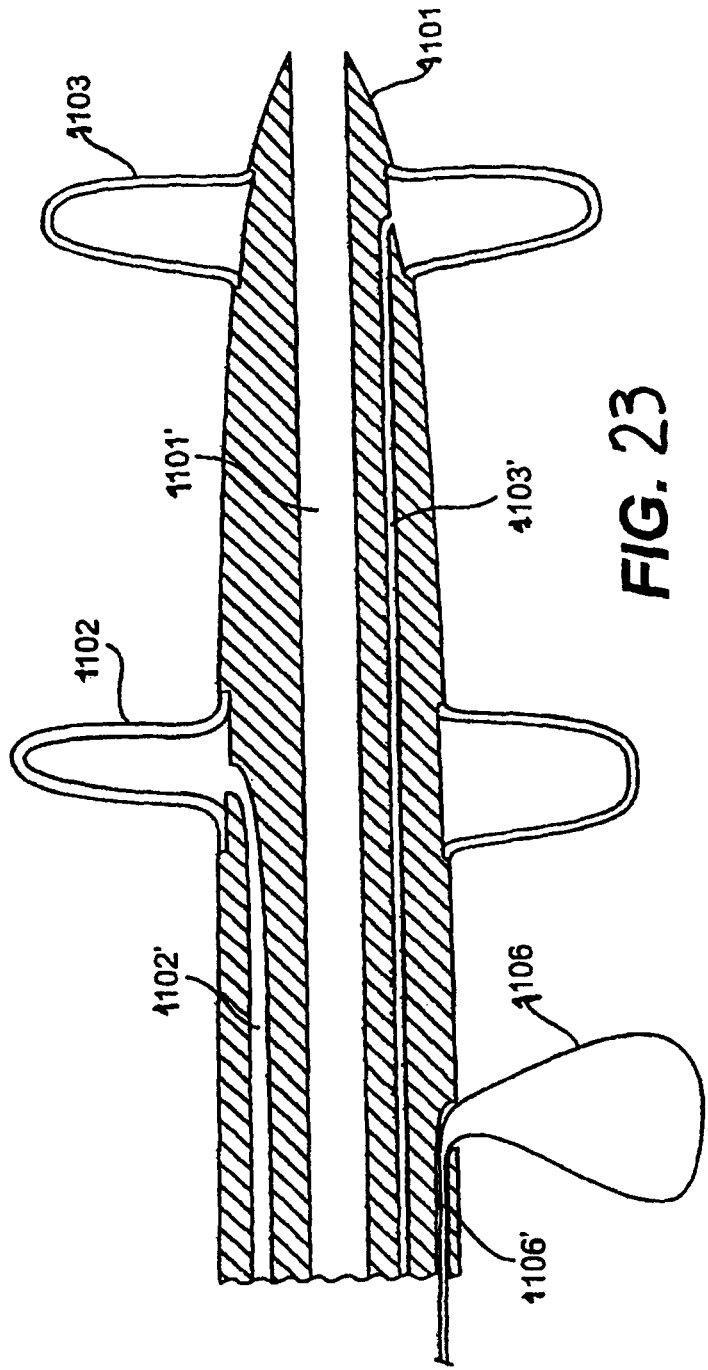
FIG. 23 is a detailed, partial side cross-sectional view of the delivery catheter of FIGS. 8-13 according to an aspect of the present invention.

Additionally, as shown best in FIG. 23, two anchoring balloons 1102, 1103 are disposed near the distal end of catheter 1100. Each balloon 1102, 1103 is in fluid communication with a corresponding inflation lumen 1102', 1103' that extends proximally to an inflating means (not shown). A lumen 1101' configured to carry a piercing needle also extends through the length of catheter 1100. In a preferred embodiment, delivery catheter 1100 additionally defines a lumen 1106' for carrying a preformed support wire 1106, which expands upon advancement of support wire 1106 relative to catheter 1100. The wire 1106 takes on a hoop-like shape which gives mechanical "back up" support to delivery catheter 1100. The support wire 1106 also helps to position the catheter 1100 within the right ventricle to allow for positioning within the right ventricle RV and with respect to the septal wall SW. The support wire 1106 is preferably made from an elastic material, such as a nickel-titanium alloy or the like, and has a preformed shape at or near a distal end of the wire configured to stabilize and position the catheter 1100. The catheter 1100 preferably also includes radiographic and echogenic markers (not shown), such as metallic or gas-filled structures, or relatively small balloons filled with a contrast media, to facilitate positioning of the catheter under fluoroscopic and/or ultrasonic guidance, such as transesophageal echo (TEE).

Figure 22:
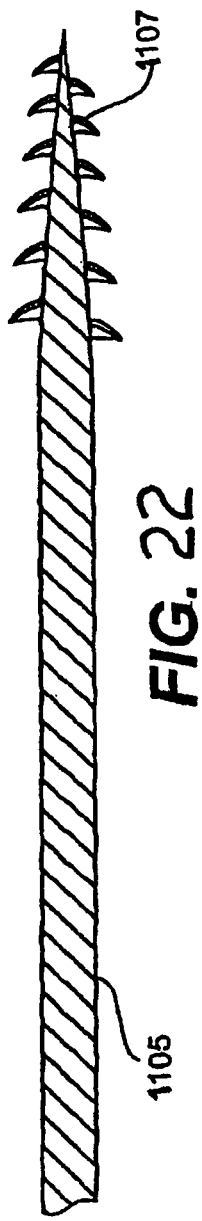
FIG. 22 is a close-up, partial side view of the guidewire of FIG. 9 according to an aspect of the present invention.

Once catheter 1100 is manipulated to a desired position on the ventricular septum SW, the support wire 1106 is advanced to stabilize the tip position, as shown in FIG. 8. A sharpened needle, or guidewire, 1105 is then advanced through the lumen in catheter 1100 and out of tip portion 1101, piercing the septal wall SW, and extending across the left ventricle chamber LV. Preferably, needle 1105 is fabricated of a highly elastic material such as, for example, nickel titanium alloy, which will allow the needle to traverse the bend at the tip of the delivery catheter, and then to straighten out for controlled traversing across left ventricle LV. FIG. 22 shows the distal portion of needle 1105 in greater detail. As can be seen from this figure, needle 1105 includes a sharpened tip which may have threads 1107 disposed around the outer surface of the tip portion. These threads 1107 preferably are flexible such that they can lay substantially flat along the length of needle 1105 as the needle traverses through the catheter lumen. Alternatively, the tip may include barbs or other similar structures that aid in anchoring the tip in the heart wall.

Once needle 1105 is across the left ventricle chamber, its position is confirmed by TEE, X-Ray, or other visualization techniques, to assure good bisection and avoidance of key mitral valve and other heart structure. Conventional angiography utilizing a "pigtail" catheter. i.e., a dye injection catheter with a loop shape at the distal end, in the left ventricle LV and angiography catheters in one or both coronary artery ostia may also be used to aid in proper positioning of the associated delivery devices in the LV. It also is important to assure that needle 1105 will not penetrate or damage any significant coronary vasculature. To assure this, an angiogram may be performed. Preferably, the angiographic image is aligned to a position that looks down the axis of the needle in the portion of the needle which traverses the left ventricle LV. This angle will limit parallax to ensure that if the tip of the needle is not coincident with a significant vessel it will not pierce such vessel. Any small variation in the position of the needle tip can be adjusted by gentle manipulation of the delivery catheter.

As mentioned above, preferably needle 1105 has soft threads 1107 disposed on the surface of a tip portion of the needle, as shown in FIG. 22. Needle 1105 can be advanced into the free wall HW of the left ventricle LV by rotating the needle, essentially causing the tip portion of the needle to be pulled or screwed into the myocardium. Threads 1107 also serve to anchor needle 1105 and provide support for the further advancement of delivery catheter 1100.

Figure 10:
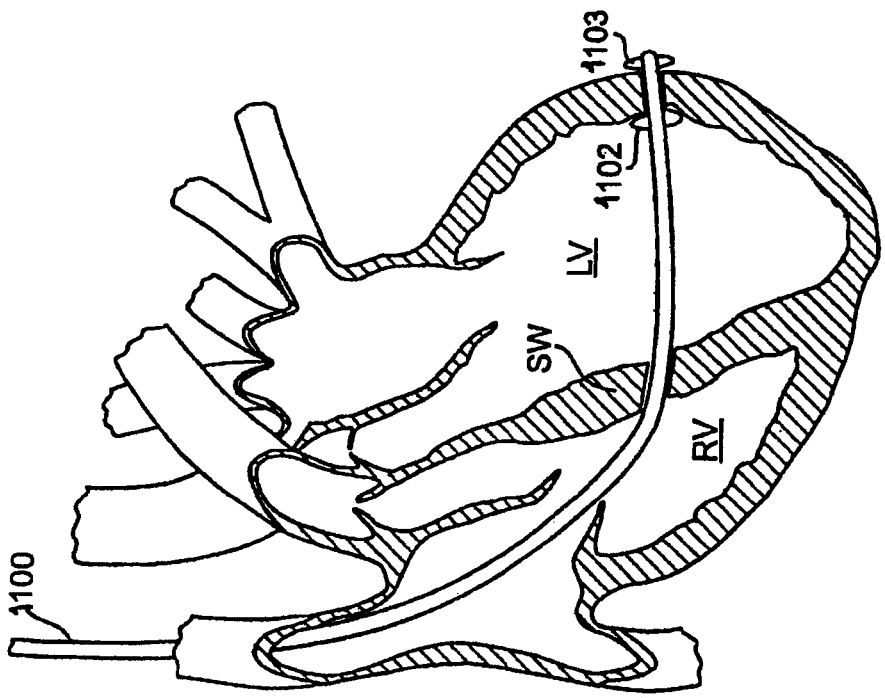
FIG. 10 is a vertical cross-sectional view of the heart showing the deliver catheter of FIG. 8 positioned over the guidewire of FIG. 9 with positioning balloons inflated on either side of the free wall according to an aspect of the present invention.

Next, delivery catheter 1100 is straightened and advanced over needle 1105 into left ventricle LV. A tapered tip 1101 on delivery catheter 1100 enables catheter 1100 to penetrate the septal and free walls SW, HW. Once distal anchoring balloon 1103 traverses across the free wall HW, both balloons 1102 and 1103 are inflated, as shown in FIG. 10, to stabilize catheter 1100 with respect to the heart chamber. Preferably, these balloons 1102, 1103 are made of an elastomeric material, such as latex or silicone, for example, to provide a relatively low profile in the non inflated state. Thus, once inflated with, for example, air or other fluid, including a radiographic contrast agent, balloons 1102, 1103 preferably have a flattened, "pancake" shape. This shape may be particularly important for distal balloon 1103, as it lies in the space between the outside of the myocardium and the pericardial sac. To further guard against damage to the pericardium or lungs, it is possible to insufflate the space between the myocardium and the pericardial sac with $CO_2$. Insufflation can occur with the use of a small lumen provided inside needle 1105. Once needle 1105 is across the myocardium, the $CO_2$ can be infused.

As delivery catheter 1100 is advanced over the distal end of needle 1105, flexible threads 1107 become collapsed and needle 1105 can be removed from catheter 1100. After removing needle 1105, an elongate tension member 1200 with a heart-engaging assembly, preferably in the form of a collapsible fixed anchor mechanism 1201 (free wall anchor), on its distal end can be inserted into the lumen of catheter 1100. Tension member 1200 is advanced until it begins to emerge from the tip portion 1101 of delivery catheter 1100, as shown in FIG. 11.

Figure 11:
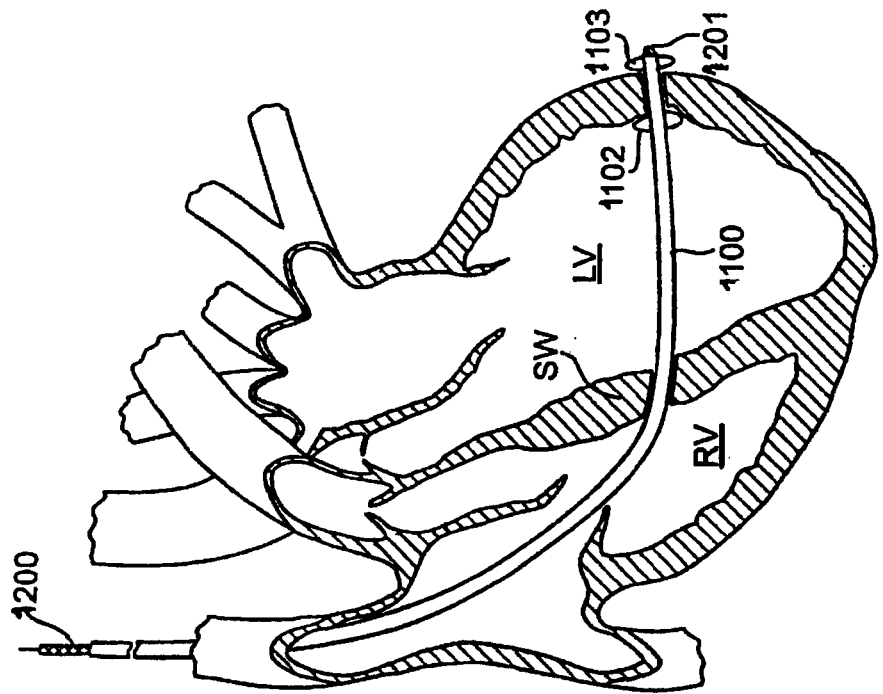
FIG. 11 is a vertical cross-sectional view of the heart showing the insertion of a tension member into the delivery catheter of FIG. 10 for placement with respect to the left ventricle according to an aspect of the present invention.
Figure 20:
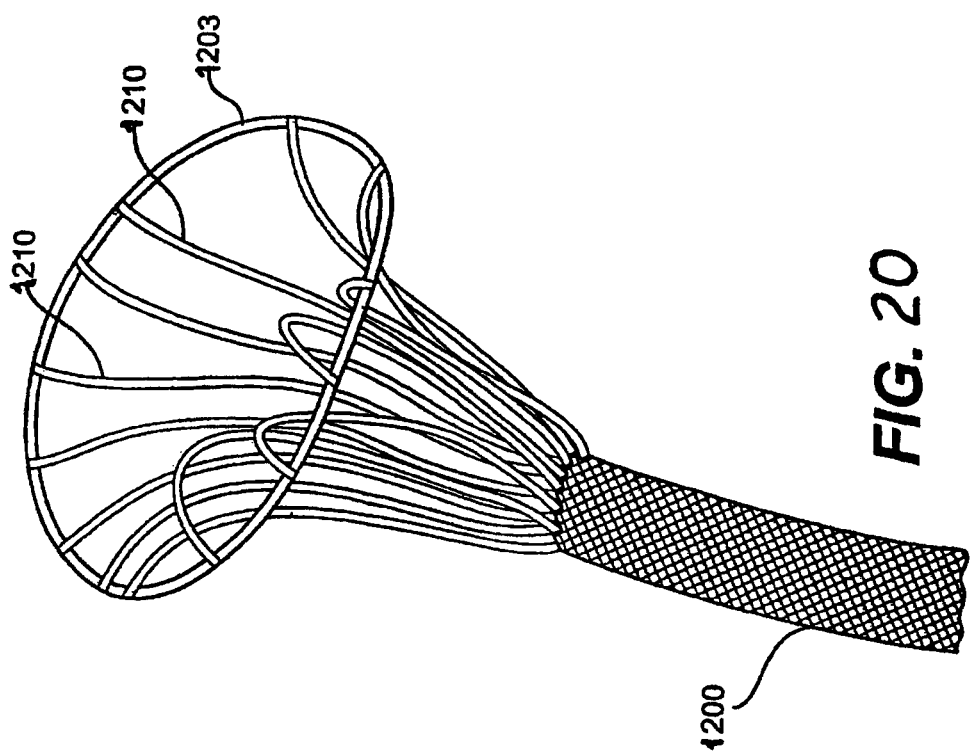
FIG. 20 is a partial perspective view of the deployable anchor and tension member of FIG. 18 prior to a securing band being placed to tighten the filament bundles on the elastic ring portion of the anchor according to an aspect of the invention.

FIG. 11 shows a preferred structure for fixed anchor mechanism 1201 in its fully expanded state after being secured with Respect to the heart wall. As shown, tension member 1200 is comprised of a braided polymer, such as that disclosed in the '049 application incorporated by reference above. A cover of expanded polytetrafluoroethylene (ePTFE) (not shown) preferably covers the majority of the length of tension member 1200. Each bundle 1210 in the braid structure is attached via suturing, adhesive, or other suitable attachment mechanism, to a flexible elastic ring 1203. Ring 1203 preferably is comprised of nickel titanium, or an elastomeric polymer such as silicone or urethane, or other suitable like materials. This attachment of the bundles to the ring is best shown in FIG. 20. In order to facilitate bundles 1210 of the braid to be attached to ring 1203, the braided structure transitions from a tight woven braid to a region that is primarily unbraided at a position slightly proximal to the ring.

In this configuration, flexible elastic ring 1203 can be easily deformed into a flattened hoop, without bundles 1210 inhibiting this deformation. This is the configuration that tension member 1200 has as it is advanced through the lumen of delivery catheter 1100. To allow tension member 1200 to be pushed through catheter 1100, a stiffening mandrel may be disposed either inside or adjacent the braided portion of the tension member.

Figure 12:
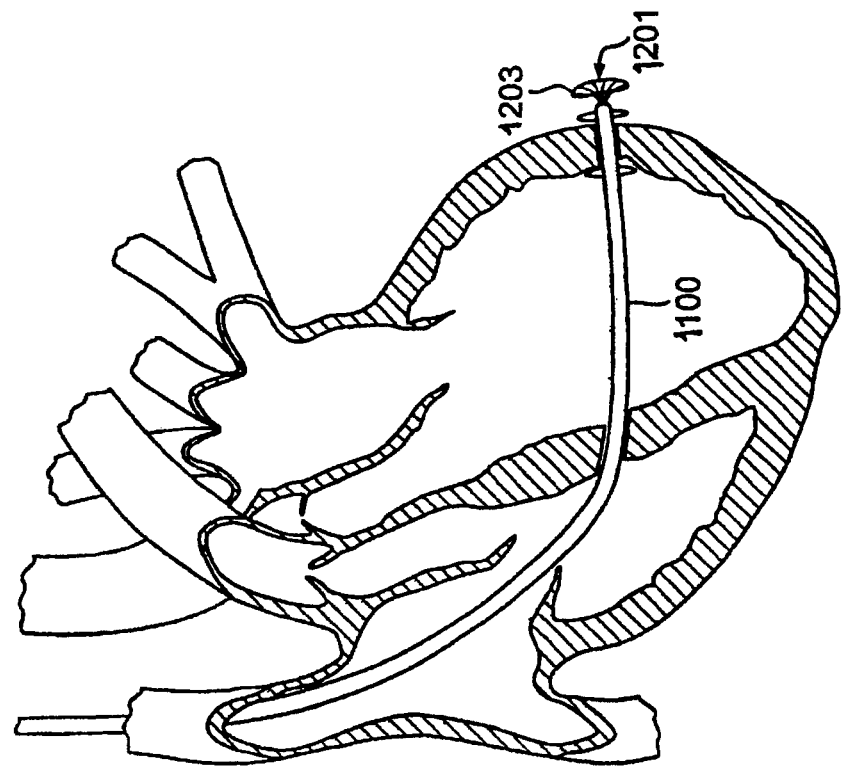
FIG. 12 is a vertical cross-sectional view of the heart showing a deployed fixed anchor on the distal end of the tension member of FIG. 11 after being extended past the distal end of the delivery catheter according to an aspect of the present invention.
Figure 19:
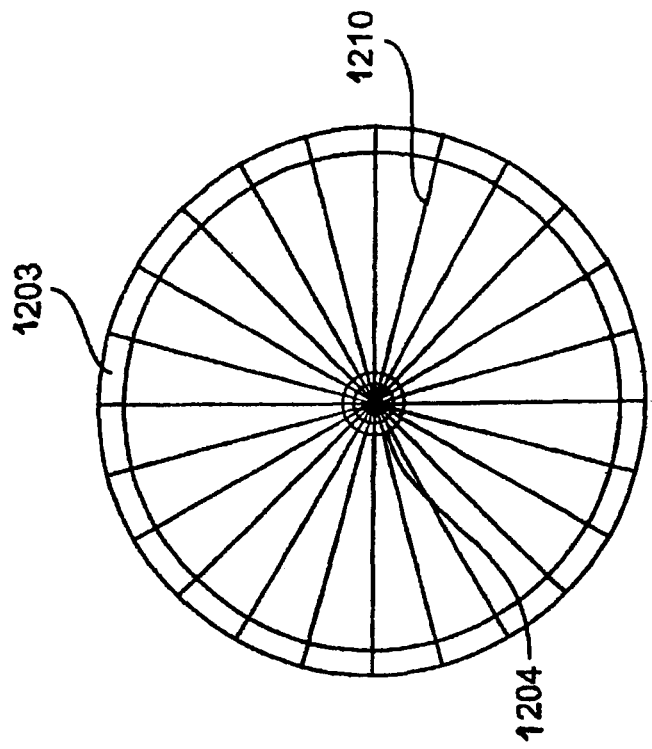
FIG. 19 is a top view of the anchor of FIG. 18 according to an aspect of the invention.
Figure 18:
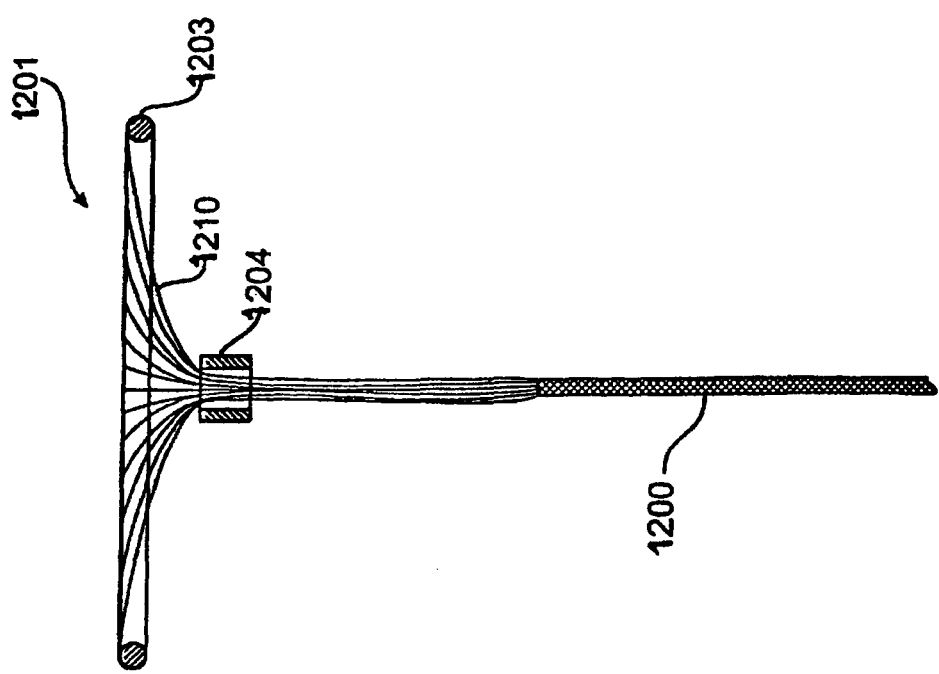
FIG. 18 is a partial side view of the deployable anchor and tension member of FIGS. 12 and 13 according to an aspect of the present invention.
Figure 21:
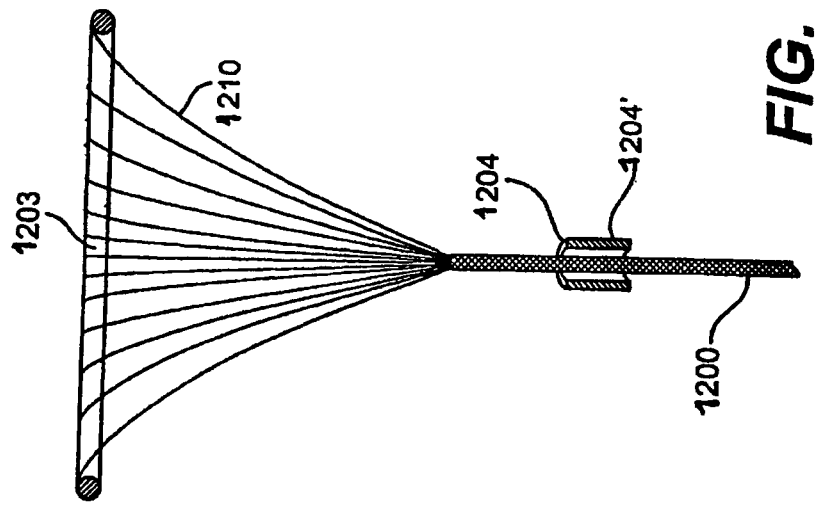
FIG. 21 is a partial side view of the anchor and tension member of FIG. 18 showing the placement of the securing/tightening band according to an aspect of the present invention.

As shown in FIG. 12, tension member 1200 is advanced until flexible ring 1203 fully emerges from the lumen of delivery catheter 1100. As such, anchor mechanism 1201 has sufficient strength to serve as an anchor and allows bundles 1210 to take on a funnel shape, as shown in FIG. 20. To tighten fiber bundles 1210, a securing band 1204 (FIG. 21) is advanced along the outside of braided tension member 1200, until the bundles tighten into a generally spoke like configuration, as shown in FIGS. 18 and 19. A flexible pushing tube (not shown), or other suitable mechanism, may be used to advance securing band 1204. Securing band 1204 preferably has circumferential ribs 1204' on its inner surface that are oriented proximally, as shown in FIG. 21. Ribs 1204' allow for the band 1204 to be advanced distally, while preventing proximal slipping. Once positioned, the securing band 1204 maintains anchor mechanism 1201 in a relatively flat profile, as shown in FIG. 18.

Figure 13:
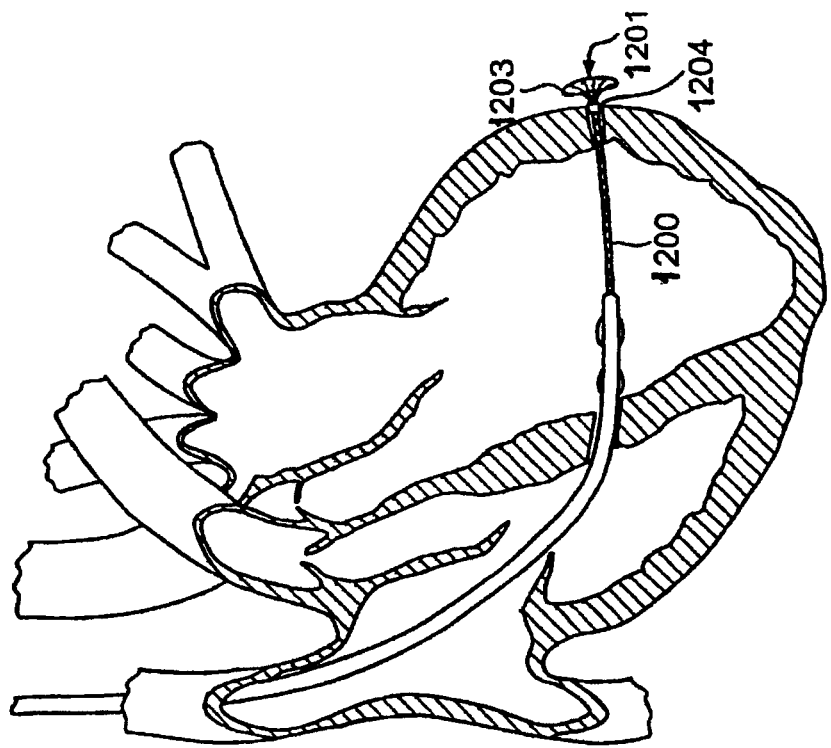
FIG. 13 is a vertical cross-sectional view of the heart showing the removal of the delivery catheter from the tension member of FIG. 12 according to an aspect of the present invention.

FIG. 13 shows tension member 1200 and fixed anchor 1201 in a fully deployed configuration with respect to the heart. After fixed anchor 1201 of tension member 1200 is deployed, anchor balloons 1102, 1103 on delivery catheter 1100 are deflated, and the delivery catheter is removed from tension member 1200 and out of the heart.

Figure 14:
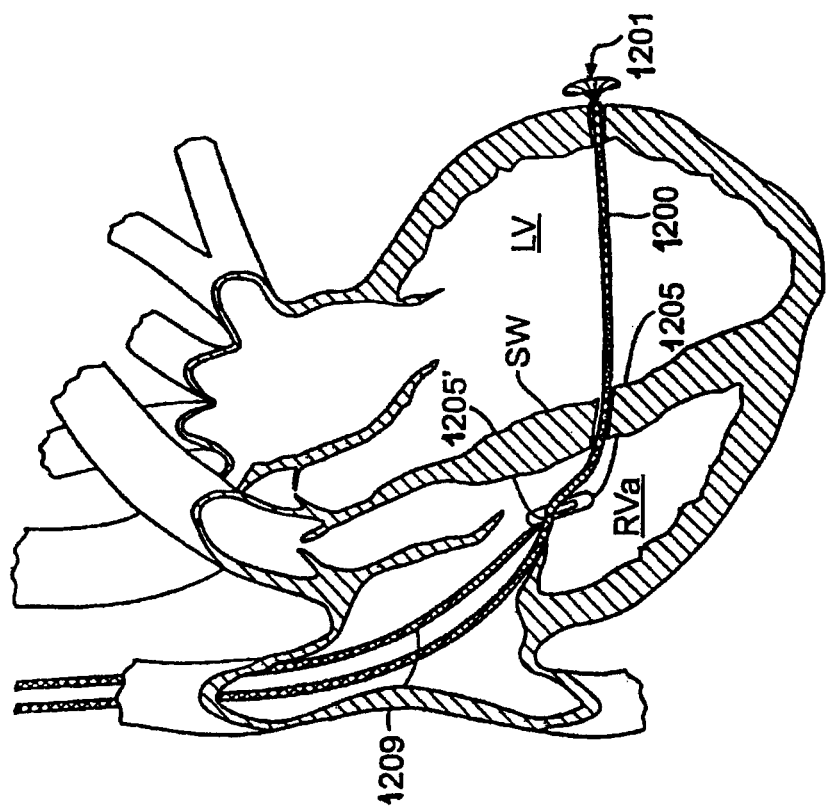
FIG. 14 is a vertical cross-section of the heart showing the delivery of an adjustable anchor to be placed on the tension member of FIG. 13 adjacent the septal wall according to an aspect of the present invention.

After removing delivery catheter 1100, a second heart-engaging assembly, preferably in the form of an adjustable anchor pad 1205 (septal wall anchor) is advanced over tension member 1200 using a deployment tool 1209, as shown in FIG. 14. Adjustable anchor pad 1205 is similar in many ways to the adjustable pad assembly and deployment mechanism disclosed in the '049 application incorporated above, as will be explained. Thus, there preferably is an actuatable staple mechanism within the pad structure for securing pad 1205 to braided tension member 1200. In accordance with the present invention, however, pad 1205 preferably has an oval, as opposed to circular, configuration. Such an oval configuration facilitates introduction of the pad into the access site in the vasculature. Moreover, a through hole 1205' extending through this pad is angled relative to the pad surface, to allow pad 1205 to be oriented in a more parallel fashion to the tension member 1200 as it is advanced along the tension member 1200, as shown in FIG. 14.

Adjustable pad 1205 is advanced using deployment tool 1209 over tension member 1200 in essentially a "monorail" fashion, allowing anchor pad 1205 to be oriented substantially adjacent and parallel to tension member 1200 as tension member 1200 slides through throughhole 1205'. Once located at the septal wall SW, a tightening device 1206, preferably in the form of a tube, is advanced over the outside of the tension member until the distal end of the tightening device 1206 engages the adjustable pad 1205. Manipulation of the tightening device 1206 relative to tension member 1200 positions adjustable pad 1205 and tension member 1200 into a position so as to alter the shape of the left ventricle LV.

Once a desired amount of shape change is achieved, adjustable pad 1205 is deployed by manipulation of the deployment tool 1209, in a manner similar to the technique disclosed in the '049 application. That is, the deployment tool 1209 includes an actuator wire that is pre-engaged with an engagement collar (not shown) in adjustable pad assembly 1205 such that when the actuator wire is pulled, the engagement collar travels through various channels disposed within the adjustable anchor pad 1205. The engagement collar causes securement members, preferably in the form of pins or staples, such as staple 1218 shown in FIG. 17, to move within the pad to engage with the braided tension member structure running through the pad. A more detailed description of the tightening of the splint assembly and the securing of the adjustable pad on the tension member can be found in the '049 application incorporated herein by reference.

Figure 16:
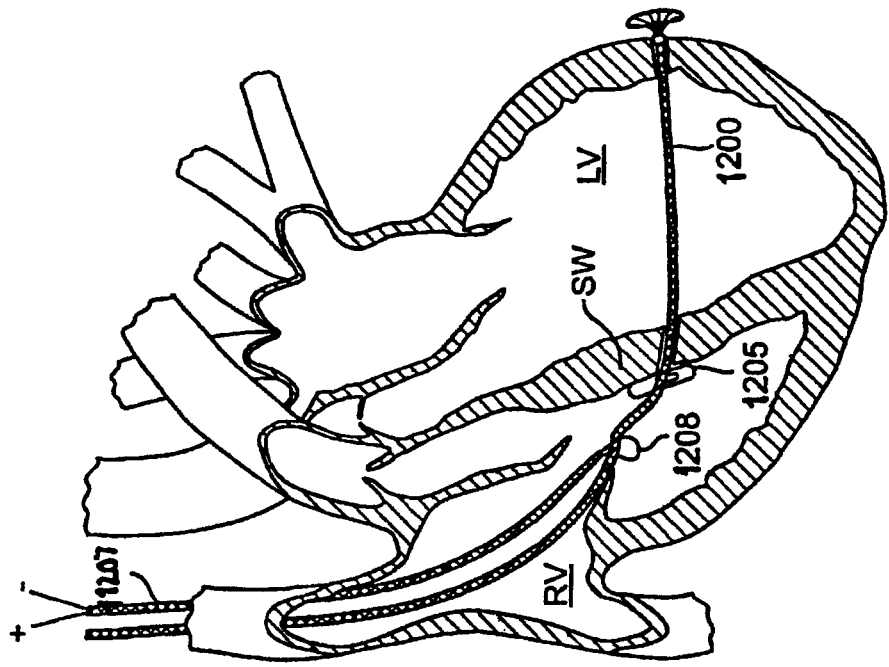
FIG. 16 is a vertical cross-section of the heart showing a cutting snare inserted into the right ventricle to cut excess tension member length from the splint assembly of FIG. 15 according to an aspect of the present invention.

FIG. 16 shows adjustable pad 1205 secured onto tension member 1200 adjacent septal wall SW within right ventricle RV after the tightening device 1206 and the deployment tool 1209 have been removed. A trimming catheter 1207 containing a wire in a snare like loop 1208 is advanced along the excess length of tension member 1200 to a position proximate the secured adjustable pad 1205. Preferably, the wire forming snare-like loop 1208 can be heated such that upon retraction of snare loop 1208 within the lumen of catheter 1207, the excess length of tension member 1200 is thermally severed and can be removed. The wire loop may also have a sharpened edge along its inside periphery to cut tension member 1200 as loop 1208 is retracted into catheter 1207. Other suitable cutting mechanisms may be used and are contemplated as within the scope of the invention.

Figure 17:
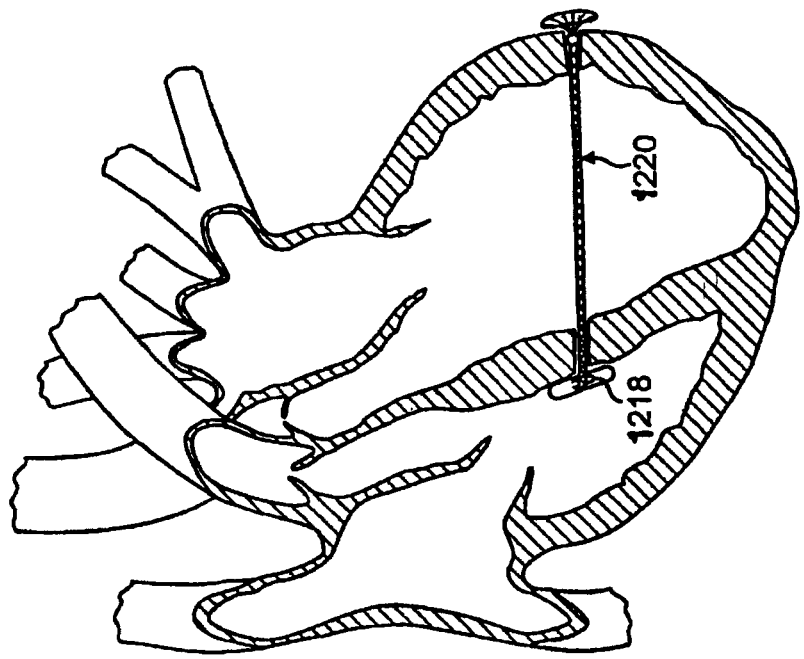
FIG. 17 is a vertical cross-section of the heart showing a splint assembly positioned with respect to the left ventricle according to an aspect of the present invention.
Figure 44:
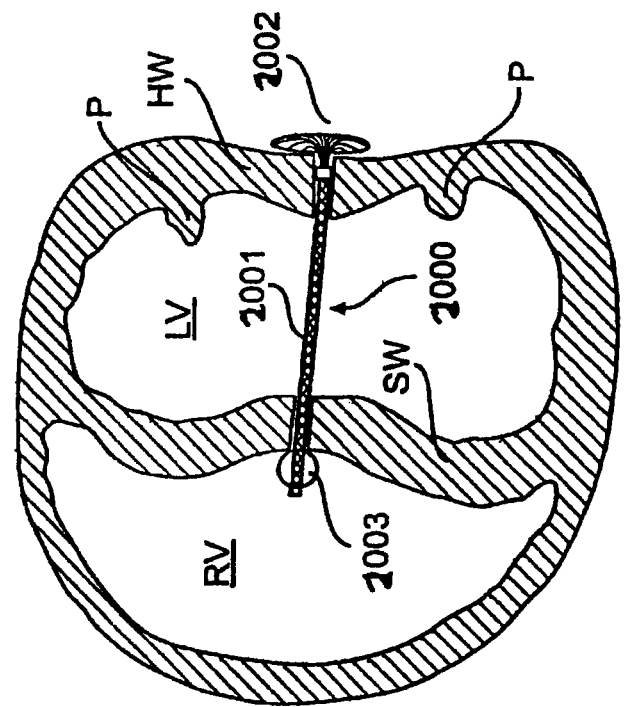
FIG. 44 is a transverse cross-sectional view of the heart showing a splint assembly placed with respect to the heart to treat a mitral valve according to an aspect of the present invention.

FIGS. 17 and 44 show fully deployed splints 1220, 2000 in position with respect to the left ventricle LV of the heart. Following the steps discussed above, additional splints may be positioned as needed or desired in the left ventricle LV or other chambers of the heart, including near the mitral valve to help improve valve function, as disclosed elsewhere herein. In a preferred method, three splints are positioned in a spaced, approximately parallel relationship from positions on the ventricular septum SW to positions on the ventricular free wall HW. Preferably, the splints are oriented perpendicular to the long axis of the left ventricle, as shown in FIGS. 17 and 44.

Once all the desired splints are positioned, the access site in the vasculature is closed by conventional means, such as sutures and the like.

In another embodiment of the invention, splints can be positioned across the left ventricle via an endovascular route leading directly into the left ventricle rather than through the right ventricle. Using this approach, preferably the access site is located in one of the femoral arteries, in a manner similar to many cardiology procedures, for example. Although this route requires advancing delivery tools retrograde across the aortic valve, this delivery route permits the delivery catheter to be placed in approximately the middle of, rather than outside, the left ventricle, thus yielding a more symmetrical approach. The ability to position the splint to achieve a good bisection of the left ventricle therefore may be enhanced since the bisection may be easier to visualize prior to implanting the splints. Furthermore, it may be possible to stabilize the delivery system using walls on both sides of the left ventricle, thus requiring fewer additional support mechanisms.

Figure 24:
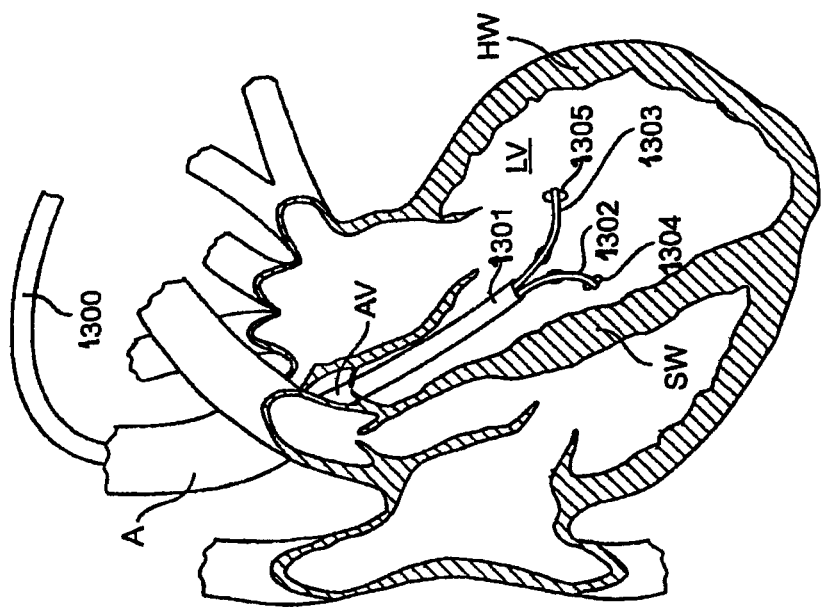
FIG. 24 is a vertical cross-sectional view of a heart showing a delivery catheter with two curved catheters inserted endovascularly through the aorta into the left ventricle according to an aspect of the present invention.

The direct left ventricle delivery approach uses a guide device, preferably in the form of a delivery catheter, of a different structure than that used in the right ventricle delivery approach. As shown in FIG. 24, a delivery catheter 1300 for the left ventricle delivery approach is positioned in the left ventricle LV from the aorta A, with access through the femoral artery. Delivery catheter 1300 includes a main catheter 1301 and two curved catheters 1302, 1303 extending from main catheter 1301 and configured to curve in substantially opposite directions to one another. Main catheter 1301 defines two side by side lumens (not shown) extending along the length of the catheter. Each curved catheter 1302, 1303 is disposed inside a respective lumen of catheter 1300 and is capable of moving relative to main catheter 1300 within the lumen. Curved catheters 1302, 1303 each have two anchoring balloons disposed near their distal ends and lumens in fluid communication with each balloon to facilitate inflation, in a manner similar to that described with respect to the right ventricle delivery catheter shown in FIG. 23. Curved catheters 1302, 1303 are independently manipulable, both in axial translation and in rotation relative to the main catheter. Moreover, it is contemplated that curved catheters 1302, 1303 can have the form of the adjustably curvable catheters discussed with reference to FIGS. 8 and 30. That is, it is contemplated that a pull-wire could be used to independently and adjustably curve the end portions of each catheter, thereby allowing for more control over the curve of the tip portion of each catheter.

Figure 25:
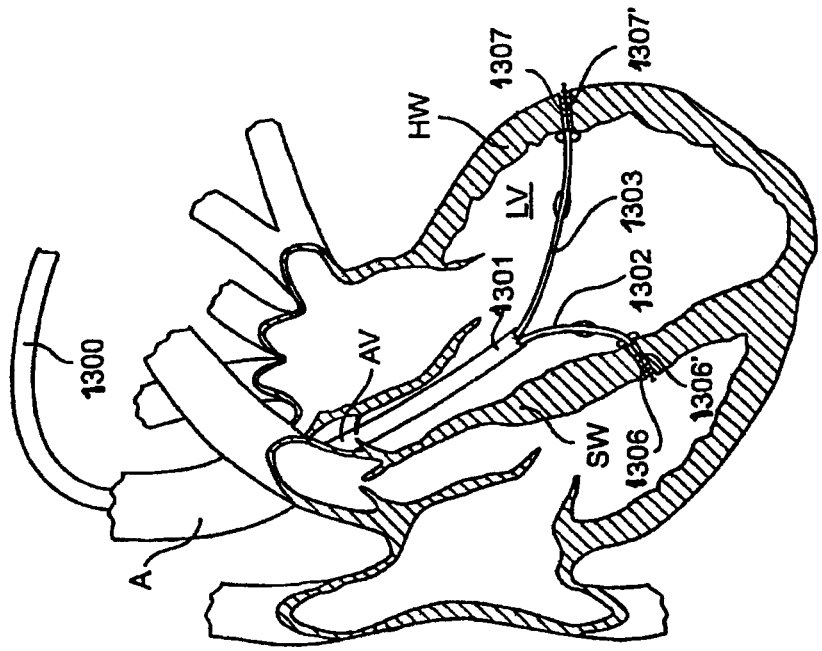
FIG. 25 is a vertical cross-sectional view of a heart showing the curved delivery catheters of FIG. 24 with inflated distal balloons respectively in contact with the free wall and septal wall of the heart and with sharpened wires respectively extending through the free wall and septal wall of the heart according to an aspect of the present invention.

Once the distal tip of main catheter 1301 resides in the left ventricle LV, curved catheters 1302, 1303 are advanced with their respective distal anchoring balloons 1304, 1305 inflated. Distal balloons 1304, 1305 serve to act as protective bumpers on the curved catheters so as to avoid damaging various heart structures as the catheters traverse the ventricle. The curvature of catheters 1302, 1303 causes the tips of the catheters to deflect laterally until the distal balloons 1304, 1305 of each catheter 1302, 1303 contact the inside surface of the left ventricle LV, at the septal wall SW and free wall HW, respectively. Once positioned, the curved catheters press against each other to form a self-supporting structure which remains in place during the beating of the heart. Once distal balloons 1304, 1305 contact the walls, sharpened wires 1306, 1307, similar to the one described above in the right ventricle delivery method and shown in detail in FIG. 22, are advanced into the myocardium, as shown in FIG. 25. As with the right ventricle delivery method, catheters 1302, 1303 are manipulated under ultrasonic and/or fluoroscopic guidance until the tips of the curved catheters are in a desired position on the free wall and septal wall for splint attachment. This permits a good bisection of the left ventricle LV and the avoidance of significant coronary structure. As discussed above, a "pigtail" catheter may also be used to help visualization and positioning of the devices, preferably with a diagnostic catheter in the coronary ostia. As with the wire used for the right ventricle approach, sharpened wires 1306, 1307 also have soft, preferably polymeric, threads 1306', 1307' disposed on their surfaces around their distal ends, to allow for screwing into the myocardium.

Curved catheters 1302, 1303 then are advanced with both anchor balloons deflated over wires 1306, 1307, similar to the step described above in the right ventricle approach. After catheters 1302, 1303 have been advanced across the ventricular walls SW, HW at the appropriate positions, both balloons on each of curved catheters 1302, 1303 are inflated to keep the catheters securely positioned and stabilized with respect to the chamber walls, as shown in FIG. 26.

Figure 26:
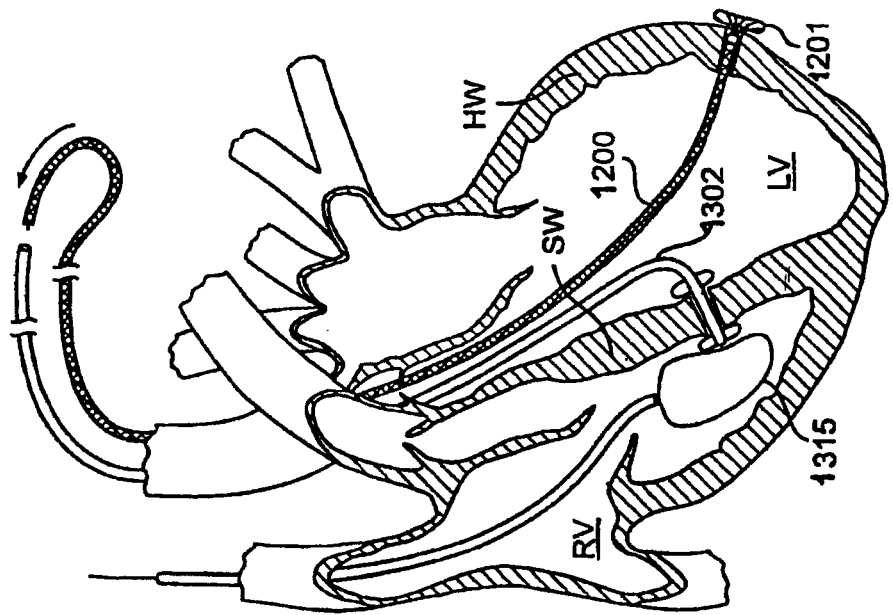
FIG. 26 is a vertical cross-sectional view of a heart showing a tension member delivered through the curved delivery catheter contacting the free wall of FIG. 25 according to an aspect of the present invention.
Figure 27:
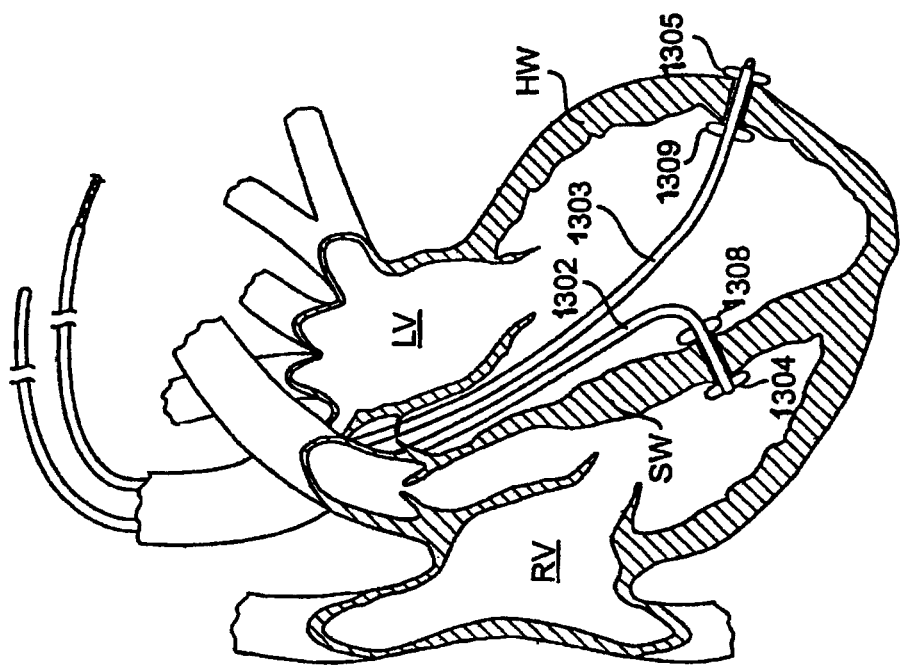
FIG. 27 is a vertical cross-sectional view of a heart showing the curved catheter contacting the free wall of FIG. 25 removed from the patient and the tension member being fed into a proximal end of the curved catheter contacting the septal wall of FIG. 25 according to an aspect of the present invention.

A tension member 1200, with a first heart-engaging assembly, preferably in the form of a deployable fixed anchor pad mechanism 1201 (free wall anchor), on its distal end, similar to the tension member and deployable fixed pad mechanism discussed with respect to the right ventricle delivery method, is inserted into curved catheter 1303 engaging the free wall HW, as shown in FIGS. 26 and 27. Fixed pad 1201 deploys in a manner similar to that of the right ventricle delivery approach. After fixed pad 1201 is deployed, curved catheter 1303 is removed, as shown in FIG. 27. The free end of tension member 1200 opposite to the end on which fixed pad 1201 is secured is inserted into the proximal end of curved catheter 1302 that is engaged with septal wall SW. Tension member, 1200 is then advanced through the lumen of catheter 1302 until it extends out of the distal end of the catheter and into right ventricle RV. A conventional snare 1315, for example with a wire loop on its distal end, may be positioned in the right ventricle through an access site, preferably in a jugular vein, for example. As the free end of tension member 1200 emerges from curved catheter 1302 and into right ventricle RV, snare 1315 captures tension member 1200 and pulls tension member 1200 out of right ventricle RV and out of the patient's body.

Figure 29:
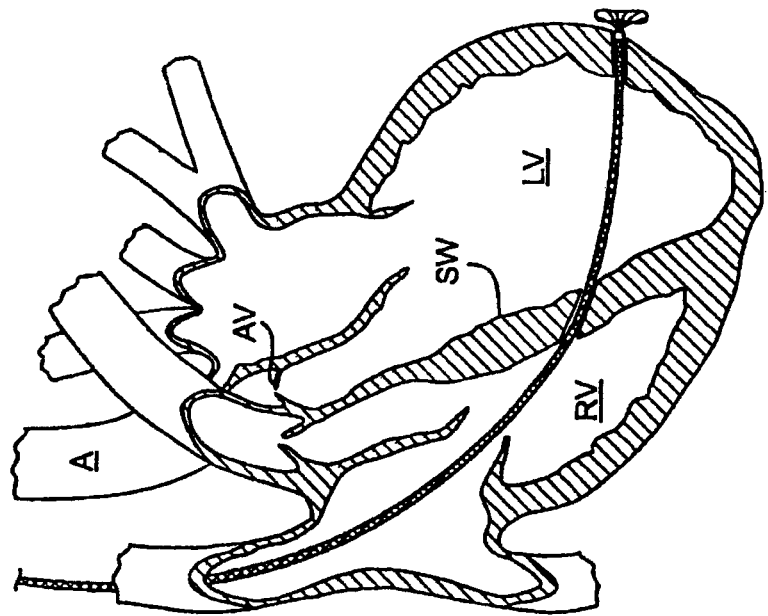
FIG. 29 is a vertical cross-sectional view of the heart showing the tension member of FIG. 28 extended across the left ventricle after the curved delivery catheter of FIG. 28 has been removed according to an aspect of the present invention.
Figure 28:
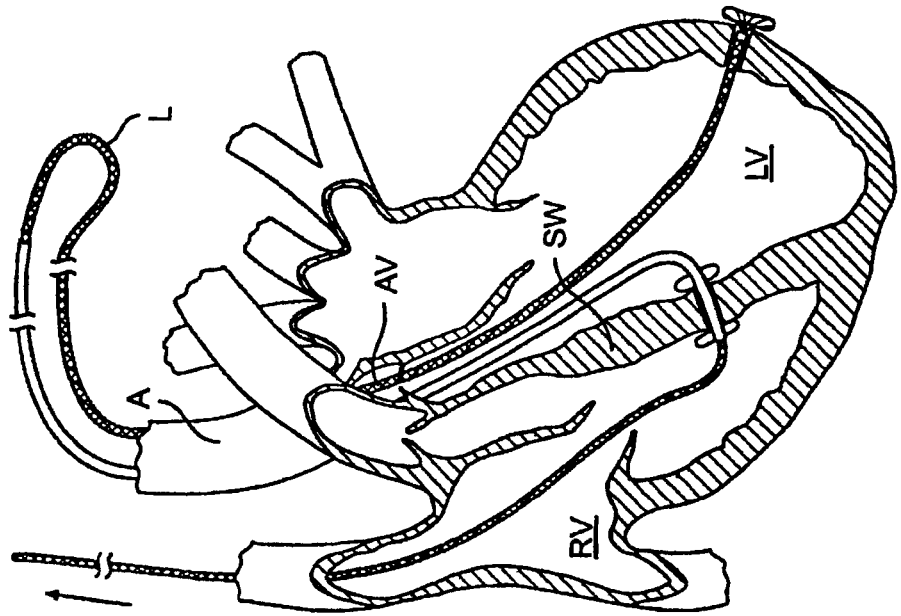
FIG. 28 is a vertical cross-sectional view of the heart showing the tension member of FIG. 27 being advanced through the curved catheter, through the septal wall, into the right ventricle and out of the heart according to an aspect of the present invention.

FIG. 28 shows tension member 1200 after the free end has been snared and pulled out of the jugular vein access site. Tension member 1200 preferably is long enough to allow for the withdrawal of catheter 1303 that engages the free wall HW, the re-advancement of tension member 1200 into catheter 1302 that engages the septal wall SW, and the withdrawal of tension member 1200 out of the right ventricle RV and the access site. Additionally, the proximal loop extending out the femoral access site (shown in FIG. 27) must still have enough length for the second catheter to be withdrawn. As second catheter 1302 is withdrawn out of the femoral access site and over tension member 1200 secured to the free heart wall, it preferably is removed from the tension member by skiving the length of the catheter down the lumen containing the tension member. FIG. 29 shows tension member 1200 after curved catheter 1302 has been fully removed.

At this point, tension member 1200 is in a configuration similar to that shown in FIG. 14, and the technique described with reference to the right ventricle approach above to deliver and secure a second heart-engaging assembly, preferably in the form of an adjustable anchor pad (septal wall anchor), onto tension member 1200 adjacent the septal wall SW to finish the splint deployment across the left ventricle LV can be used. Thus, the left ventricle delivery method and right ventricle delivery method differ only up to the point of delivery of the adjustable pad, and after that the steps may be the same.

FIGS. 30-37 illustrate yet another embodiment of a method for delivering and implanting a splint across the left ventricle from a free wall HW to a septal wall SW. The method shown in these figures is similar in many respects to the right ventricle delivery technique described above. However, the method to be described differs from the previously discussed right ventricle approach in that the splint is advanced across the left ventricle LV over a small hollow guidewire or needle of the type shown in FIGS. 31-34. Additionally, an alternative free wall deployable anchor structure is described.

In FIG. 30, a guide device, again preferably in the form of a delivery catheter 1400, is positioned in the right ventricle RV from an access point, such as, preferably the right jugular vein, for example. Delivery catheter 1400 has a similar structure as delivery catheter 1100 used in the right ventricle delivery technique described above. However, delivery catheter 1400 does not advance into and across the left ventricle LV, as did delivery catheter 1100. Catheter 1400 has a curved distal tip portion 1400'. A tether, or pull-wire, 1405 connected to distal tip portion 1400' is configured to adjust the angle or curvature of the tip portion 1400'. Tether 1405 runs inside a lumen 1420 disposed adjacent catheter 1400, or, alternatively, within catheter 1400. Pulling proximally on tether 1405 causes tip portion 1400' to deflect laterally. Delivery catheter 1400 also includes a pre formed support wire 1410 configured to extend via advancement of the support wire from another lumen 1421 disposed adjacent catheter 1400 on a side substantially opposite to the side lumen 1420 is. Support wire 1410 not only assists to maintain the placement of tip portion 1400' of delivery catheter 1400 within right ventricle RV in the appropriate position, but also assists in positioning the tip portion 1400' near the center of right ventricle RV relative to the anterior and posterior ends of the right ventricle, as a result of the shape and size of the support wire. Alternative shapes of the pre formed support wire also are contemplated which would facilitate tip positioning and support in other desired positions within right ventricle RV.

Figure 31:
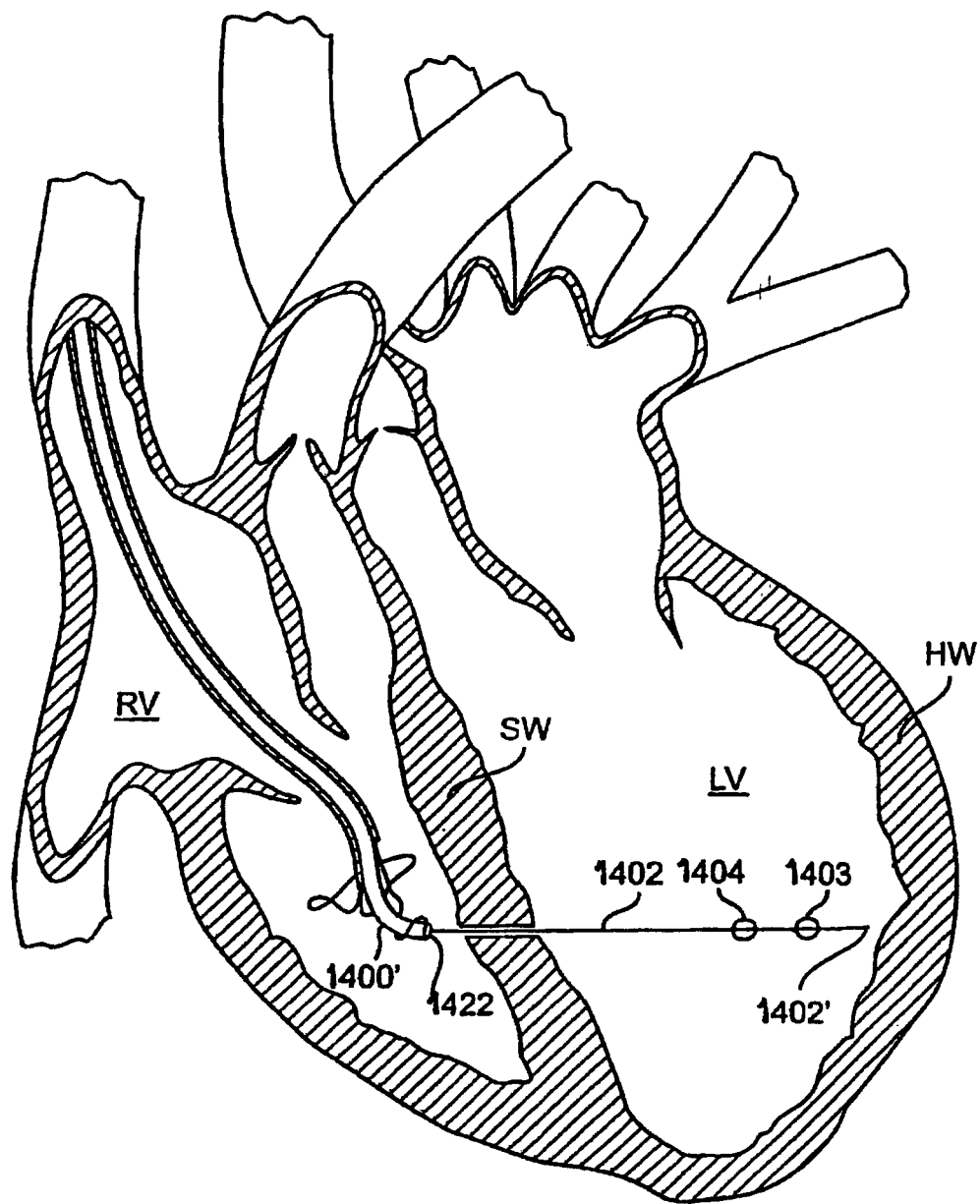
FIG. 31 is a vertical cross-sectional view of the heart with a guidewire with inflated balloons on a distal end extending from the delivery catheter of FIG. 30, through the septal wall, and across the left ventricle according to an aspect of the present invention.

After tip portion 1400' of delivery catheter 1300 is positioned and oriented in the desired location with respect to septal wall SW, a hollow sharpened metallic guidewire, or needle, 1402 is advanced through a central lumen 1422 of delivery catheter 1400, across the ventricular septum SW, and across the left ventricular chamber LV to free wall HW, as shown in FIG. 31. As with the methods described above, a combination of fluoroscopic and ultrasonic imaging are performed to assist in the guidance and confirmation of positioning for this delivery technique. Appropriate radiographic or other suitable visible markers are positioned on the devices to facilitate this imaging, as described above.

Hollow guidewire 1402 has a sharpened tip 1402' and defines a central lumen plugged near tip 1402'. The material used to make guidewire 1402 preferably includes a superelastic nickel titanium alloy, or other similar like material. Two elastomeric balloons, a distal balloon 1403 and a proximal balloon 1404, are secured near the distal end of guidewire 1402 slightly proximal to sharpened tip 1402'. Distal balloon 1403 is in flow communication with central lumen 1422 of guidewire 1402. Proximal balloon 1404 is in fluid communication with an additional tube (not shown) positioned inside hollow guidewire 1402. In this manner, each balloon 1403, 1404 can be independently inflated and deflated as required.

Balloons 1403, 1404 preferably are in a deflated condition as they are advanced across septal wall SW and then are inflated during advancement across the left ventricle LV. Inflating the balloons during advancement across the left ventricle LV may assist in visualizing the advancement path of the guidewire. To assist in such visualization, preferably the balloons are inflated with a radiographic contrast agent. The ability to visualize the advancement path of guidewire 1402 may prevent damage to various cardiac structure as well as assist in ensuring proper positioning of the guidewire on the free wall HW.

Figure 32:
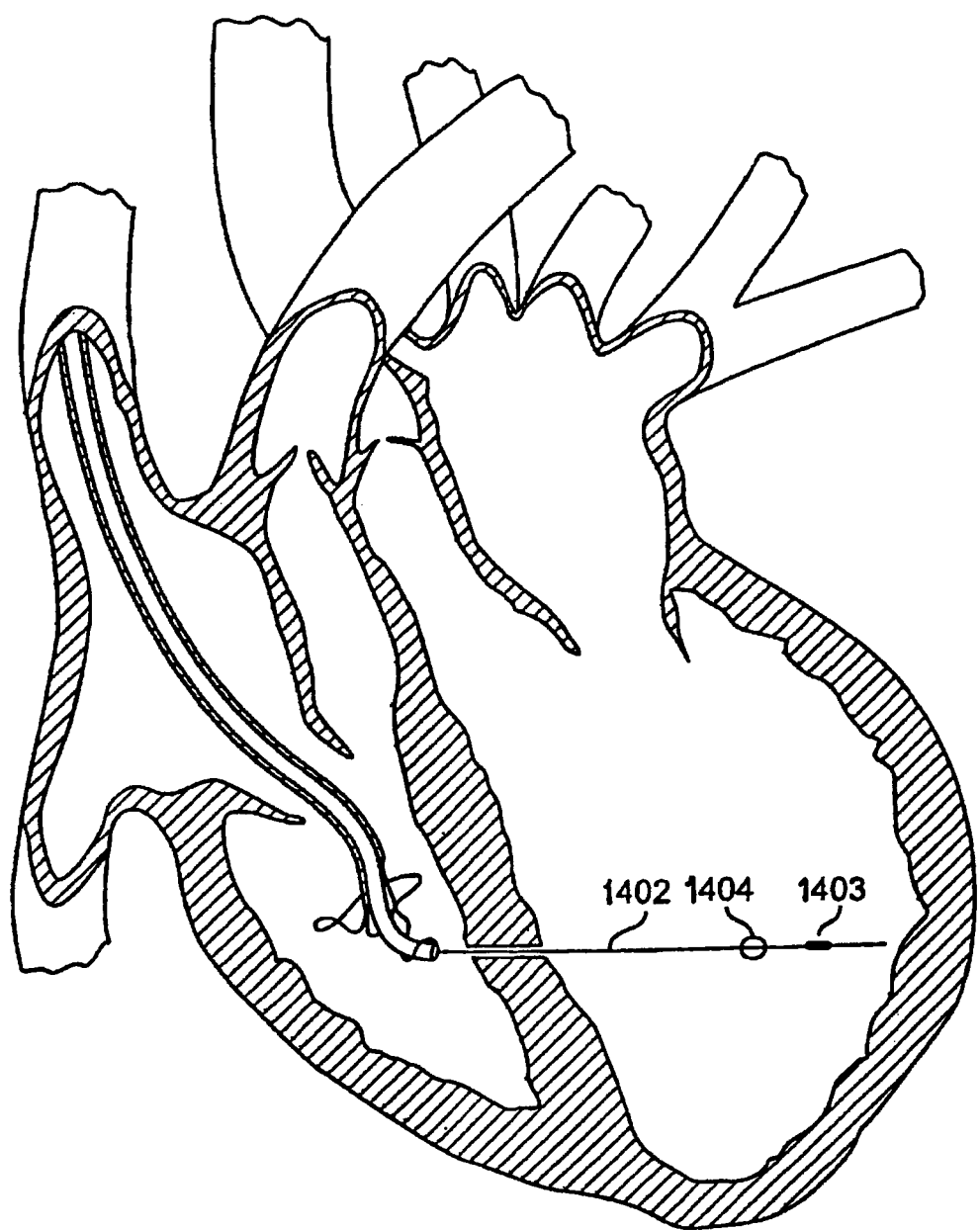
FIG. 32 is a vertical cross-sectional view of the heart showing the guidewire of FIG. 31 with the distal balloon deflated and about to be advanced through the free wall of the left ventricle according to an aspect of the present invention.
Figure 33:
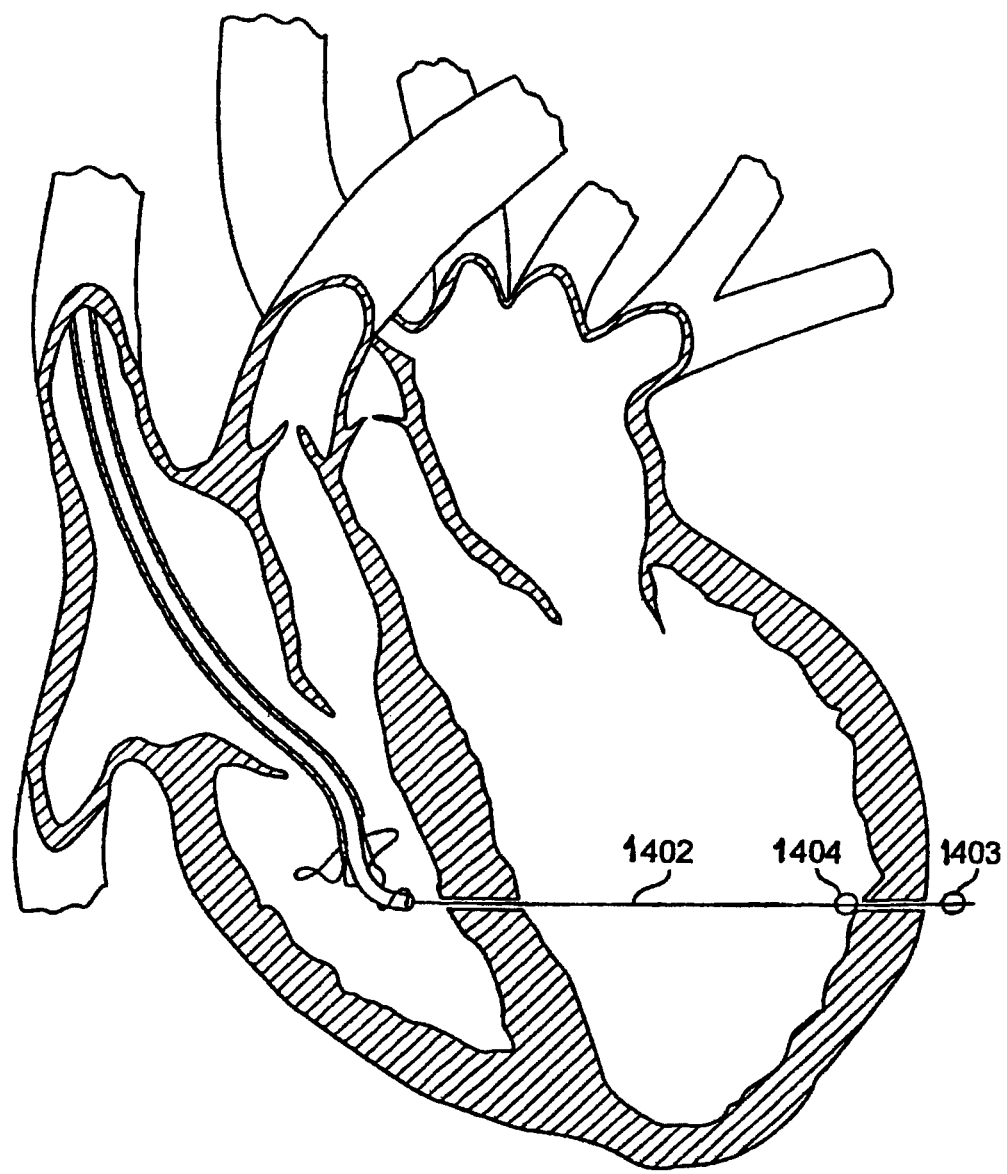
FIG. 33 is a vertical cross-sectional view of the heart showing the guidewire of FIG. 32 advanced through the free wall until the proximal inflated balloon abuts the inside of the free wall and with the distal balloon inflated according to an aspect of the invention.
Figure 34:
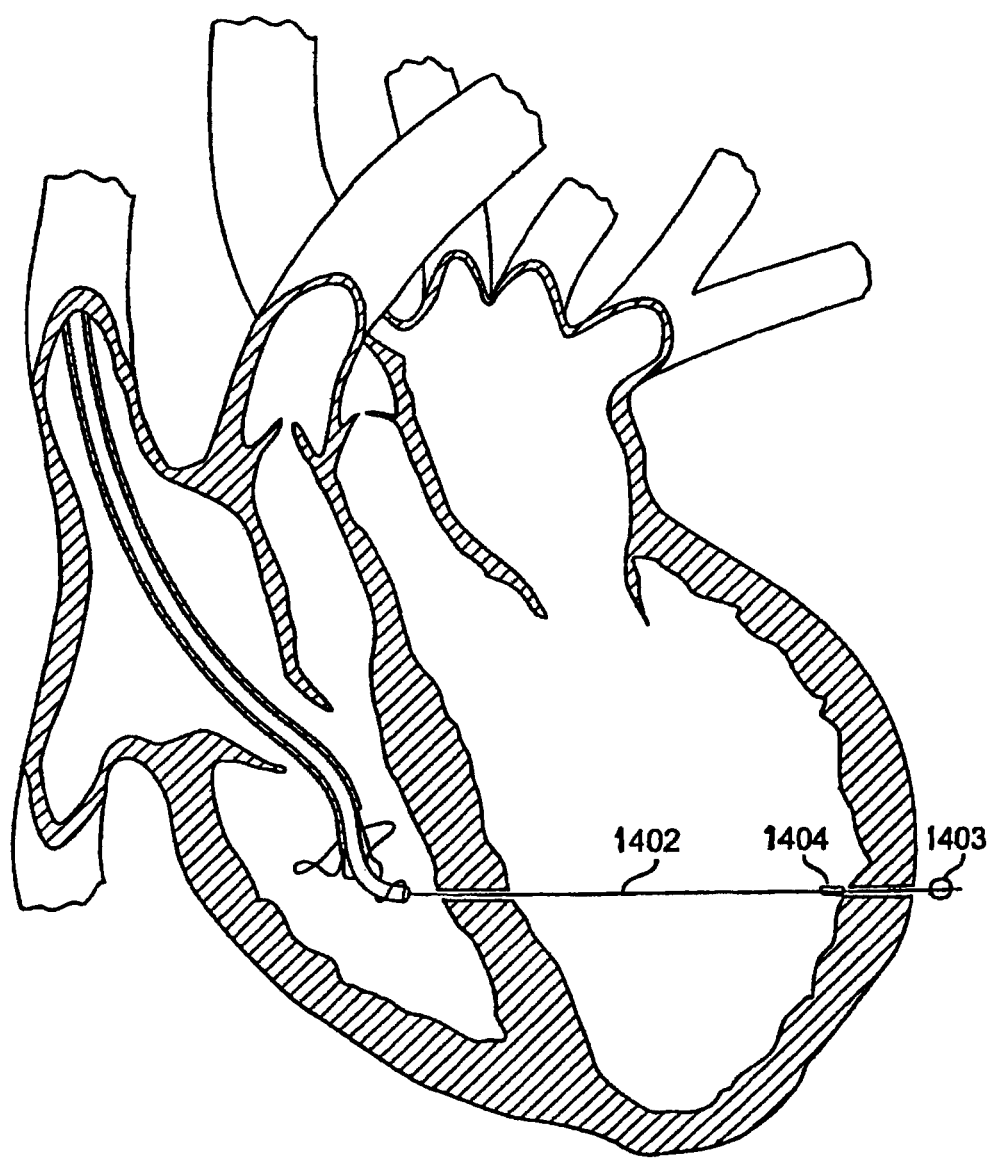
FIG. 34 is a vertical cross-sectional view of the heart showing the guidewire in the position of FIG. 33 with the proximal balloon deflated according to an aspect of the present invention.

As guidewire tip 1402' approaches free wall HW, distal balloon 1403 is deflated, as shown in FIG. 32, and the wire is further advanced into the free wall. Proximal balloon 1404 acts as a stop to limit advancement of guidewire 1402 through free wall HW. This may eliminate or minimize any damage to tissue outside free wall HW of left ventricle LV. Once fully advanced, distal balloon 1403 is re-inflated to secure the position of guidewire 1402 across the left ventricular chamber, as shown in FIG. 33. It is preferred that the distance between balloons 1403, 1404 approximates the thickness of the heart wall.

Figure 35:
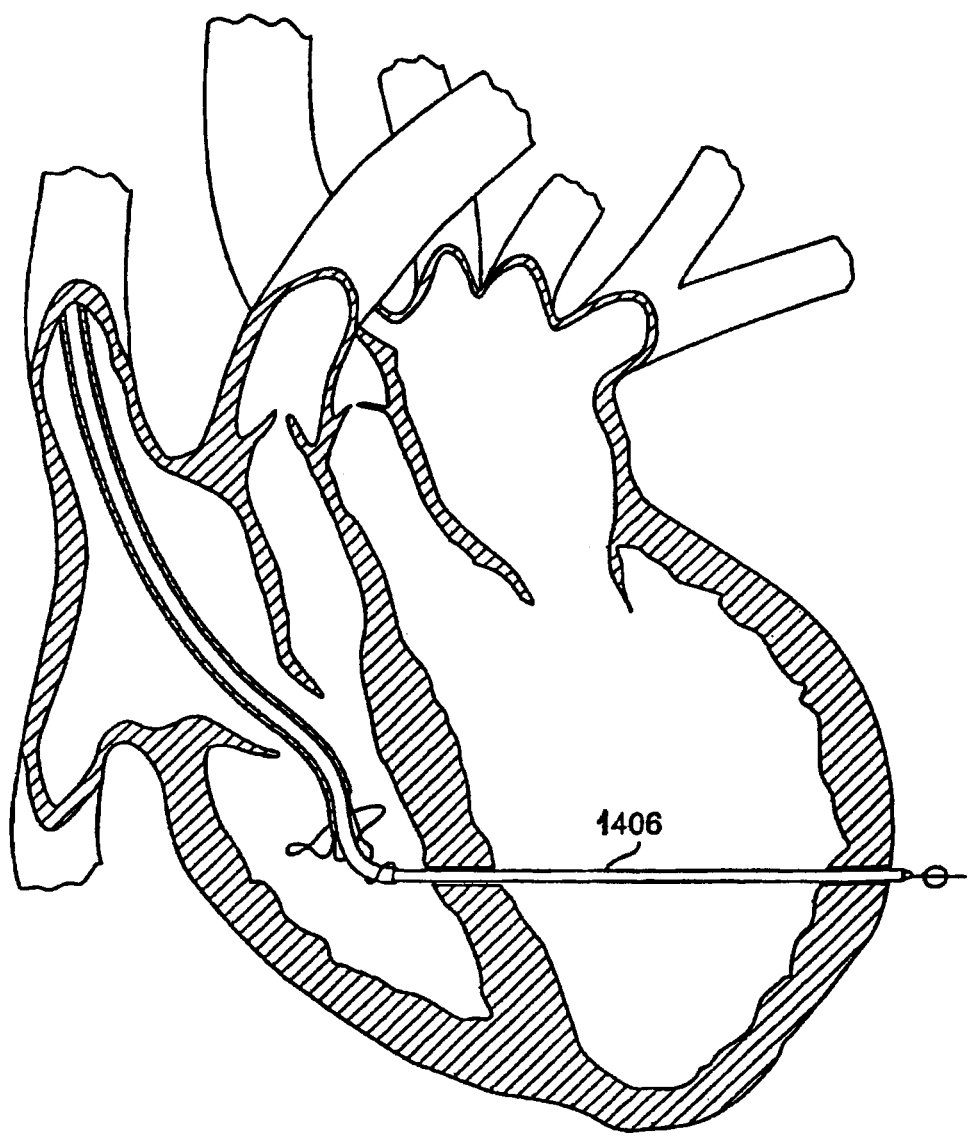
FIG. 35 is a vertical cross-sectional view of the heart showing a splint advancement catheter placed over the guidewire of FIG. 34 according to an aspect of the present invention.
Figure 38:
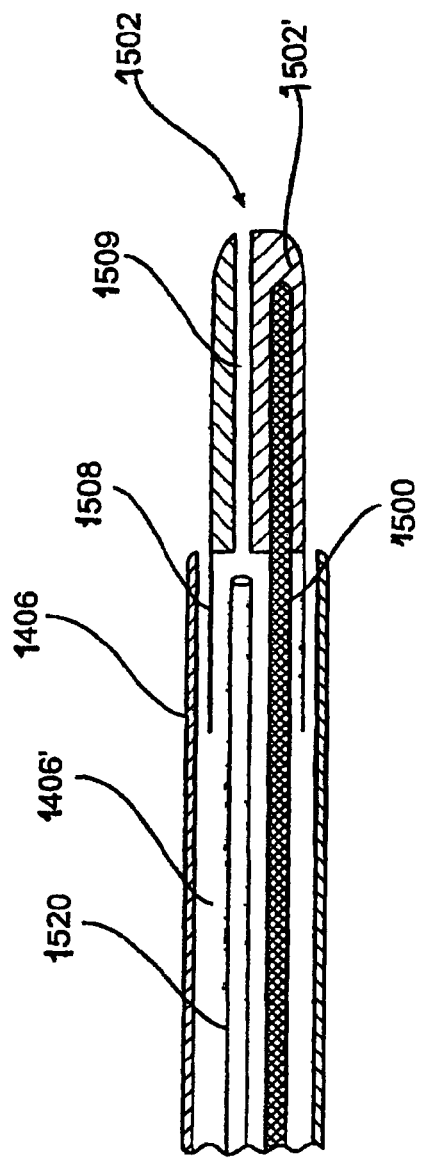
FIG. 38 is a partial, detailed cross-sectional view of the splint advancement catheter, tension member and distal anchor of FIG. 35 according to an aspect of the present invention.

Proximal balloon 1404 is then deflated, as shown in FIG. 33, and a splint advancement catheter 1406 carrying the tension member 1500 and fixed deployable anchor 1502 is advanced over guidewire 1402, as shown in FIG. 35. The structure of splint advancement catheter 1406 with respect to the delivery of the tension member 1500 and deployable anchor 1502 will now be described in more detail with reference to FIG. 38. As shown, catheter 1406 defines a lumen 1406' through which braided tension member 1500 is configured to extend. Tension member 1500 is secured within a distal adhesive portion 1502' of a deployable anchor 1502. This adhesive portion preferably is made of a high strength adhesive such as epoxy, or the like and is also configured to slide through lumen 1406'. A lumen 1509 extends through fixed deployable anchor 1502 adjacent to tension member braid 1500. This lumen also is formed simultaneously within adhesive portion 1502' of anchor 1502. Lumen 1509 and lumen 1406' both pass over the outside of guidewire 1402 (not shown) as advancement catheter 1406 carrying tension member 1500 with deployable fixed anchor 1502 on one end is advanced across the left ventricle LV and through the free wall HW. Anchor 1502 preferably is in the form of an elastic or super-elastic metallic tube including a plurality of preformed tabs 1508 extending proximally from adhesive tube portion 1502'. The tabs 1508 may be formed by several longitudinally-oriented cuts along a portion of the length of the tube. During advancement of tension member 1500, tabs 1508 are prevented from flaring outward by the sheath defining lumen 1406' of splint advancement catheter 1406, as shown in FIG. 38. Upon retraction of the sheath of splint advancement catheter 1406, tabs 1508 are able to expand radially outwardly to their pre formed shape, thus defining distal anchor 1502. A separate push tube 1520 for pushing on anchor 1502 as the catheter 1406 is retracted from the tension member and fixed anchor assembly also is shown in FIG. 38. Push tube 1520 is configured to pass over the outside of guidewire 1402 within lumen 1406' adjacent tension member 1500 to engage with the adhesive portion 1502' of anchor 1502.

Aside from the configurations described above with reference to FIG. 38, the deployable fixed anchor may have a structure similar to that described above with reference to the right ventricle and left ventricle delivery techniques. Similarly, the deployable anchor configurations described in connection with FIGS. 36-38 may be used in conjunction with other delivery techniques described above. Also, the deployable anchor structures described in connection with the previous splint embodiments can be utilized in conjunction with this embodiment.

Elongate tension member 1500 preferably is similar to that described above in connection with the right ventricle delivery method and comprises a braid of high strength polymer fibers, preferably Spectra or other suitable like ultra-high molecular weight polyethylene. Tension member 1500 may also include a covering along its full length made of a thin expanded polytetrafluoroethylene. Alternatively, only the region of tension member 1500 which is disposed inside the ventricular chamber could include a covering.

Tension member 1500 is thus advanced into position by sliding splint advancement catheter 1406 carrying tension member 1500 and anchor 1502 over guidewire 1402. That is, guidewire 1402 will be placed within lumen 1509 of anchor 1502 and then within lumen 1406' of the catheter 1406. The lumen 1406' and the lumen 1509 will move relative to guidewire 1402 to advance catheter 1406, tension member 1500, and anchor 1502 in the configuration shown in FIG. 38 until deployable anchor 1502 protrudes beyond the myocardium of free wall HW. Once tension member 1500 and anchor 1502 are positioned appropriately with respect to the left ventricle and free wall HW, that is, when anchor 1502 retained within the catheter 1406 protrudes beyond the free wall HW as shown in FIG. 35, catheter 1406 is retracted off tabs 1508. This retraction of catheter 1406 enables tabs 1508 to expand radially outward from the remainder of deployable anchor 1502. Push tube 1520 is used to maintain the position of the tension member 1500 during the catheter's retraction to overcome any friction between catheter 1406 and tabs 1508. After anchor 1502 is deployed, both catheter 1406 and push tube 1520 are removed from guidewire 1402 and then guidewire 1402 also is removed.

At this point in the splint delivery technique of FIGS. 30-37, that is, after the deployable fixed distal anchor has been positioned on free wall HW, similar steps as described in connection with both the right ventricle and left ventricle methods above may be followed for the deployment of a second, adjustable anchor pad and for tightening and securing of tension member with respect to the left ventricle. An alternative embodiment of an adjustable anchor to tighten and secure the tension member also may be used in connection with this splint delivery technique, as well as with the other techniques described above. In this alternative embodiment, the proximal anchor may have a similar structure as the distal fixed deployable anchor or may be separately slidable and adjustable on the tension member (such as the adjustable anchor shown in FIGS. 14-17). The proximal anchor also may be pre-attached at an appropriate position on the tension member to provide the desired amount of ventricular shape change.

Figure 45:
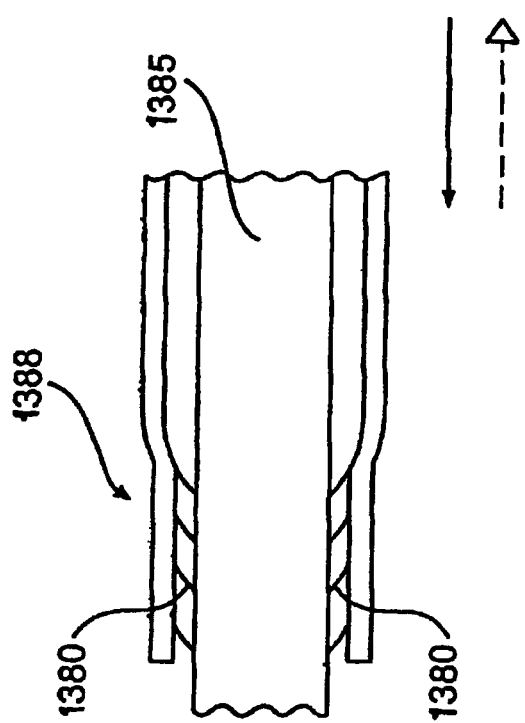
FIG. 45 is a cross-sectional view of an anchor assembly with an inner surface permitting movement with respect to a tension member in only one direction according to an aspect of the present invention.

In the case where the proximal anchor is slidable on the tension member, a one way "ratchet" or friction surface may be disposed on the inner surface of the tubular portion of the anchor to prevent its displacement in one direction. For example, as shown in FIG. 45, the inner surface of the tubular portion of the anchor can be in the form of rings or flared protrusions 1380 that are angled with respect to the longitudinal axis of a tension member 1385 as it is inserted into an anchor 1388. The angled rings or protrusions 1380 are configured so as to permit movement of the anchor with respect to the tension member in one direction but prevent movement in the opposite direction. As illustrated in FIG. 45, the rings or protrusions would permit movement in the direction of the solid arrow, but prevent movement in the direction of the dotted arrow by essentially digging into the tension member surface.

Figure 15:
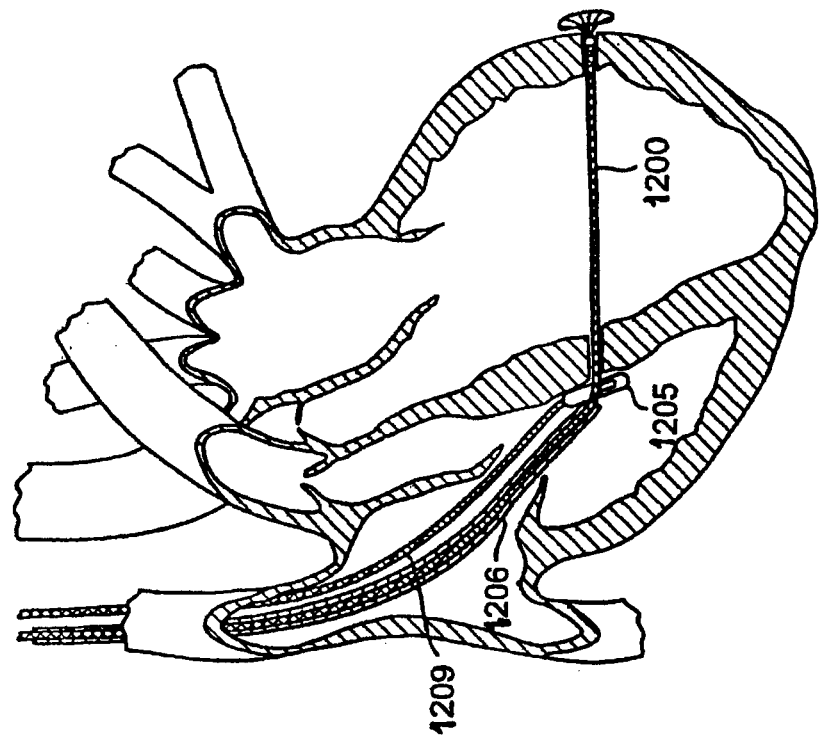
FIG. 15 is a vertical cross-section of the heart showing the securing of the adjustable anchor of FIG. 14 to the tension member to change the shape of the left ventricle according to an aspect of the present invention.
Figure 37:
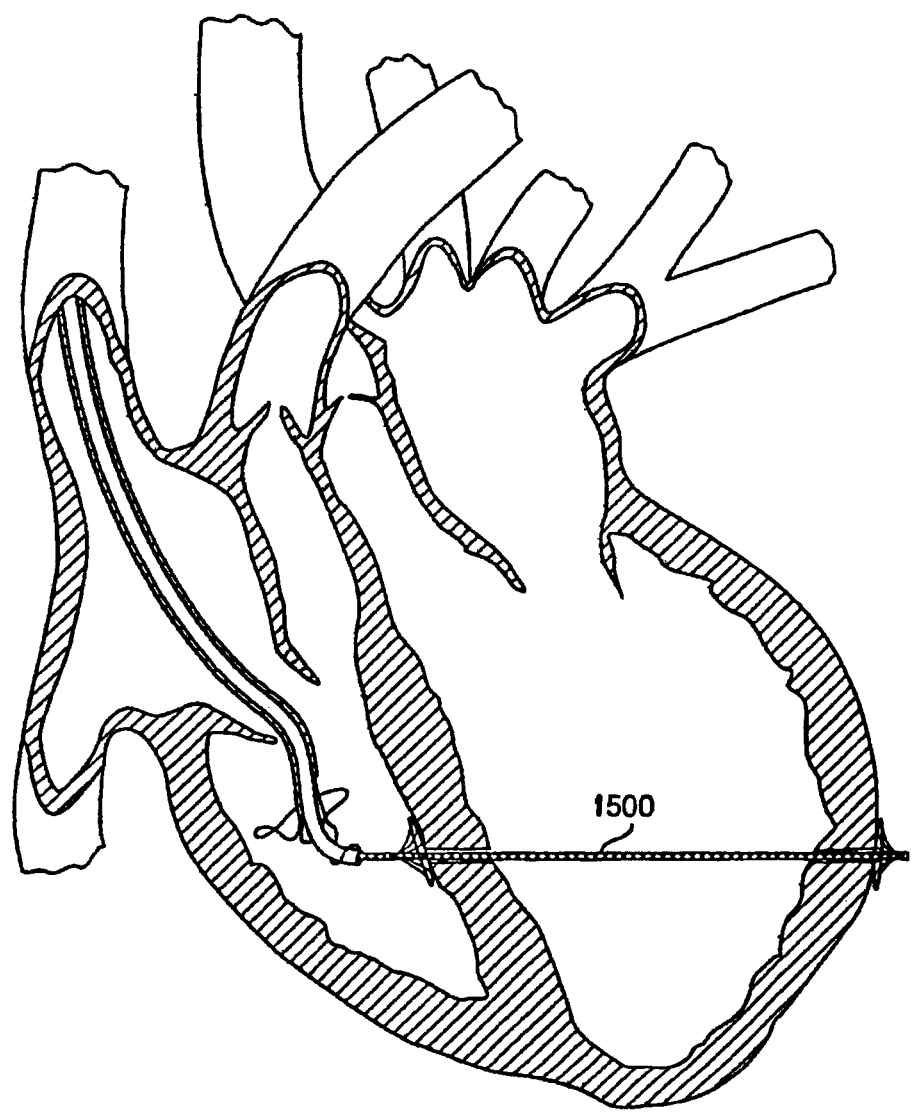
FIG. 37 is a vertical cross-sectional view of the heart showing the splint advancement catheter of FIG. 35 entirely removed and the splint assembly deployed across the left ventricle according to an aspect of the present invention.

A tightening device such as that described and shown in FIG. 15 may be utilized to advance the deployed anchor into position. In this case, the anchor may be initially positioned such that when the sheath of the splint advancement catheter is further withdrawn, the proximal anchor also would deploy within the right ventricle RV adjacent to the septal wall SW. The tightening device could then be used to advance the position of the proximal anchor to a desired position against the septal wall SW, as shown in FIG. 37. Alternatively, the delivery catheter itself could be used to advance the deployed proximal anchor to the desired position. Once the proximal anchor is positioned to its appropriate location, any excess tension member length extending beyond the proximal anchor may be severed in a manner similar to that described above in connection with FIG. 16.

In the alternative case where proximal anchor is pre attached at a specified distance from the distal anchor, the left ventricle should be deformed prior to the pad deployment. The delivery catheter can act as a temporary proximal anchor, while the tension member and distal anchor are pulled proximally. Once the proper shape change of the left ventricle is attained, the proximal anchor may be deployed upon further retraction of the sheath of the splint advancement catheter. In this embodiment, preferably the distance between the distal and proximal anchors will be selected prior to delivery such that a desired shape change of the heart chamber may be obtained, since the adjustability of the shape change will be limited by the fixed position of the proximal anchor on the tension member. The delivery catheter may then be removed and excess tension member severed, again as described with reference to FIG. 16.

While the splint delivery methods and devices just described in connection with FIGS. 30-37 were in the context of a right ventricle approach, it is also contemplated to utilize the delivery devices and methods in a direct left ventricle approach as well. In a direct left ventricle approach, two delivery catheters simultaneously could be utilized to position a splint from within the left ventricle in manners similar to those described with reference to FIGS. 24-29.

Other embodiments of a deployable, fixed heart-engaging assembly, or anchor, also are contemplated as within the scope of the present invention and are shown in FIGS. 39-42. A preferred tension member used in the various embodiments of the present invention is described in the '049 application, incorporated by reference above, and is formed of several multifilament bundles of a high strength polymer. These bundles are braided together in a relatively tight configuration. Certain combinations of bundle size, number of bundles, and pick count, described in more detail in the '049 application, result in a braid with several preferred properties as also described in the '049 application, incorporated by reference above. One property that may result from such a braid construction includes a relatively stable braid diameter that does not deform to a great extent if subjected to axial compression or internal radially-outward directed forces. However, a braid formed with a lower pick count has a greater diametric expandability when subjected to such forces. For example, a braid woven of the same material and having approximately 16 to approximately 64 bundles and approximately 2 to approximately 15 picks per inch may more readily expand in diameter, upon the application of a radial force directed outwardly from within the braid. This expandable property of a braid can be utilized in the formation of yet another alternative deployable anchor structure.

Figure 39:
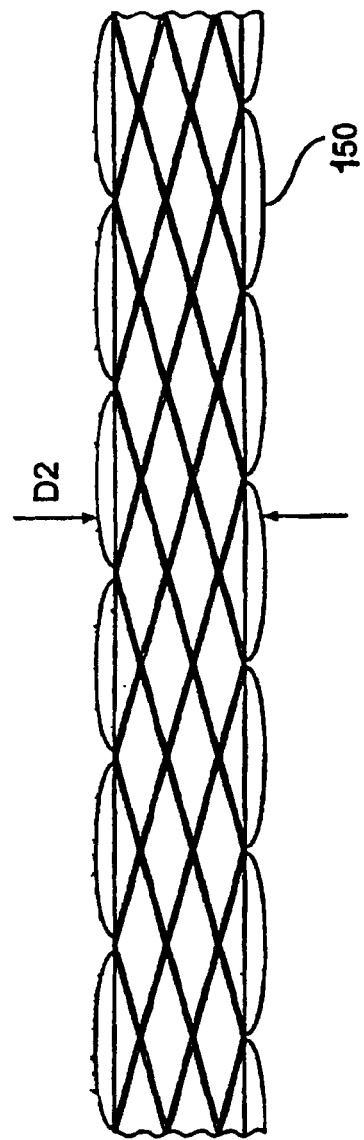
FIG. 39 is a partial side view of a braided tension member according to an aspect of the present invention.
Figure 40:
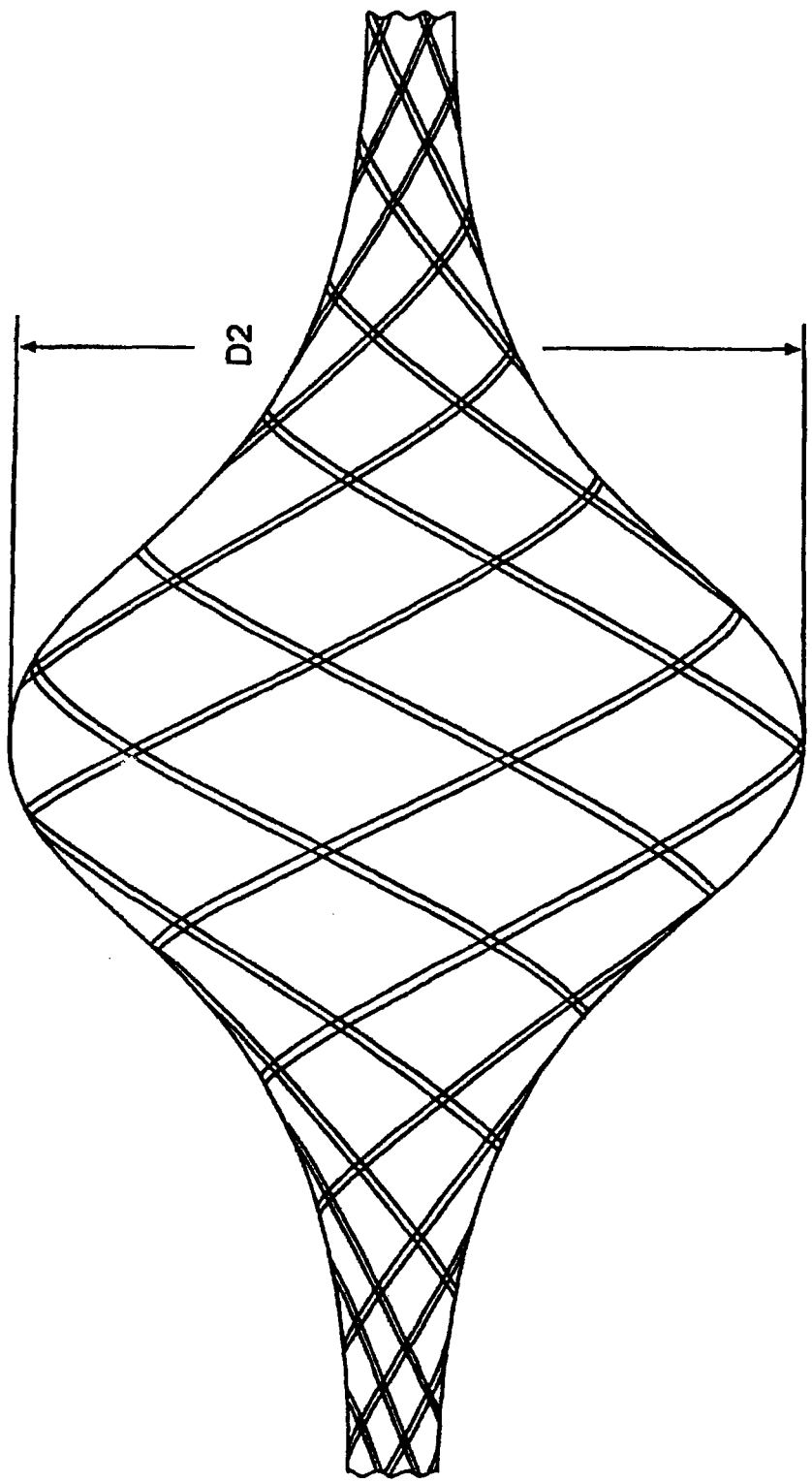
FIG. 40 is a partial side view of a braided tension member having a diametrically expandable portion according to an aspect of the present invention.

For example, FIG. 39 is a relatively simplified schematic illustrating a tension member 150 formed of a braid of relatively low pick count in its natural (i.e., non-stressed) as braided condition. The braid is uniformly relatively small in outer diameter D1. When the braid is under tension, and absent any other deforming forces, the diameter D1 of the braid remains relatively small. FIG. 40 illustrates the same braided tension member 150 as in FIG. 39, but shows the braid with a local application of an outward radially directed force from within the braid. Since the braid pick count is relatively low, the braid has the capacity to expand at the point of application of the radial force to a diameter D2, which is several times its original diameter D1.

Figure 41:
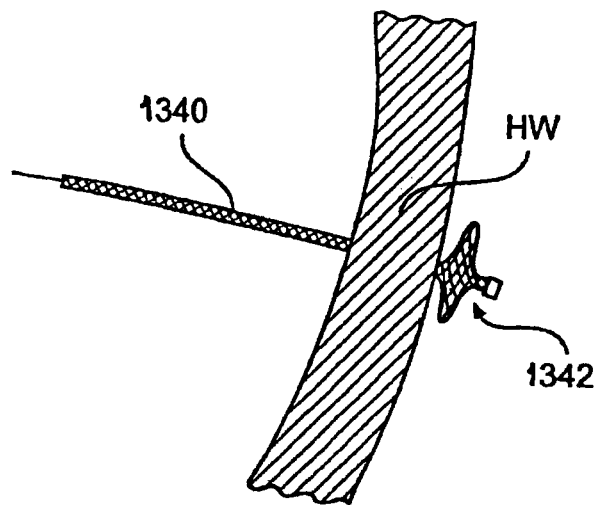
FIG. 41 is a partial perspective view of the tension member of FIG. 40 forming a free wall anchor at the diametrically expandable portion according to an aspect of the present invention.
Figure 41A:
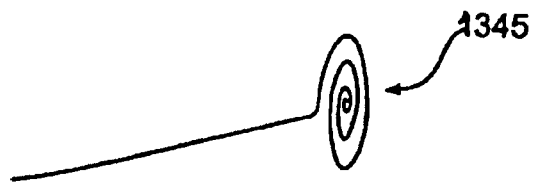
FIG. 41a is a partial perspective view of a spiral-shaped deployable wire used to diametrically expand the tension member of FIG. 40 to form the anchor of FIG. 41 according to an aspect of the present invention.
Figure 41B:
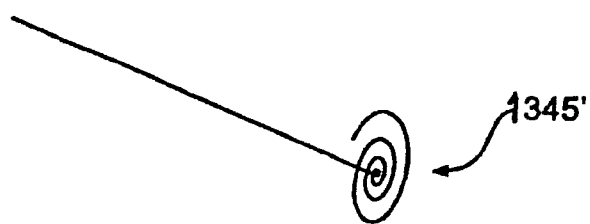
FIG. 41b is a partial perspective view of a spiral-shaped deployable wire used to diametrically expand the tension member to form the anchor having a spiral formed in an opposite direction to the spiral of FIG. 41a according to another aspect of the present invention.

FIG. 41 shows a tension member 1340 having a braid configuration such a that shown in FIGS. 39 and 40 utilized for an integral expandable distal anchor 1342 of tension member 1340. At least a portion of the tension member 1340 is woven at a relatively low pick count to allow for that portion to form into the expandable distal anchor 1342. Alternatively, the entire tension member 1340 can be uniformly woven at the relatively low pick count. Several methods for creating an outward radial force from within the braid to form anchor 1342 are contemplated. These methods include using an elastic or shape memory wire disposed inside the braid of tension member 1340 during placement across the ventricular wall HW. A preferred wire 1345 is shown in FIG. 41a. Note that it is contemplated that the direction of spiral of the wire can be opposite to that shown in FIG. 41a, as shown in FIG. 41b. Wire 1345 preferably has a natural shape in the form of a disc shaped spiral. When tension member 1340 is delivered using a splint advancement catheter of the types described above, the spiral will have a straightened configuration. Upon removal of the of the splint advancement catheter from the portion of the tension member 1340 which will form the distal anchor 1342, however, the spiral shape of wire 1345 may be re established, thereby forcing the braided portion surrounding it to expand in diameter into a disc like shape, as shown in FIG. 41. The wire may either be pre-loaded into the tension member or may be advanced into the tension member once the tension member has been positioned with respect to the heart wall and the catheter has been retracted enough to expose a portion of the tension member that is outside the heart wall HW. The force of the catheter on the wire keeps the wire in its straightened configuration. The smaller diameter portion of the spiral forms first, and as more of the wire is advanced through the tension member beyond the catheter, the spiral grows in diameter until the full spiral is re established. Alternatively, as shown in FIG. 41b, the large diameter portion of the spiral may for first, as the wire 1345' is advanced. To help prevent wire 1345 from penetrating through the interstices of the braid of tension member 1340, a thin membrane, preferably made of an elastic material for example, is disposed along the inside of the braid in the area where the spiral portion of wire 1345 is positioned.

In this embodiment, wire 1345, particularly in the spiral region, preferably will remain together with the braid of tension member 1340 even after diametric expansion in order provide the anchoring rigidity needed to secure the splint in place on the heart. Initially, the spiral portion of wire 1345 may carry a significant portion of the load of anchor 1342. However, it is anticipated that over time, the expanded braid forming anchor 1342 would become ingrown with scar tissue, and therefore a relatively large portion of the chronic mechanical loading may be carried by the filaments of the braid. Using filaments of ultra-high molecular weight polyethylene has been shown to produce a tension member and anchor having high strength and high fatigue resistance. A portion of the wire that does not form the spiral may be removed, for example by torquing the wire and breaking it at a location slightly proximal to the spiral.

To prevent any of the braided portion distal of the expanded region from "creeping" back over the spiral region, the distal most region of the braid preferably is either fused or banded.

This will prevent expansibility in those regions. Alternatively, those regions of the braided tension member could be woven with a higher pick count.

Figure 42:
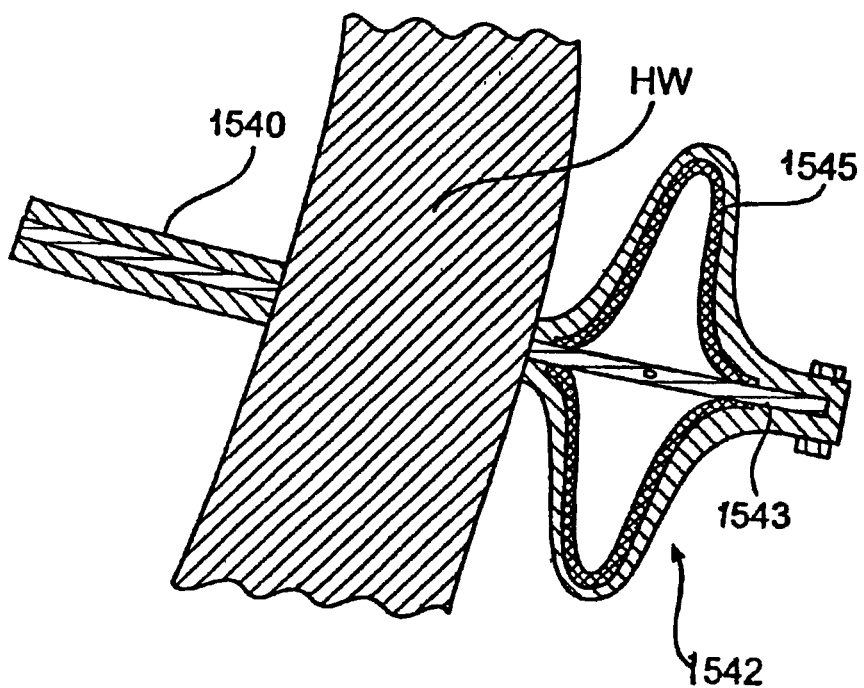
FIG. 42 is a partial perspective view of a diametrically expandable tension member forming an anchor portion by using an inflated balloon within the expandable portion of the tension member to cause diametric expansion according to an aspect of the present invention.

An alternative device for causing expansion of an expandable braid portion of a tension member 1540 includes an inflatable balloon disposed inside braided tension member at the expandable portion forming the anchor, as shown in FIG. 42. Inflatable balloon 1545 can be positioned in the desired location within tension member 1540 either before advancement of the tension member across the ventricular wall, or after, as shown in FIG. 42. Preferably, balloon 1545 is formed of an elastomeric material such as silicone or urethane, or the like, and has a disc like shape upon expansion. A lumen 1543 connecting the interior of balloon 1545 to an inflation device (not shown) may extend along the inside of braided tension member 1540. In a preferred embodiment, the material used to expand balloon 1545, and thus the region of the braided tension member 1540 forming distal, deployable anchor 1542, includes a curable material such as RTV silicone, epoxy, urethane, or the like. Similar to the spiral anchor embodiment discussed above, the cured material forming the balloon may carry a significant load initially, but upon ingrowth of the expanded braided region of the tension member, the filaments of the braid would be the primary chronic load carrying members.

One of ordinary skill in the art would recognize that the alternative distal anchors described above could be utilized in conjunction with any of the delivery techniques of the present invention and could be used as either the free wall anchor or septal wall anchor with modifications as necessary.

Figure 36:
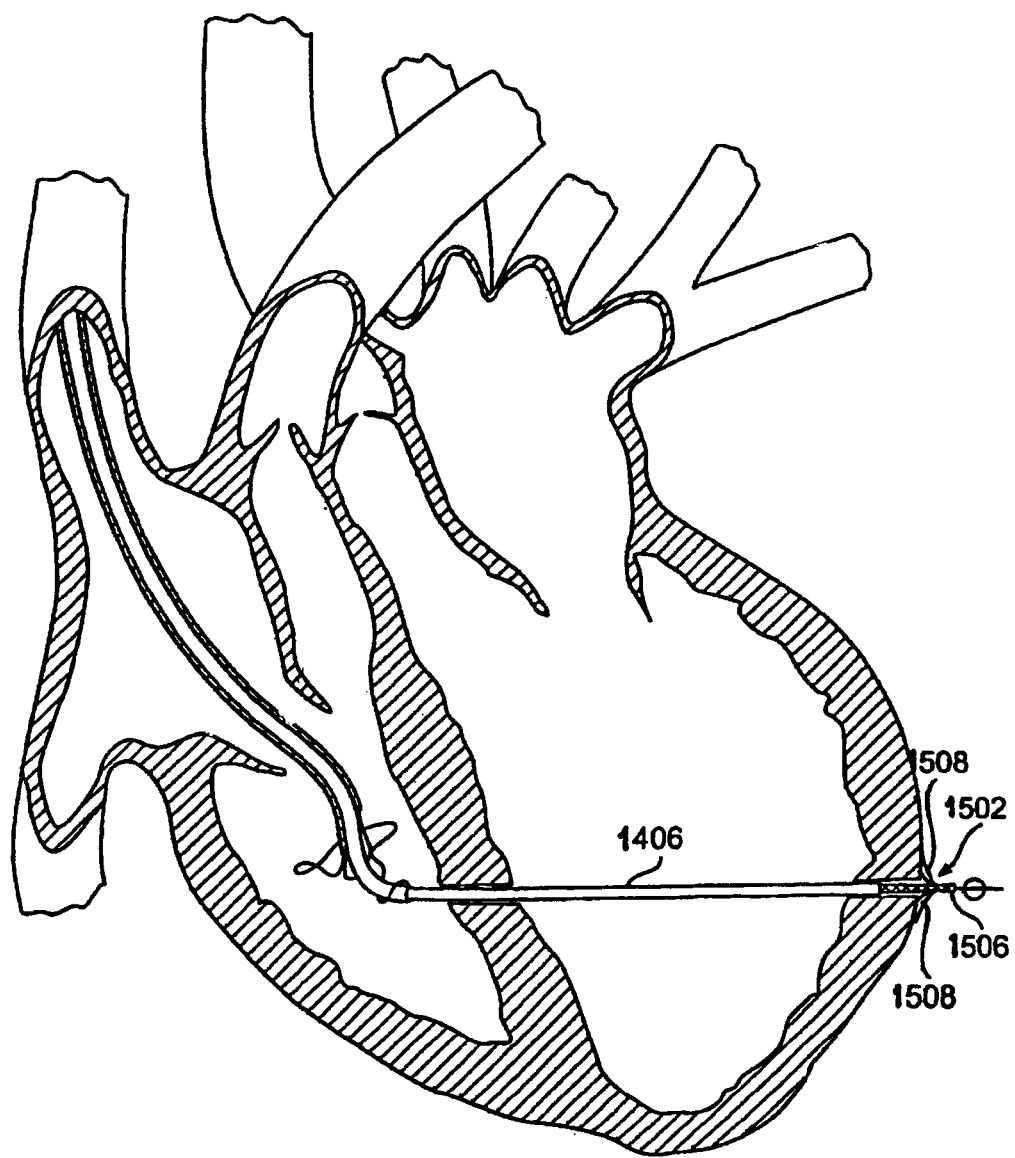
FIG. 36 is a vertical cross-sectional view of the heart showing the splint advancement catheter of FIG. 35 being removed from a tension member and deployable anchor of the splint according to the present invention.

Another alternative embodiment for an expandable anchor would utilize an anchor similar to the expandable tab anchor described above with reference to FIGS. 36-38. However, in this embodiment, that anchor would be merely temporary, and could be designed to be relatively small and low profile, for easy delivery, but may not have the adequate strength and durability to be a permanent chronic anchor. In this case, a permanent anchor, similar to the adjustable pad anchor assembly described in the '049 application incorporated above could be delivered as a replacement to that temporary anchor. Once the temporary anchor is positioned, as shown in FIG. 36, a small surgical incision may be made between the ribs adjacent the free wall HW of the left ventricle LV, thus creating an access port to deliver the permanent anchor. Alternatively, a trocar may be positioned in that same location. A snare device positioned within the port or trocar can be used to grab the temporary anchor and tension member and pull the anchor off of the tension member and outside of the patient. An adjustable anchor pad as described in the '049 application and similar to the description of FIGS. 14 and 15 above then may be attached to the braid outside of the patient, using the staple methodology described previously with reference to FIG. 15 and the '049 application. The anchor can then be pulled back into position by retracting the other end of the tension member via the length of the tension member that remains outside the jugular vein. The septal wall anchor in this case preferably would be in the form of the solid anchor and delivered in the manner described above in conjunction with FIGS. 14-17. Overall, this procedure would be a combination endovascular and "minimally invasive" surgical operation. In this embodiment, preferably both anchor pads would be of a solid type construction.

An alternative proximal anchor also may utilize the expandable capability of a relatively low pick count braid, in a manner similar to that described above for the distal, or free wall, anchor. In this embodiment, the entire braid of the tension member preferably includes the relatively low pick count permitting diametric expansion. The tension member and distal anchor could be delivered using any of the approaches described herein, but preferably one of the right ventricle approach methods. After the distal, or free wall, anchor is delivered, the proper ventricle shape change can be induced using a tightening device in the form of a simple tube, such as the one described above, but without the anchor shown in FIG. 15. A balloon or spiral wire type of expander device as described in connection with the distal anchors shown in FIGS. 41, 41a, and 42, may be positioned in the proper location and caused to expand a portion of the braid external to the septal wall. If a balloon type expansion device is used, it may also include a detachable inflation tube, such that when the balloon is inflated with a curable material, the inflation tube can be removed prior to the excess tension member length being severed. It is also contemplated that such an expandable proximal anchor can be secured to the end of the tension member at a location adjacent to an exterior surface of a heart wall other than the septal wall, such as a wall surrounding the right ventricle, for example.

Figure 43:
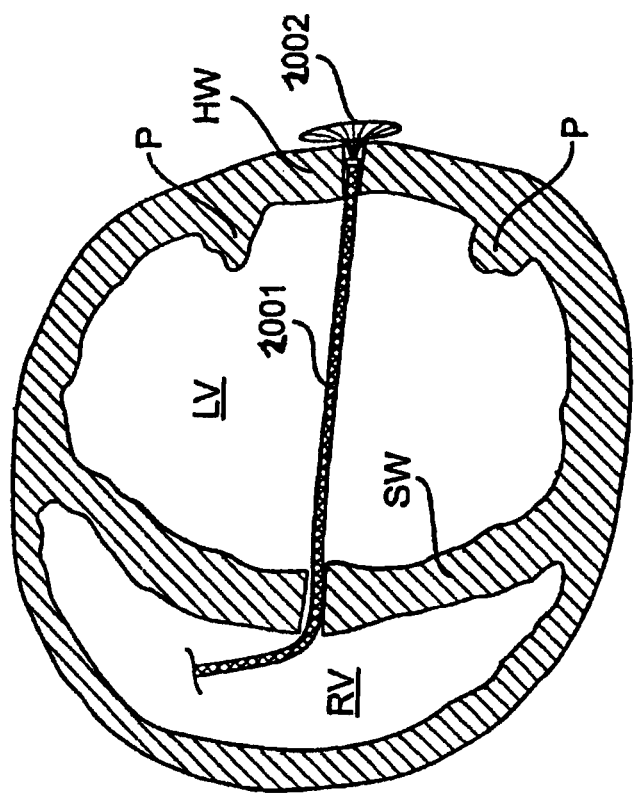
FIG. 43 is a transverse cross-sectional view of the heart showing a preferred placement of a tension member of a splint assembly to treat a mitral valve according to an aspect of the present invention.

The methods described above to place the splint assemblies with respect to the heart can be repeated for any desired number of splint assemblies to achieve a particular configuration. The length of the tension members extending between the free wall and septal wall anchors also can be optimally determined based upon the size and condition of the patient's heart. It should also be noted that although the left ventricle has been referred to here for illustrative purposes, the apparatus and methods of this invention can be used to splint multiple chambers of a patient's heart, including the right ventricle or either atrium, or can be used to aid the function of valves, such as the mitral valve. An example of a preferred position of a splint assembly 2000 improves mitral valve function, as well as reducing stress in the left ventricular walls. The valve function is improved by aiding in the apposition of valve leaflets when positioned as shown in FIG. 44. Preferably, three splints are placed in a coplanar fashion, bisecting the left ventricle LV of the heart. The superior-most splint 2000 is placed at approximately the level of the heads of the papillary muscles PM, and the additional two splints (not shown in FIG. 44) are placed inferiorly toward the apex. The preferred orientation shown in FIG. 44 both bisects the left ventricle LV and avoids key structures such as coronary vessels and the like. The splints according to this orientation also extend through the septum SW and enter a portion of the right ventricle RV. In the preferred placement, as with those described above, heart-engaging assemblies 2002, 2003 will be positioned adjacent an exterior surface of a free wall HW surrounding the left ventricle LV and adjacent an exterior surface of the septal wall SW within the right ventricle RV. Further details regarding splinting devices and methods for treating heart valves can be found elsewhere herein. Although any of the delivery methods described above could be used to implant the splint device in this manner, FIG. 43 shows a short axis cross-section of a heart and a preferred endovascular technique wherein the elongate tension member 2001 having a deployable fixed anchor 2002 on its distal end is delivered through the right ventricle RV and then into the left ventricle LV.

Furthermore, the alignments of the splints with respect to the heart that are described above are illustrative only and may be shifted or rotated about a vertical axis generally disposed through the left ventricle and still avoid the major coronary vessels and papillary muscles. In addition, the inventive devices and methods can be implanted to treat a heart having aneurysms or infarcted regions similar to those described in prior U.S. application Ser. No. 09/422,328 discussed earlier herein and incorporated above.

The various components of the splint assembly to be implanted in the heart should be made of biocompatible material that can remain in the human body indefinitely. Any surface engaging portions of the heart should be atraumatic in order to avoid tissue damage and preferably formed of a material promoting tissue ingrowth to stabilize the anchor pad with respect to the surfaces of the heart.

It will be understood that this disclosure, in many respects, is only illustrative. Changes may be made in details, particularly in matters of shape, size, material, number and arrangement of parts without exceeding the scope of the invention. Accordingly, the scope of the invention is as defined in the language of the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for improving a function of a patient's heart, comprising:
   securing a heart treatment device to a portion of the patient's heart, wherein the heart treatment device comprises at least one member secured relative to a valve of the heart, wherein the heart treatment device is configured to assist in improving apposition of leaflets of the valve;
   monitoring the function of the patient's heart; and
   adjusting a configuration of the heart treatment device based on data obtained from monitoring the function of the patient's heart.

2. The method of claim 1, wherein a portion of the heart treatment device is disposed outside of the patient's heart.

3. The method of claim 1, wherein a portion of the heart treatment device is disposed within a structure of the patient's heart.

4. The method of claim 1, wherein the heart treatment device is a passive device.

5. The method of claim 1, wherein the heart treatment device does not require a stimulus to function.

6. The method of claim 1, wherein the valve is an atrioventricular valve.

7. The method of claim 6, wherein the atrioventricular valve is a mitral valve.

8. The method of claim 1, further comprising delivering the heart treatment device to the patient's heart.

9. The method of claim 8, wherein delivering the heart treatment device includes endovascularly delivering the heart treatment device.

10. The method of claim 1, wherein monitoring the function of the patient's heart includes real-time monitoring of the function.

11. The method of claim 10, wherein real-time monitoring includes ultrasound imaging.

12. The method of claim 1, wherein the heart treatment device is configured to alter a positioning of a heart structure, throughout a cardiac cycle.

13. The method of claim 12, wherein securing the device to a portion of the patient's heart alters the positioning of the heart structure.

14. The method of claim 13, wherein the heart structure is an annulus of a heart valve.

15. The method of claim 13, wherein the heart structure is a heart wall.

16. The method of claim 15, wherein the heart wall is an external heart wall.

17. The method of claim 1, wherein securing the device to a portion of the patient's heart includes placing the device in contact with structure other than structure of a heart valve.

18. The method of claim 1, wherein adjusting a configuration of the heart treatment device alters a positioning of a heart structure, throughout a cardiac cycle.

19. The method of claim 18, wherein the heart structure is a heart wall.

20. The method of claim 18, wherein the heart structure is an annulus of a heart valve.

21. A method for treating a valve of a patient's heart, comprising:
   implanting a device relative to the patient's heart, such that a portion of the device is disposed externally of the patient's heart, wherein the heart treatment device comprises at least one member secured relative to a valve of the heart, wherein the heart treatment device is configured to assist in improving apposition of leaflets of the valve;
   monitoring in real-time a function of the valve;
   evaluating monitoring data; and
   adjusting the device relative to the patient's heart based on the monitoring data so as to alter the function of the valve, throughout a cardiac cycle.

22. The method of claim 21, wherein the valve is a mitral valve.

23. The method of claim 21, wherein adjusting the device relative to the patient's heart includes deforming a wall of the patient's heart.

* * * * *